United States Patent [19]

Smith et al.

[11] Patent Number: 5,487,990
[45] Date of Patent: Jan. 30, 1996

[54] GLUCOSE-REGULATED PROMOTER OF YEAST ACETYL-COA HYDROLASE

[75] Inventors: John A. Smith, Scotch Plains, N.J.; Fang-Jen S. Lee; Lee-Wen Lin, both of North Bethesda, Md.

[73] Assignee: The General Hospital Corporation, Boston, Mass.

[21] Appl. No.: 921,796

[22] Filed: Jul. 30, 1992

Related U.S. Application Data

[63] Continuation-in-part of Ser. No. 480,452, Feb. 15, 1990, abandoned, which is a continuation-in-part of Ser. No. 213,943, Jul. 1, 1988, abandoned, and a continuation-in-part of Ser. No. 297,003, Jan. 13, 1989, abandoned.

[51] Int. Cl.[6] .......................... C12N 1/19; C12N 15/81; C12N 15/11
[52] U.S. Cl. .................. 435/172.3; 435/254.2; 435/254.21; 435/254.22; 435/254.23; 435/320.1; 536/24.1; 935/37; 935/69; 530/371
[58] Field of Search ................ 536/24.1; 530/371; 435/320.1, 254.2, 254.21, 254.22, 254.23, 172.3; 935/37, 69

[56] References Cited

U.S. PATENT DOCUMENTS

| | | | |
|---|---|---|---|
| 4,394,443 | 7/1983 | Weissman et al. | 435/6 |
| 4,771,002 | 9/1988 | Gelvin | 435/172.3 |

FOREIGN PATENT DOCUMENTS

| | | | |
|---|---|---|---|
| 0123811 | 11/1984 | European Pat. Off. | |
| 0255377 | 2/1988 | European Pat. Off. | C12N 15/00 |
| WO90/00003 | 11/1990 | WIPO | A01H 1/04 |

OTHER PUBLICATIONS

Van Dyck et al 1992 Yeast 8:769–776.
Griggs et al 1991 Proc Natl Acad Sci USA 88:8597–8601.
Elion et al 1990 Cell 60:649–664.
Fujimura 1992 Molec Gen Genet 235:450–452.
Guarente et al 1982 Proc Natl Acad Sci USA 79:7410–7414.
Nehlin et al 1991 The EMBO Journal 10(11):3373–3377.
Lee, F.-J. S. et al., *J. Biol. Chem.* 265:7413–7418 (1990).
Lee, F.-J. S. et al., *Eur. J. Biochem.* 184:21–28 (1989).
Prass, R. L. et al., *J. Biol. Chem.* 255:5215–5223 (1980).
Söling, H.-D. et al., *Eur. J. Biochem.* 147:111–117 (1985).
Robinson, J. B. et al., *Biochem. Biophys. Res. Commun.* 71:959–965 (1976).
Liedvogel, B. et al., *Plant Physiol.* 69:897–903 (1982).
Zemlyanukhina, O. A. et al., *Referativnyi Zhurnal Biologiya* *10G191* (1985), Abstract #0507544.
Zemlyanukhina, O. A. et al., *Doklady: Biochem.* 291(46):392–394 (1987) (translation of Akad. Nauk SSSR Doklady 291(5):1250–1253 (1986)).
Knauf, V. C. *Trends Biotech.* 5:40–47 (1987).
Brooks, T. L., *Hydroxylapatite*, (Calbiochem–Behring, publishers) pp. 8–11, (1981).
Schell, J. et al., *Bio/Technology* 1:175–180 (1983).
Wallace, B. et al., *Methods Enzymol.* 152:432–442 (1987).
Lee, F.-J. S. et al., *J. Biol. Chem.* 263(29):14948–14955 (1988).
Travis, G. H. et al., *J. Biol. Chem.* 259(23):14406–14412 (1984).
Kobayashi, K. et al., *J. Biol. Chem.* 262(24):11435–11445 (1987).
Bernson, V. S. M., *Eur. J. Biochem* 67:403–410 (1976).
Ebisuno, S. et al., *Am. J. Physiol.* 255 (*Regulatory Integrative Comp. Physiol.* 24):R724–R730 (1988).
Guarente, L., *Methods in Enzymology* 101:181–191 (1983).
Guarente, L., et al., *Proc. Natl. Acad. Sci. USA* 78(4):2199–2203 (1981).
Henikoff, S., *Gene* 28:351–359 (1984).
Namboodiri, M. A. A. et al., *J. Biol. Chem.* 255(13):6032–6035 (1980).

*Primary Examiner*—Patricia R. Moody
*Attorney, Agent, or Firm*—Sterne, Kessler, Goldstein & Fox

[57] ABSTRACT

This invention is directed to the acetyl-CoA hydrolase enzyme of yeast and to a method for purifying acetyl-CoA hydrolase. The enzyme has a molecular weight of about 64,000 daltons and an enzyme activity of greater than 20 units wherein one unit of acetyl CoA hydrolase activity is defined as the amount of enzyme able to inhibit 1 unit of acetyltransferase activity and 1 unit of acetyltransferase activity is defined as the amount of enzyme needed to transfer 1 pmol of [$^3$H] acetyl group from [$^3$H] acetyl coenzyme A to ACTH (1–24) in the acetyltransferase standard enzyme assay under standard conditions. The invention is further directed to the glucose-repressible promoter which regulates the expression of the acetyl-CoA hydrolase gene in yeast, to vectors incorporating this promoter and to host cells transformed with such vectors.

16 Claims, 17 Drawing Sheets

PEPTIDE 19-1  F   N   L   F   V   G   A   S   A   G   P   E   E   N   R
PROBE A1    3'- AAG TTC AAC AAG CAA CCA CGA AGA CGA CCA GGT CTT CTT TTG TCT -5'
                         *           *       *                       * *

PEPTIDE 10-2  V   V   A   I   V   E   S   T   M   R
PROBE A2    3'- CAA CAA CGA TAA CAA CTT AGG TGG TAC TCT -5'
                 *   *       *       *

-613                        GTTAGCCATCATTATCATTAAAATATCAACCCGAAGAACA

-573 ATGTATACATATACATATACGTACACATATACATATGTACATATGACATACGTATTAGCC

-513 GCTGAGGACGCGGACGTATAAAAGGACAATACTTATATGGAGCTAAGGGGAGCAGTTACG

-453 CAACTCCGTGATCGCGCGCCACGGGCCGTCGGCGGCTGTTAATTGAAGAAAAAAAAAATG

-393 AAGAACCACAAGGGGTGATCCATATAGGTGACTAGCATCATCCCCTGCGACGCGCGGCCC

-333 GCCGGGCAAAGGCGGGCAATGCGCGCTGCTGATTGGCCTCGAGGACAACGCCCTCAACCA

-273 CATCCGCAACAGCCAATCCCATCGGAGCGTCAAACTACCAAAGTAGTGATTGTATGGATC

-213 ACCACTGTATTGTGGACGGTAAGCGCTTGCTGGAGCAAATGTGTAATCAAGTTGCTGTGT

-153 ATATATAGACGTTAGATGTGTTCTACCCCTTCTTTTGTCTTGTGCCCACCGGGCTTACAT

- 93 TAGCACACAAAGCAGCAAGAGACCGTCTTACTAGACAATAGCGGCAAAACAAACAACACA

- 33 TTTCTTTTTTTCTTTTTCACATATTGCACTAAAATGACAATTTCTAATTTGTTAAAGCAG
                                              M  T  I  S  N  L  L  K  Q

28 AGAGTTAGGTATGCTCCCTATCTGAAAAAAGTTAAGGAAGCTCACGAGCTTATTCCATTG
  10  R  V  R  Y  A  P  Y  L  K  K  V  K  E  A  H  E  L  I  P  L

88 TTCAAGAATGGTCAGTACCTTGGGTGGTCCGGTTTTACAGGAGTGGGTACTCCCAAGGCA
  30  F  K  N  G  Q  Y  L  G  W  S  G  F  T  G  V  G  T  P  K  A

148 GTGCCGGAGGCACTGATAGATCACGTGGAGAAGAACAATTTACAAGGGAAGTTGAGATTC
  50  V  P  E  A  L  I  D  H  V  E  K  N  N  L  Q  G  K  L  R  F
                                                              <--

208 AACCTTTTTGTTGGAGCTTCTGCTGGTCCAGAGGAAAACCGTTGGGCTGAACACGACATG
  70  N  L  F  V  G  A  S  A  G  P  E  E  N  R  W  A  E  H  D  M
       -------------- 19-1 -------------------->

FIG.7C

```
268  ATCATTAAGAGAGCCCCTCATCAAGTAGGGAAACCCATTGCAAAGGCAATTAACCAGGGT

90   I  I  K  R  A  P  H  Q  V  G  K  P  I  A  K  A  I  N  Q  G
                    <------ 1-2 ------>

328  AGAATTGAGTTCTTTGATAAACATCTGTCCATGTTCCCTCAGGATCTGACATACGGGTTC
110   R  I  E  F  F  D  K  H  L  S  M  F  P  Q  D  L  T  Y  G  F
        <-------------------------------- 35 ---------------------

388  TACACCAGGGAAAGAAAAGACAACAAAATCCTTGATTATACTATAATCGAGGCAACGGCC
130   Y  T  R  E  R  K  D  N  K  I  L  D  Y  T  I  I  E  A  T  A
      ------>                          <------------------------ 34 -

448  ATTAAAGAGGACGGGTCTATCGTCCCAGGTCCCTCTGTCGGTGGTTCTCCAGAATTCATT

150   I  K  E  D  G  S  I  V  P  G  P  S  V  G  G  S  P  E  F  I
      ----------------------------->

508  ACAGTCAGTGATAAAGTGATTATTGAGGTTAACACGGCTACGCCTTCGTTCGAGGGTATT

170   T  V  S  D  K  V  I  I  E  V  N  T  A  P  S  F  E  G  I
                  <------------------- 30 -------------------->

568  CACGATATAGACATGCCCGTGAACCCACCTTTCAGGAAACCATACCCATATCTGAAAGTG

190   H  D  I  D  M  P  V  N  P  P  F  R  K  P  Y  P  Y  L  K  V
                                        <------ 5-2 ------>  <--

628  GACGACAAGTGTGGTGTTGACTCCATCCCGGTTGATCCTGAAAAGGTTGTTGCGATTGTG
210   D  D  K  C  G  V  D  S  I  P  V  D  P  E  K  V  V  A  I  V
      ---- 13-1 ------------------------>          <--------- 10-2

688  GAGTCCACCATGAGGGACCAGGTCCCACCAAATACGCCCTCTGACGACATGTCCAGGGCT
230   E  S  T  M  R  D  Q  V  P  P  N  T  P  S  D  D  M  S  R  A
      ------------->  <------------------ 6-1 ----------------->  <--

748  ATTGCAGGTCATTTGGTCGAGTTTTTCAGAAACGAGGTAAAACATGGTAGGCTACCTGAA
250   I  A  G  H  L  V  E  F  F  R  N  E  V  K  H  G  R  L  P  E
      --------- 21 ---------------->                <------------------

808  AACCTGCTGCCTTTACAAAGTGGTATAGGTAACATTGCTAACGCTGTCATTGAAGGGCTT
270   N  L  L  P  L  Q  S  G  I  G  N  I  A  N  A  V  I  E  G  L
      - 39 -------------------->
```

FIG.7D

```
 868  GCTGGCGCCCAATTCAAGCACTTGACTGTATGGACGGAAGTGCTGCAGGACTCGTTATTG
 290   A  G  A  Q  F  K  H  L  T  V  W  T  E  V  L  Q  D  S  L  L
                       <-------------- 42 --------------->

928  GATCTTTTCGAGAACGGATCTTTGGACTACTCCACTGCTACTTCCGTGAGATTGACTGAA
 310   D  L  F  E  N  G  S  L  D  Y  S  T  A  T  S  V  R  L  T  E
                *

988  AAGGGTTTCGACAGAGCCTTTGCAAACTGGGAAAATTTCAAACACAGATTGTGTTTGAGA
 330   K  G  F  D  R  A  F  A  N  W  E  N  F  K  H  R  L  C  L  R

1048  TCTCAAGTTGTCTCGAACAATCCGGAAATGATCCGTAGATTCCCTGTCATCGCCATGAAT
 350   S  Q  V  V  S  N  N  P  E  M  I  R  R  F  P  V  I  A  M  N
                       <-------------- 8-1 --------------->

1108  ACCCCAGTAGAAGTTGACATTTACGCGCACGCCAATTCTACAAATGTGAATGGTTCCCGT
 370   T  P  V  E  V  D  I  Y  A  H  A  N  S  T  N  V  N  G  S  R

1168  ATGTTGAACGGGTTGGGTGGATCTGCTGATTTCTTGAGAAATGCAAAGTTGTCCATCATG
 390   M  L  N  G  L  G  G  S  A  D  F  L  R  N  A  K  L  S  I  M
                                                            <-----------

1228  CATGCCCCCTCTGCAAGACCAACTAAAGTAGACCCTACCGGTATCTCTACCATTGTTCCT
 410   H  A  P  S  A  R  P  T  K  V  D  P  T  G  I  S  T  I  V  P
      --- 9-1 ---------------->  <------------------------- 36 ---

1288  ATGGCCTCTCATGTAGATCAAACTGAGCATGACCTGGACATCTTGGTCACTGACCAAGGT
 430   M  A  S  H  V  D  Q  T  E  H  D  L  D  I  L  V  T  D  Q  G
      ----------------------->

1348  TTGGCGGATCTAAGAGGTCTATCGCCTAAGGAAAGAGCCCGTGAAATCATCAACAAGTGT
 450   L  A  D  L  R  G  L  S  P  K  E  R  A  R  E  I  I  N  K  C
                                                                <--

1408  GCTCATCCCGATTATCAAGCTTTGTTGACCGATTACTTGGACAGAGCAGAGCATTACGCT
 470   A  H  P  D  Y  Q  A  L  L  T  D  Y  L  D  R  A  E  H  Y  A
      ----- 26-1 -------------->

1468  AAAAAGCACAATTGCTTGCATGAACCACACATGCTAAAGAATGCTTTCAAGTTCCACACC
 490   K  K  H  N  C  L  H  E  P  H  M  L  K  N  A  F  K  F  H  T
```

FIG. 7E

1528 AACTTAGCTGAAAAGGGTACAATGAAGGTCGACAGCTGGGAACCAGTTGACTAGTGTTTG
 510 N  L  A  E  K  G  T  M  K  V  D  S  W  E  P  V  D  End

1588 TGCGCAAACCGAGAGATGAGTATTTAACAAAAAAAAGAAAGGAAATGATATGATTATGAT

1648 TTTATGTTTATAAAGCTTTTATCCAATGCGTTGTTTTTTCTTGCATATTTATACCTTTTG

1708 CGCTCATGGAGGGAGTTAATCAATACGCATGACGTCTAGTTAATTCACAGGTAGTACTGT

1768 ATATTTATATGTTTACACAATAATTATGTATTAAGTAGTGATTAGTAAAAAAAACTAAGA

1828 GGTTGAAAGTCATCAACCCTTATATT

FIG.7F

-1236  ATAACTCCAACTGTGACTTGAAATATGTGATTCGGTTAGCAAGAATCATTGACGAGTCAG

-1176  CCGCGGACAATTCAGAGCCCACAGGTCAGCAAAGCGGCATGACCGAGTATGTGGCCACAC

-1116  GTTGGTACAGGGCGCCAGAGGTGATGTTAACCTCTGCCAAATACTCAAGGGCCATGGACG

-1056  TGTGGCTGCGGATGTATTCTCGCTGAACTTTTCTTAAGACGGCCAATCTTCCCTGGCAGA

-996   GATTATCGCCATCAACTACTACTGATATTCGGTATCATCGGTACACCTCACTCAGATAAT

-936   GATTTGCGGTGTATAGAGTCACCCAGGGCTAGAGAGTACATAAAGTCGCTTCCCATGTAC

-876   CCTGCCGCGCCACTGGAGAAGATGTTCCTCGAGTCAACCCGAAAGGCCAATAGATCTTTT

-816   ACAGCGTATGCTTGTTTTTGACCCTGCGAAGAGGATTACTGCTAAGGAGGCACTGGAGCA

-756   TCCGTATTTGCAGACATACCACGATCCAAATGACGAACCTGAAGGCGAACCCATCCCACC

-696   CAGCTTCTTCGAGTTTGATCACCACAAGGAGGCACTAACGACGAAAGACCTCAAGAAACT

-636   CATTTGGAACGAAATATTTAGTTAGCCATCATTATCATTAAAATATCAACCCGAAGAACA

-576   ATAATGTATACATATACATATACGTACACATATACATATGTACATATGACATACGTATTA

-516   GCCGCTGAGGACGCGGACGTATAAAAGGACAATACTTATATGGAGCTAAGGGGAGCAGTC

-456   ACGCAACTCCGTGATCGCGCGCCACGGGCCGTCGGCGGCTGTTAATTGAAGAAAAAAAAA

-396   ATGAAGAACCACAAGGGGTGATCCATATAGGTGACTAGCATCATCCCCTGCGACGCGCGG

-336   CCCGCCGGGCAAAGGCGGGCAATGCGCGCTGCTGATTGGCCTCGAGGACAACGCCCTCAA

-276   CCACATCCGCAACAGCCAATCCCATCGGAGCGTCAAACTACCAAAGTAGTGATTGTATGG

-216   ATCACCACTGTATTGTGGACGGTAAGCGCTTGCTGGAGCAAATGTGTAATCAAGTTGCTG

-156   TGTATATATAGACGTTAGATGTGTTCTACCCCTTCTTTTGTCTTGTGCCCACCGGGCTTA

-96    CATTAGCACACAAAGCAGCAAGAGACCGTCTTACTAGACAATAGCGGCAAAACAAACAAC

FIG.10A

```
-36   ACATTTCTTTTTTTCTTTTTCACATATTGCACTAAAATGACAATTTCTAATTTGTTAAAG
                                              M  T  I  S  N  L  L  K

25   CAGAGAGTTAGGTATGCTCCCTATCTGAAAAAAGTTAAGGAAGCTCACGAGCTTATTCCA
  9   Q  R  V  R  Y  A  P  Y  L  K  K  V  K  E  A  H  E  L  I  P

85   TTGTTCAAGAATGGTCAGTACCTTGGGTGGTCCGGTTTTACAGGAGTGGGTACTCCCAAG
 29   L  F  K  N  G  Q  Y  L  G  W  S  G  F  T  G  V  G  T  P  K

145   GCAGTGCCGGAGGCACTGATAGATCACGTGGAGAAGAACAATTTACAAGGGAAGTTGAGA
 49   A  V  P  E  A  L  I  D  H  V  E  K  N  N  L  Q  G  K  L  R

205   TTCAACCTTTTTGTTGGAGCTTCTGCTGGTCCAGAGGAAAACCGTTGGGCTGAACACGAC
 69   F  N  L  F  V  G  A  S  A  G  P  E  E  N  R  W  A  E  H  D
          ---------------- 19-1 -------------------->
      <---
265   ATGATCATTAAGAGAGCCCCTCATCAAGTAGGGAAACCCATTGCAAAGGCAATTAACCAG
 89   M  I  I  K  R  A  P  H  Q  V  G  K  P  I  A  K  A  I  N  Q
                  <------ 1-2 ------>

325   GGTAGAATTGAGTTCTTTGATAAACATCTGTCCATGTTCCCTCAGGATCTGACATACGGG
109   G  R  I  E  F  F  D  K  H  L  S  M  F  P  Q  D  L  T  Y  G
                  <-------------------------------- 35 -------------------

385   TTCTACACCAGGGAAAGAAAAGACAACAAAATCCTTGATTATACTATAATCGAGGCAACG
129   F  Y  T  R  E  R  K  D  N  K  I  L  D  Y  T  I  I  E  A  T
      --------->                      <-------------------------- 34

445   GCCATTAAAGAGGACGGGTCTATCGTCCCAGGTCCCTCTGTCGGTGGTTCTCCAGAATTC
149   A  I  K  E  D  G  S  I  V  P  G  P  S  V  G  G  S  P  E  F

----------------------------------->

505   ATTACAGTCAGTGATAAAGTGATTATTGAGGTTAACACGGCTACGCCTTCGTTCGAGGGT
169   I  T  V  S  D  K  V  I  I  E  V  N  T  A  T  P  S  F  E  G
                        <----------------- 30 ------------------
```

FIG.10B

```
565  ATTCACGATATAGACATGCCCGTGAACCCACCTTTCAGGAAACCATACCCATATCTGAAA
189  I  H  D  I  D  M  P  V  N  P  P  F  R  K  P  Y  P  Y  L  K
     ->                                        <------- 5-2 ----->

625  GTGGACGACAAGTGTGGTGTTGACTCCATCCCGGTTGATCCTGAAAAGGTTGTTGCGATT
209  V  D  D  K  C  G  V  D  S  I  P  V  D  P  E  K  V  V  A  I
     <------- 13-1 ----------------------->        <----------

685  GTGGAGTCCACCATGAGGGACCAGGTCCCACCAAATACGCCCTCTGACGACATGTCCAGG
229  V  E  S  T  M  R  D  Q  V  P  P  N  T  P  S  D  D  M  S  R
     10-2 ----------->   <--------------- 6-1 ----------------->

745  GCTATTGCAGGTCATTTGGTCGAGTTTTTCAGAAACGAGGTAAAACATGGTAGGCTACCT
249  A  I  A  G  H  L  V  E  F  F  R  N  E  V  K  H  G  R  L  P
     <----------- 21 --------------->              <---------------

805  GAAAACCTGCTGCCTTTACAAAGTGGTATAGGTAACATTGCTAACGCTGTCATTGAAGGG
269  E  N  L  L  P  L  Q  S  G  I  G  N  I  A  N  A  V  I  E  G
     ------ 39 -------------------->

865  CTTGCTGGCGCCCAATTCAAGCACTTGACTGTATGGACGGAAGTGCTGCAGGACTCGTTA
289  L  A  G  A  Q  F  K  H  L  T  V  W  T  E  V  L  Q  D  S  L
                         <--------------- 42 --------------->

925  TTGGATCTTTTCGAGAACGGATCTTTGGACTACTCCACTGCTACTTCCGTGAGATTGACT
309  L  D  L  F  E  N  G  S  L  D  Y  S  T  A  T  S  V  R  L  T
                   *

985  GAAAAGGGTTTCGACAGAGCCTTTGCAAACTGGGAAAATTTCAAACACAGATTGTGTTTG
329  E  K  G  F  D  R  A  F  A  N  W  E  N  F  K  H  R  L  C  L

1045 AGATCTCAAGTTGTCTCGAACAATCCGGAAATGATCCGTAGATTCCCTGTCATCGCCATG
349  R  S  Q  V  V  S  N  N  P  E  M  I  R  R  F  P  V  I  A  M
              <-------------- 8-1 --------------->

1105 AATACCCCAGTAGAAGTTGACATTTACGCGCACGCCAATTCTACAAATGTGAATGGTTCC
369  N  T  P  V  E  V  D  I  Y  A  H  A  N  S  T  N  V  N  G  S
                                      *        *

1165 CGTATGTTGAACGGGTTGGGTGGATCTGCTGATTTCTTGAGAAATGCAAAGTTGTCCATC
389  R  M  L  N  G  L  G  G  S  A  D  F  L  R  N  A  K  L  S  I
                                                       <--------
```

FIG.10C

```
1225  ATGCATGCCCCTCTGCAAGACCAACTAAAGTAGACCCTACCGGTATCTCTACCATTGTT
 409   M  H  A  P  S  A  R  P  T  K  V  D  P  T  G  I  S  T  I  V
      ------- 9-1 ---------------->   <---------------------- 36 -

1285  CCTATGGCCTCTCATGTAGATCAAACTGAGCATGACCTGGACATCTTGGTCACTGACCAA
 429   P  M  A  S  H  V  D  Q  T  E  H  D  L  D  I  L  V  T  D  Q
      ------------------------->

1345  GGTTTGGCGGATCTAAGAGGTCTATCGCCTAAGGAAAGAGCCCGTGAAATCATCAACAAG
 449   G  L  A  D  L  R  G  L  S  P  K  E  R  A  R  E  I  I  N  K

1405  TGTGCTCATCCCGATTATCAAGCTTTGTTGACCGATTACTTGGACAGAGCAGAGCATTAC
 469   C  A  H  P  D  Y  Q  A  L  L  T  D  Y  L  D  R  A  E  H  Y
      <-------- 26-1 ------------>

1465  GCTAAAAAGCACAATTGCTTGCATGAACCACACATGCTAAAGAATGCTTTCAAGTTCCAC
 489   A  K  K  H  N  C  L  H  E  P  H  M  L  K  N  A  F  K  F  H

1525  ACCAACTTAGCTGAAAAGGGTACAATGAAGGTCGACAGCTGGGAACCAGTTGACTAGTGT
 509   T  N  L  A  E  K  G  T  M  K  V  D  S  W  E  P  V  D End

1585  TTGTGCGCAAACCGAGAGATGAGTATTTAACAAAAAAAAGAAAGGAAATGATATGATTAT

1645  GATTTTATGTTTATAAAGCTTTTATCCAATGCGTTGTTTTTTCTTGCATATTTATACCTT

1705  TTGCGCTCATGGAGGGAGTTAATCAATACGCATGACGTCTAGTTAATTCACAGGTAGTAC

1765  TGTATATTTATATGTTTACACAATAATTATGTATTAAGTAGTGATTAGTAAAAAAAACTA

1825  AGAGGTTGAAAGTCATCAACCCTTATATT
```

FIG. 10D

| Deletion Mutants | β-GALACTOSIDASE ACTIVITY (μmol/min/mg) | | |
|---|---|---|---|
| | Glucose | Glycerol | Galactose |
| Vector-SmaI-SalI-(-849)XhoI-(-296)XhoI-Vector BglII/BamHI | 0.1 | 4.9 | 2.7 |
| SmaI, -790, Vector BglII/BamHI | 0.1 | 22.0 | 8 |
| SmaI, -477 | 0.12 | 14.9 | 9.2 |
| SmaI, -475 | 0.09 | 62.0 | 8.0 |
| SmaI, -468 | 0.11 | 60.0 | 28.4 |
| SmaI, -432 | 0.22 | 67.3 | 34.4 |
| SmaI, (-296)XhoI | 0 | 0 | 0 |

FIG. 12

```
                                                        AGGGGAGCAGTCACG

-453   CAACTCCGTGATCGCGCGCCACGGGCCGTCGGCGGCTGTTAATTGAAGAAAAAAAAAATG

-393   AAGAACCACAAGGGGTGATCCATATAGGTGACTAGCATCATCCCCTGCGACGCGCGGCCC

-333   GCCGGGCAAAGGCGGGCAATGCGCGCTGCTGATTGGCC
```

FIG. 13

GLUCOSE-REGULATED PROMOTER OF YEAST ACETYL-COA HYDROLASE

CROSS-REFERENCE TO RELATED APPLICATIONS

This application is a continuation-in-part of U.S. patent application No. 07/480,452 (filed Feb. 15, 1990) now abandoned, which is a continuation-in-part of U.S. patent application Nos. 07/213,943 (filed: Jul. 1, 1988) now abandoned, and 07/297,003 (filed: Jan. 13, 1989) now abandoned.

FIELD OF THE INVENTION

This invention is in the field of molecular biology and is directed to the glucose-regulated promoter associated with the yeast acetyl-CoA hydrolase gene and the expression of heterologous genes from such promoter.

BACKGROUND OF THE INVENTION

Acetyl-CoA: Although acetyl-CoA is mainly oxidized in the Krebs cycle or convened to fatty acids or ketone bodies, a varying percentage can be used as a substrate in co-translational, post-translational, or chemical modification acetylation. The covalent attachment of acetyl groups to biological substances is a common chemical modification in biological systems (Tsunasawa, S., et al., *Methods Enzymol.* 106:165–170 (1984); Driessen, H. P. C., et al., *CRC Crit. Rev. Biochem.* 18:281–325 (1985); Klein, U., et al., *Proc. Natl. Acad. Sci. U.S.A.* 75:5185–5189 (1978); Roskoski, R., Jr., *J. Biol. Chem.* 249:2156–2159 (1974); Jencks, W. P, et al., *J. Biol. Chem.* 247:3756–3760 (1972); Deguchi, T., et al., *J. Biol. Chem.* 263:7528–7533 (1988)). Acetylation is mediated by acetyltransferases, which catalyze the transfer of acetyl groups from acetyl coenzyme A to the —$NH_2$ groups or —OH groups of biological molecules.

The concentration of acetyl-CoA in cells is regulated by its rate of synthesis and its rate of utilization and degradation. Acetyl-CoA is primarily synthesized from pyruvate generated from carbohydrates and amino acids (Ala, Thr, Gly, Ser, and Cys), from acetoacetyl-CoA generated from other amino acids (Phe, Tyr, Leu, Lys, and Trp), and from the β-oxidation of fatty acids. A minor amount is synthesized by acetyl-CoA synthetase (Frenkel, E. P. et al., *J. Biol. Chem.* 252:504–507 (1977)). Acetyl-CoA may be used in the Krebs cycle or converted to fatty acids or ketone bodies. The acetyltransferase-catalyzed acetylation of proteins and peptides (Tsunasawa, S. et al., *Methods Enzymol.* 106:165–170 (1984); Driessen, H. P. C. et al., *CRC Crit. Rev. Biochem.* 18:281–325 (1985); Persson, B. et al., *Eur. J. Biochem.* 152:523–527 (1985); Augen, J. et al., *Trends Biochem. Sci.* 11:494–497 (1986); Allfrey, V. G. et al., *Methods Enzymol.* 107:224–240 (1984); Rudman, D. et al., *J. Biol. Chem.* 254:10102–10108 (1979)), as well as of biological substances other than proteins (e.g., glucosamine, choline, arylamine, arylalkylamine) (Klein, U. et al., *Proc. Natl. Acad. Sci. USA* 75:5185–5189 (1978); Roskoski, R., Jr., *J. Biol. Chem.* 249:2156–2159 (1974); Jencks, W. P. et al., *J. Biol. Chem.* 247:3756–3760 (1972); Weber, W. W. et al., *Pharmacol. Rev.* 37:25–79 (1985)) accounts for additional usage of endogenous acetyl-CoA.

Acetyl-CoA Hydrolase: Acetyl-CoA hydrolase (EC 3.1.2.1) hydrolyzes acetyl-CoA to acetate and CoA. This enzyme was first identified in pig heart in 1952 (Gergely, J., et al., *J. Biol. Chem.* 263:313–319 (1952)) and has subsequently been found in many mammalian tissues (Knowles, S. E., et al., *Biochem. J.* 142:401–411 (1974); Robinson, J. B., et al., *Biochem. Biophys. Res. Commun.* 71:959–965 (1976); Bernson, V. M. S., *Eur. J. Biochem.* 67:403–410 (1976); Grigat, K. P., et al., *Biochem. J.* 177:71–79 (1979); Prass, R. L., et al., *J. Biol. Chem.* 255:5215–5223 (1980); Soling, H. D., et al., *Eur. J. Biochem.* 147:111–117 (1985)). In rat liver, two isoenzymes of acetyl-CoA hydrolase have been found. One is located in the matrix space of mitochondria (Soling, H. D., et al., *Eur. J. Biochem.* 147:111–117 (1985)) and the other in the cytoplasm (Prass, R. L., et al., *J. Biol. Chem.* 255:5215–5223 (1980)). Although only the rat liver cytoplasmic enzyme has been purified to homogeneity (Prass, R. L. et al., *J. Biol. Chem.* 255:5215– 5223 (1980)), the rat brain mitochondrial enzyme has also been partially purified and characterized (Robinson, J. B. et al., *Biochem. Biophys. Res. Commun.* 71:959–965 (1976)). The soluble cytosolic acetyl-CoA hydrolase found in rat liver is cold labile, inhibited by 5'ADP and activated by 5'ATP (Prass, R. L., et al., *J. Biol. Chem.* 255:5215–5223 (1980)). In contrast, the mitochondrial acetyl-CoA hydrolase is not affected by cold temperature (4° C.), ADP or ATP (Soling, H. D., et al., *Eur. J. Biochem.* 147:111–117 (1985)). CoASH is a strong product inhibitor of the cold-labile enzyme, but only a weak inhibitor of the mitochondrial enzyme (Soling, H. D., et al., *Eur. J. Biochem.* 14 7:111–117 (1985)).

Although there have been many studies on the physicochemical properties of acetyl-CoA hydrolase, little is known about its biological functions. It has been proposed that the enzyme may play a role in maintaining cytosolic acetyl-CoA and CoASH concentrations for both fatty acid synthesis and oxidation (Prass, R. L. et al., *J. Biol. Chem.* 255:5215–5223 (1980)). Bernson (*Eur. J. Biochem.* 67:403–410 (1976)) has suggested that the enzyme in hamster brown adipose may be involved in the post-hibernation warming-up process. In addition, it has been suggested (Namboodiri, M. A. A. et al., *J. Biol. Chem.* 255:6032–6035 (1980)) that arylalkylamine N-acetyltransferase in the rat pineal gland plays a key role in maintaining the circadian rhythms associated with melatonin synthesis and that acetyl-CoA hydrolase may also play a role in this process.

Acetyl-CoA hydrolase has been found to be an inhibitor of purified rat brain pyruvate carboxylase (Mahan, D. E., et al., *Biochem. J.* 145:25–35 (1974)) and choline acetyltransferase (Severin, S. E., et al., *Biokhimia* 32: 125– 131 (1967)). It is also suspected of being an inhibitor of the acetyltransferase found in pituitary homogenates (Glembotski, C. C., *J. Biol. Chem.* 257: 10501– 10509 (1982)) and in crude yeast lysates (Travis, G. H., et al., *J. Biol. Chem.* 259:14406–14412 (1984); Dixon, J. E., et al., *Methods Enzymol.* 106:170–179 (1984)). In addition, acetyl-CoA hydrolase has been found to inhibit purified rat brain pyruvate carboxylase (Mahan, D. E. et al., *Biochem. J.* 145:25–35 (1975)), choline acetyltransferase (Severin, S. E. et al., *Biokhimia* 32:125–131 (1967)), and [acyl-carrier-protein] acetyltransferase (Lowe, P. N. et al., *Biochem. J.* 250:789–796 (1988)).

SUMMARY OF THE INVENTION

The invention is directed to the yeast acetyl-CoA hydrolase glucose-repressible promoter. The promoter comprises a sequence element lying between nucleotide -296 and nucleotide -468 of the yeast acetyl-CoA hydrolase gene wherein nucleotide -1 is immediately adjacent and 5 prime to the "A" of the "ATG" translation initiation site and nucleotides are numbered in an increasingly negative manner in the 5 prime direction.

In addition, the invention is directed to vectors incorporating the glucose-repressible promoter, to host cells that have been transformed with such vectors and to methods of synthesizing heterologous proteins therefrom.

BRIEF DESCRIPTION OF THE FIGURES

FIG. 5(A) The activity of yeast acetyl-CoA hydrolase was determined at different temperatures by the radioactive assay, as described below in Example 1. FIG. 5(B) The activity of yeast acetyl-CoA hydrolase in the radioactivity assay was determined at different pHs using 100 mM buffers of sodium acetate, citrate-phosphate, potassium phosphate, and CHES.

FIG. 7A–7C shows the probes used in cloning acetyl-CoA hydrolase and the sequence of the cDNA. (FIG. 7A) Oligonucleotide probes used for screening the λgt11 library. The amino acid sequences of two tryptic peptides (SEQ. ID Nos. 1 and 3) were used to construct oligonucleotide probes (SEQ. ID Nos. 2 and 4) based upon the frequency of codon-usage. The nucleotide positions indicated by the asterisks differ from the actual DNA sequence shown in C. The numbering of the tryptic peptides is as follows: the first number refers to the corresponding peak in FIG. 1, the second number refers to the peak in the first isocratic HPLC separation. (FIG. 7B) Restriction map and DNA sequencing strategy for the cDNA clones. The arrows indicate the direction and extent of sequence determination for each fragment after exonuclease III deletion. (FIG. 7C–7G) Nucleotide (SEQ. ID No. 5) and deduced amino acid sequence (SEQ. ID 6) of acetyl-CoA hydrolase cDNA clones. The protein sequence analyses were completed with repetitive yields between 84% and 96% for 100–200 pmol of each peptide. Abbreviations: E, EcoRI; H, HindIII; P, PstI; S, SalI; X, XhoI.

FIG. 10A–10E shows the genomic nucleotide (SEQ. ID 7) and deduced amino acid sequence (SEQ. ID 8) of the acetyl-CoA hydrolase gene.

FIG. 12 shows the amount of β-galactosidase activity present in extracts of yeast cells. Cells had been transformed with plasmids in which the lacZ gene was placed downstream from a series of DNA fragments containing a variable amount of genomic sequence 5 prime of the acetyl-CoA hydrolase gene. Yeast were grown in either the presence of glucose, galactose or glycerol.

FIG. 13 shows the nucleotides -296 to -468 (SEQ ID No. 11) from the yeast acetyl-CoA hydrolase gene. This region is responsible for the glucose-repressible expression of the gene.

DETAILED DESCRIPTION OF THE INVENTION

Definitions

Figure 1:
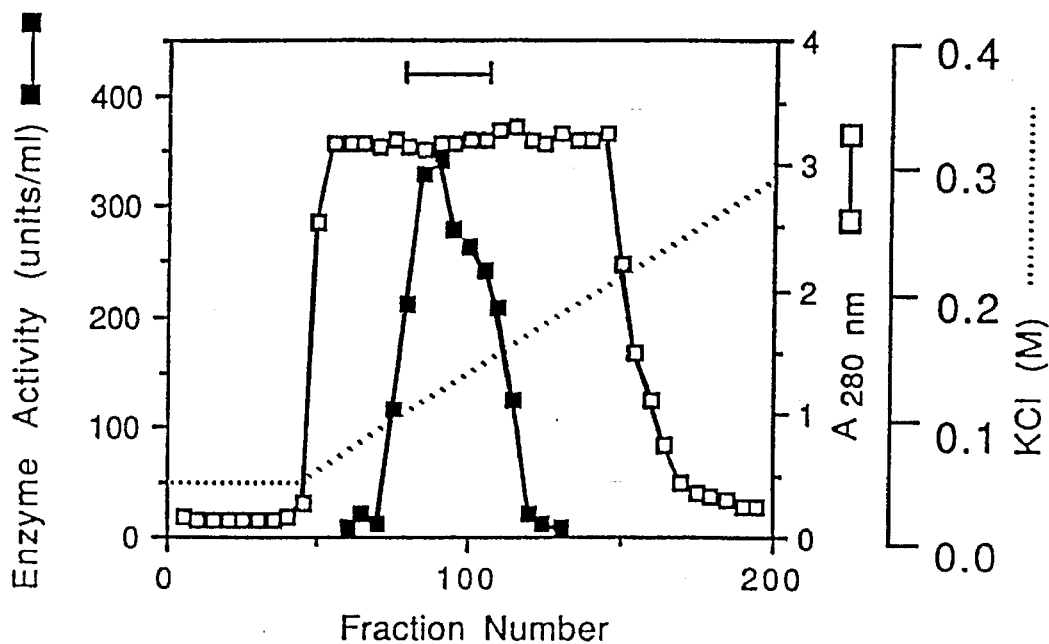
FIG. 1 shows the elution profile of yeast acetyl-CoA hydrolase chromatographed on DEAE-Sepharose. Crude yeast lysates containing acetyl-CoA hydrolase were concentrated, dialyzed, and applied to a DEAE-Sepharose column. The column was eluted with a linear gradient of 0.05 M (250 ml) to 0.5 M (250 ml) KCl in HDG buffer (20 mM HEPES, pH 7.4, 0.5 mM DTT, 10% glycerol, 0.02% $NAN_3$) at 24 ml/h. Fractions were collected and analyzed for absorbance at 280 nm and for enzyme activity in the acetylation inhibition assay. Fractions containing acetyl-CoA hydrolase activity were pooled as indicated by the horizontal bar.

Promoter: The term "promoter" as used herein refers to a sequence of nucleotides which, at a minimum, enhances the transcription of one or more operably-linked DNA sequence elements. Promoters may respond to external conditions, e.g. changes in temperature or the concentration of some factor, by increasing or decreasing the rate at which operably-linked elements are transcribed. When a promoter increases the rate of transcription in response to a factor it is said to be "inducible". When a promoter decreases the rate of transcription in response to a particular factor, it is said to be "repressible".

Operable linkage: An "operable linkage" is a linkage in which a sequence is connected to another sequence (or sequences) in such a way as to be capable of altering the functioning of the sequence (or sequences). For example, a protein-encoding sequence which is operably linked to the glucose-repressible promoter of the present invention places expression of the protein-encoding sequence under the influence or control of the promoter. Two DNA sequences (such as a protein-encoding sequence and a promoter region sequence linked to the 5' end of the protein-encoding sequence) are said to be operably linked if induction of promoter function results in the transcription of the protein-encoding sequence mRNA and if the nature of the linkage between the two DNA sequences does not (1) result in the introduction of a frame-shift mutation, (2) interfere with the ability of the expression regulatory sequences to direct the expression of the mRNA or protein. Thus, a promoter region would be operably linked to a DNA sequence if the promoter were capable of effecting transcription of that DNA sequence.

Cloning vector: A "cloning vector" is a plasmid, phage or other DNA sequence which is characterized by one or a small number of endonuclease recognition sites at which such DNA sequences may be cut in a determinable fashion without loss of an essential biological function of the vector, and into which DNA may be spliced in order to bring about its replication and cloning. The cloning vector may further contain a marker suitable for use in the identification of cells transformed with the cloning vector. Markers, for example, are erythromycin and kanamycin resistance. The term "vehicle" is sometimes used for "vector."

Expression vector: An "expression vector" is similar to a cloning vector but is capable of transcribing a recombinant DNA sequence element, e.g. transcribing the mRNA for a structural gene which has been cloned into the vector, after transformation of the vector into a host. In an expression vector, the cloned DNA sequence is placed under the control of (i.e. operably linked to) certain control sequences, e.g. the glucose-repressible promoter of the present invention, which allow such DNA to be expressed in a specific host. Expression control sequences will vary, and may include transcriptional elements such as enhancer or termination sequences and/or translational elements such as initiation and termination sites.

Expressed protein: When a protein is referred to as being "expressed", this indicates that the DNA sequence encoding the protein has been both transcribed and translated.

Fragment: A "fragment" of a molecule such as a nucleic acid or protein is meant to refer to a molecule which contains a portion of the complete sequence of the native molecule.

Mutant: A "mutant" is a biological entity which has undergone either natural or manmade alterations which distinguish it from its unaltered counterpart. A "deletion mutant" as used herein refers to a cloned DNA sequence which has been altered by having nucleotides deleted from either its 5' or 3' end.

Purification and Characterization of the Acetyl-CoA Enzyme and Cloning of the Acetyl-CoA cDNA Acetyl-CoA hydrolase is an enzyme which hydrolyzes acetyl-CoA to acetate and coenzyme A (CoA). During the purification of yeast $N^{\alpha}$-acetyltransferase, the inventors detected the presence of an endogenous inhibitor of acetyltransferase as evidenced by a 204% recovery of enzyme activity after DEAE-Sepharose chromatography (Lee, F.-J.S., et al., *J. Biol. Chem.* 263:14948–14955 (1988), herein incorporated by reference). The inhibitor was purified and shown to be acetyl-CoA hydrolase (Lee, F.-J.S., et al., *Eur. J. Biochem.* 184:21–28 (1989), herein incorporated by reference).

Acetyl-CoA hydrolase was isolated from *Saccharomyces cerevisiae* and demonstrated to be $NH_2$-terminally blocked. The enzyme was purified 2400-fold to apparent homogeneity by successive purification steps using DEAE-Sepharose, gel filtration, and hydroxyapatite (Example 1).

The $M_r$ of native yeast acetyl-CoA hydrolase was estimated to be 64,000±5,000 by gel filtration chromatography. SDS-PAGE analysis revealed that the denatured molecular weight was 65,000±2,000 (Lee, F.-J.S., et al., *Eur. J. Biochem.* 184:21–28 (1989)). Together the results indicate that yeast acetyl-CoA hydrolase is monomeric. The enzyme had a pH optimum near 8.0, and a pI of approximately 5.8. During the purification, it was noticed that the enzymatic activity and yield were higher from stationary phase or frozen cells than from cells in log phase or from freshly cultured cells.

Several acyl-CoA derivatives of varying chain length were tested for their ability to serve as substrates for yeast acetyl-CoA hydrolase. Although the enzyme was relatively specific for acetyl-CoA, longer acyl-chain CoAs were also hydrolyzed and were capable of functioning as inhibitors of the hydrolysis of acetyl-CoA. Among divalent cations, $Zn^{2+}$ was demonstrated to be the most potent inhibitor. The enzyme was inactivated by chemical modification with diethyl pyrocarbonate, a histidine-modifying reagent.

The cDNA for the acetyl-CoA hydrolase gene was cloned and was found to exhibit glucose-repressible expression (Examples 2 and 3).

Comparison of Yeast Acetyl-CoA Hydrolase with Previously Described Enzymes

Although others have attempted to isolate acetyl-CoA hydrolase from a variety of sources, only the cytosolic enzyme from rat liver has been previously purified (Prass, R. L., et al., *J. Biol. Chem.* 255:5215–5223 (1980). As described above, the native yeast enzyme is monomeric and has a molecular weight of 64,000±5,000 as determined by gel filtration chromatography, and 65,000±2,000 as determined by SDS-PAGE. The native rat liver cytosolic enzyme was reported to be polymeric and to have a molecular weight of between 240,000 and 340,000 (Prass et al., *J. Biol. Chem.* 255:5215–5223 (1980). The $M_r$ of the native enzyme from rat brain (Robinson, J. B. et al., *Biochem. Biophys. Res. Commun.* 71:959–965 (1976)) and the native mitochondrial enzyme from rat liver (Soling, H. D. et al., *Eur. J. Biochem.* 147:111–117 (1985)) were found to be 150,000 and 157,000 respectively. The pH optimum for yeast and rat brain mitochondrial acetyl-CoA hydrolase are identical (pH≈8) (Robinson, J. B. et al., *Biochem. Biophys. Res. Commun.* 71:959–965 (1976)).

Two different acetyl-CoA hydrolases have been identified in rat liver. One is located in the cytoplasm and the other is in the mitochondrial matrix. The cytoplasmic enzyme is cold labile, inhibited by CoASH, ADP and GDP, and activated by ATP (Prass, R. L. et al., *J. Biol. Chem.* 255:5215–5223 (1980); Soling, H. D. et al., *Eur. J. Biochem.* 147:111–117 (1985)). The mitochondrial enzyme is not affected by cold, only weakly inhibited by CoASH, not inhibited by ADP or GDP, and not activated by ATP. In addition, the mitochondrial enzyme has been found to be inhibited by NADH (Bernson, V. S. M., *Eur. J. Biochem.* 67:403–410 (1976); Soling, H. D. et al., *Eur. J. Biochem.* 147:111–117 (1985)).

Yeast acetyl-CoA hydrolase resembles the mitochondrial enzyme in that it is not cold sensitive, only weakly inhibited by CoASH, not affected by ADP or ATP, and inhibited by βNADH (Table 3). The $K_m$ of yeast acetyl-CoA hydrolase is similar to the mitochondrial enzyme from hamster brown fat (Bernson, V. S. M., *Eur. J. Biochem.* 67:403–410 (1976)) (62 μM and 51 μM, respectively). Uses of Acetyl-CoA hydrolase are described in Example 4.

The Glucose-Repressible Promoter and Its Uses

Based upon the results discussed in Examples 5 and 6, the present invention is directed to the glucose-repressible promoter of the yeast acetyl-CoA hydrolase gene and its uses. The promoter may be obtained as part of a DNA fragment lying 5 prime to the translation initiation site of the acetyl-CoA hydrolase gene. Preferably, the fragment comprises a sequence lying between nucleotide -296 and nucleotide -468 as numbered in FIG. 10 (SEQ. ID No. 7). The main distinguishing characteristic of the sequence is its ability to promote the expression of genes lying 3 prime to it and to respond to the presence of glucose by decreasing the expression of coding sequences operably linked to it (see Examples 5 and 6). The promoter with the above characteristics may also be isolated from other glucose-regulated genes or may be synthesized.

The invention is also directed to vectors comprising the promoter sequence defined above and to host cells transformed by such vectors. Preferably, the promoter regulates the expression of genes incorporated into the same vector in a glucose-repressible manner. For example, cells may be transformed with an expression vector containing a heterologous gene under the control of the promoter and then grown in glucose-containing medium. Little or no expression of the recombinant gene is seen under these conditions. The cells may then be transferred to a medium in which glycerol, galactose or a similar agent is substituted for glucose. This will stimulate heterologous gene expression. The medium containing recombinant protein produced in this manner may be collected and either used directly or subjected to purification steps designed to isolate the protein.

A variety of eukaryotic systems can be used for expressing acetyl-CoA and expression may occur either in vitro or in vivo. It is expected that other elements such as transcription enhancer elements and secretion elements will be incorporated into expression vectors along with the glucose-repressible promoter and the gene for the protein being expressed.

Elements other than a DNA sequence coding for a protein may be placed under the control of the glucose-repressible promoter. For example, the antisense sequence of a particular gene may be place downstream from the promoter. In this embodiment of the invention, growth in glucose inhibits the expression of antisense DNA and therefore permits the expression of the target of the antisense sequence. Maintenance of cells in glucose-free medium promotes the transcription of the antisense DNA and therefore inhibits the expression of its target sequence.

In another embodiment of the invention, the glucose-repressible promoter is placed upstream from a gene on the chromosome of a host cell. This may be accomplished either by linking the promoter directly to the regulated gene so that both are incorporated into the chromosome together or by directing the promoter to a specific site on the chromosome upstream from a particular gene, e.g. by homologous recombination.

Methodology for Expressing Heterologous Proteins Using the Glucose-Repressible Promoter Construction of Vectors DNA sequences encoding proteins whose expression is desired may be derived from either genomic or cDNA clones. The extraction of genomic DNA can be performed by means well-known in the art (for example, see *Guide to Molecular Cloning Techniques*, S. L. Berger et al., eds., Academic Press (1987)).

Alternatively, nucleic acid sequences which encode a desired protein can be obtained by cloning mRNA specific for that protein. mRNA can be isolated from any cell which produces or expresses the protein of interest and used to produce cDNA by means well-known in the art (for example, see *Guide to Molecular Cloning Techniques*, S. L. Berger et al., eds., Academic Press (1987)). Preferably, the mRNA preparation used will be enriched in mRNA coding for the desired protein, either naturally, by isolation from cells which are producing large amounts of the protein, or in vitro, by techniques commonly used to enrich mRNA preparations for specific sequences, such as sucrose gradient centrifugation.

To prepare DNA for cloning into a cloning vector or an expression vector, a suitable DNA preparation (either genomic DNA or cDNA) is randomly sheared or enzymatically cleaved. Such DNA can then be ligated into appropriate vectors to form a recombinant genomic or cDNA library.

A DNA sequence encoding a protein of interest may be inserted into a cloning vector or an expression vector in accordance with conventional techniques, including cleaving DNA so as to form either blunt-end or staggered-end termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., Molecular Cloning (A Laboratory Manual), Cold Spring Harbor Laboratory, 1982), and are well-known in the art.

Libraries may be screened and a desired clone identified by any means which specifically selects for the DNA of interest. For example, if a clone to a desired protein sequence is desired, such a clone may be identified by any means used to identify such protein or mRNA for such protein, including: a) by hybridization with an appropriate nucleic acid probe(s) containing a sequence(s) specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated protein product produced by the host containing the clone.

Oligonucleotide probes specific for a desired protein can be used to identify a desired clone. Such probes can be designed from knowledge of the amino acid sequence of the desired protein. Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). Peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. It is possible to employ the unfractionated set of oligonucleotides in the same manner in which one would employ a single oligonucleotide to clone the gene that encodes the peptide.

Using the genetic code (Watson, J. D., In: *Molecular Biology of the Gene,* 3rd Ed., W. A. Benjamin, Inc., Menlo Park, Calif. (1977)), one or more different oligonucleotides can be identified from the amino acid sequence, each of which would be capable of encoding the desired protein. The probability that a particular oligonucleotide will, in fact, constitute the actual protein's encoding sequence can be estimated by considering the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide sequence, or a set of oligonucleotide sequences, that contain a theoretical "most probable" nucleotide sequence capable of encoding the human secretory granule proteoglycan sequences is identified.

The suitable oligonucleotide, or set of oligonucleotides, which is capable of encoding a fragment of the desired gene (or which is complementary to such an oligonucleotide, or set of oligonucleotides) may be synthesized by means well-known in the art (see, for example, *Synthesis and Application of DNA and RNA,* S. A. Narang, ed., 1987, Academic Press, San Diego, Calif.) and employed as a probe to identify and isolate the cloned gene by techniques known in the art. Techniques of nucleic acid hybridization and clone identification are disclosed by Maniatis, T., et al. (In: *Molecular Cloning, A Laboratory Manual,* Cold Spring Harbor Laboratories, Cold Spring Harbor, N.Y. (1982)), and by Haines, B. D., et al. (In: *Nucleic Acid Hybridization, A Practical Approach,* IRL Press, Washington, D.C. (1985)), which references are herein incorporated by reference. Those members of the above-described gene library which are found to be capable of such hybridization are then analyzed to determine the extent and nature of the sequences which they contain.

To facilitate the detection of the desired encoding sequence, the above-described DNA probe may be labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby, P. J. W., et al., *J. Mol. Biol.* 113:237 (1977) and by T4 DNA polymerase replacement synthesis as described in, for example, Deen, K. C., et al., *Anal. Biochem.* 135:456 (1983).

Alternatively, polynucleotides are also useful as nucleic acid hybridization probes when labeled with a non-radioactive marker such as biotin, an enzyme or a fluorescent group. See, for example, Leary, J. J., et al.; *Proc. Natl. Acad. Sci. USA* 80:4045 (1983); Renz, M., et al., *Nucl. Acids Res.* 12:3435 (1984); and Renz, M., *EMBO J.* 6:817 (1983).

Thus, in summary, the actual identification of peptide sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing a desired protein.

In some instances, probes may not be needed for the cloning of DNA or the screening of libraries. The polymerase chain reaction ("PCR") can often be used to amplify specific regions of DNA provided either DNA or amino acid sequence information is available which can be used for synthesizing appropriate primer oligonucleotides (Sambrook, et al., *Molecular Cloning, A Laboratory Manual,* chapter 14 (1989). It is well-known in the art that PCR practiced in a variety of ways can be used to supplement or replace many of the cloning and characterization steps described above. Id.

Expression of Recombinant Proteins

To express a desired protein, transcriptional and translational signals recognizable by an appropriate host are necessary. Cloned protein-encoding sequences, obtained through the methods described above, and preferably in a double-stranded form, may be operably linked to the glucose-repressible promoter. Such sequences may be introduced into a host cell to produce recombinant protein or a functional derivative thereof.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide. The precise nature of the regulatory regions needed for gene expression may vary between species or cell types, but shall in general include, as necessary, 5' non-transcribing and 5' non-translating (non-coding) sequences involved with initiation of transcription and translation respectively.

If desired, a fusion product of the desired protein may be constructed. For example, the sequence encoding the desired protein may be linked to a signal sequence which will allow secretion of the protein from, or the compartmentalization of the protein in, the host cell. Such signal sequences may be designed with or without specific protease sites such that the signal peptide sequence is amenable to subsequent removal. Alternatively, the native signal sequence for a protein may be used, or a combination of vector and native signal sequences.

To transform a host cell with the DNA constructs of the invention many vector systems are available, depending upon whether it is desired to insert the genetic DNA construct into the host cell chromosomal DNA, or to allow it to exist in an extrachromosomal form.

Vectors may provide a DNA sequence element which promotes integration of DNA sequences in chromosomes. In a preferred embodiment, such DNA sequence element is a sequence homologous to a sequence present in the host chromosome such that the integration is targeted to the locus of the genomic sequence and targets integration at that locus in the host chromosome.

Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or the like. The selectable marker gene can either be directly linked to the DNA gene sequences to be expressed, or introduced into the same cell by co-transformation.

A transformed sequence may also be incorporated into a plasmid or other vector capable of autonomous replication in the recipient host, e.g. bovine papilloma virus vectors.

Factors of importance in selecting a particular vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) is prepared for expression, the DNA construct(s) is introduced into an appropriate host cell by any of a variety of suitable means. After the introduction of the vector, recipient cells are grown in a medium which selects for the growth of vector-containing cells. Expression of the cloned gene sequence(s) results in tile production of the desired protein. This expression can take place in a continuous manner in the transformed cells, or in a controlled manner.

The glucose-repressible promoter of the invention may be operably linked to any coding sequence. For example, the coding sequence of a hormone, structural protein, or growth factor may be used, such as that for fibronectin, insulin, insulinlike growth factor, alveolar marcophage-derived growth factor, laminin, basic fibroblast growth factor, acidic fibroblast growth factor, PDGF, EGF, collagen, thrombospondin, heparin, Transformation growth factor-α, Transformation growth factor-β, int-2, endothelial cell growth factor, heparin-binding growth factor-1, Kaposi sarcoma FDF, Fibroblast growth factor-5, Fibroblast growth factor-6, Hst-1 related gene, keratinocyte growth factor, integrin, anchorin, lipocortin, calpactin, calmodulin. The promoter of the invention may also be operably linked to transcription factors so as to indirectly control the transcription of a different gene that is the target of such transcription factor. Such transcription factors include those transcription factors classified as eukaryotic Helix-turn-helix proteins, the homeodomains (such as MATα2, MATα1, oct-2, unc-86, ubx, eve, ftz, ANtp, and en), zinc finger proteins (such as TFIIIa-1, TFIIIa-2, TFIIIa-3, SP1-1, SP1-2, SP1-3, zif268-1, zif268-2 and zif268 -3), the steroid receptor promins (including receptors for steroid hormones, retinoids, vitamin D, estrogen, androgen, glucocorticoid, progesterone, knirps, nur77 and thyroid hormones), leucine zipper proteins (such as c/EBP, Ig/EBP-1, CREB, c-FOS, c-JUN, GGN4, Opaque2, sis-A, Cys-3), and the helix-loop-helix proteins (such as n-myc, c-myc, myoD, daughterless, e12, e47, T4 achaete-scute and T5 achaete-scute).

The expressed promin may be isolated and purified in accordance with conventional conditions, such as extraction, precipitation, chromatography, affinity chromatography, electrophoresis, or the like.

Having now fully described the invention,, the same will be more readily illustrated by reference to the following examples.

EXAMPLE 1

Purification and Characterization of Acetyl-CoA Hydrolase Activity

Materials and Methods

Materials

The following abbreviations are used herein: A buffer, 50 mM Tris-HCl, pH 7.8, 10 mM $MgCl_2$, 3 mM DTT, 1 M sorbitol; acetyl-CoA, acetyl coenzyme A; B buffer, 10 mM HEPES, pH 7.4, 1.5 mM $MgCl_2$, 10 mM KCl, and 0.5 mM DTF; CHES, 2-(N-cyclohexylamino) ethane-sulfonic acid; CoASH, coenzyme A; DEPC, diethyl pyrocarbonate; HDG buffer, 20 mM HEPES, pH 7.4, 0.5 mM DTT, 10% (v/v) glycerol and 0.02% $NAN_3$; HEPES, N-2-hydroxyethylpiperazine-N'-2-ethanesulfonic acid; $HNBS(CH_3)_2Br$, dimethyl-(2-hydroxy-5-nitrobenzyl)sulfonium bromide; IAA, iodoacetic acid; IAM, iodoacetamide; NBS, N-bromosuccinimide; NEM, N-ethylmaleimide; pCMB, p-chloromercuribenzoate; SDS-PAGE, sodium dodecyl sulfate-polyacryamide gelelectrophoresis; TNBS, 2,4,6-trinitrobenzenesulfonic acid.

NEM, IAA, IAM, $HNBS(CH_3)_2$-Br, TNBS, N-acetylimidazole, pCMB, NBS, DEPC, acetoacetyl-CoA, butyryl-CoA, malonyl-CoA, propionyl-CoA, myristoyl-CoA, HEPES, CAPS, CHES, DTT, hydroxylamine, bovine serum albumin, protein standards for $M_r$ determinations, 2-mercaptoethanol, glucose, sorbitol, lyticase, Bit-Tris, Tris and glycerol (enzyme grade) were from Sigma. DEAE-Sepharose CL-6B, Sepharose CL-4B and chloramphenicol acetyltransferase were from Pharmacia. Protein assay reagent (Bradford method), hydroxylapatite (Biogel HT), Affi-Gel Blue gel and SDS-PAGE electrophoresis reagents were from BioRad. [$^3$H] Acetyl coenzyme A was from Amersham, and unlabeled acetyl coenzyme A was from P-L Biochemicals. Reagents and solvents from amino acid analysis and Ready-Solv EP scintillation cocktails were obtained from Beckman. SP membrane was from Cuno Inc. PM-30 membrane was from Amicon. Yeast extract and Bacto-peptone were from Difco. Constant boiling (6 N) HCl and Polybrene were from Pierce. Phenol was from BRL. Microdialyzer was from Health Products. Reagents and solvents for protein sequence analysis were from Applied Biosystems. Reagents for peptide synthesis were obtained from Applied Biosystems, and solvents for peptide synthesis were from Anachem. Boc-amino acids were from Peninsula. All other chemicals were reagent grade or better.

Methods

General

UV measurements were obtained using a Hewlett-Packard 8450A UV spectrophotometer. Protein assays were performed by the method of Bradford (*Anal. Biochem.* 72:248–254 (1976)) using bovine serum albumin as the standard. Radioactive samples were counted on a Beckman LS 3801 scintillation counter.

Assays for Acetyl-CoA Hydrolase Activity

A. Acetylation Inhibition Assay

The principle of this assay is that acetyl-CoA hydrolase will hydrolyze acetyl-CoA and thereby deplete the amount of acetyl-CoA from which a labeled acetyl group may be transferred by $N^\alpha$-acetyltransferase to ACTH (1– 24). The assay for inhibition of acetylation uses a previously described assay for $N^\alpha$-acetyltransferase (Lee, F.-J.S., et al., *J. Biol. Chem.* 263:14948–14955 (1988)) and is carried out as follows: aliquots of acetyl-CoA hydrolase solutions (2–20 µl) were added to 1.5 ml Eppendorf tubes containing a reaction mixture of 50 mM HEPES, pH 7.4, 150 mM KCl, mM DTT, 50 µM ACTH (1–24), and partially purified yeast $N^\alpha$-acetyltransferase from the hydroxylapatite chromatography step (Lee, F.-J.S., et at., *J. Biol. Chem.* 263:14948–14955 (1988)) (≈10 units) in a final volume of 100 µl. The reaction was initiated by adding 25 µM [$^3$H] acetyl-CoA (0.5 µCi). The assay mixture was incubated at 30° C. for 30 min. The reaction was stopped by adding 17 µl of 0.5 M acetic acid and by chilling in an ice bath. The stopped reaction mixtures were filtered through 2.5 cm diameter SP membrane discs. The membranes were washed three times with 1 ml of 0.5 M acetic acid to remove the free [$^3$H] acetyl-CoA. The partially dried membranes were placed in 10 ml of Ready-Solv EP scintillation cocktail and counted for 1 min.

The number of acetyl-CoA hydrolase units is calculated as follows:

$$\frac{\text{cpm}_{ACT} - \text{cpm}_{ACT+ACH}}{\text{cpm}_{ACT} - \text{cpm}_{BKD}/10 \text{ (units)}}$$

where $\text{cpm}_{ACT}$ is the number of counts when 10 units of $N^\alpha$-acetyltransferase alone is present; $\text{cpm}_{ACT+ACH}$ is the number of counts when 10 units of $N^\alpha$-acetyltransferase as well as an unknown amount of acetyl-CoA hydrolase are present; and $\text{cpm}_{BKD}$ is the number of background counts. Calculation of the number of units of acetyl-CoA hydrolase is carried out when the value of $\text{cpm}_{ACT+ACH}$ equals approximately 50% of the value of $\text{cpm}_{ACT}$.

One unit of acetyl-CoA hydrolase activity is defined as the amount of enzyme able to inhibit 1 unit of $N^\alpha$-acetyltransferase activity. One unit of $N^\alpha$-acetyltransferase activity is defined as the amount of enzyme able to transfer 1 pmol of [$^3$H] acetyl group from [$^3$H] acetyl-CoA to ACTH (1–24) (Lee, F.-J.S., et al., *J. Biol. Chem.* 263:14948–14955 (1988)).

(B) Radioactive Assay

The principle of the assay is that free acetate, but not acetyl-CoA, will evaporate from an acid solution at an elevated temperature. Aliquots of enzyme solution (1–10 µl) were added to 0.5 ml Eppendorf tubes containing a reaction mixture of 100 mM potassium phosphate buffer, pH 7.4 and 0.25 mM [1-$^{14}$C] acetyl-CoA (0.5 Ci/mol) in a final volume of 100 µl. The assay mixture was incubated at 30° C. for 0.30 s, 1 min, 2 min, 3 min, 4 min, and 5 min. The reaction was stopped by adding 20 µl of 10 M acetic acid. The sample was evaporated by $N_2$ stream at 30° C. to dryness in a fume hood, dissolved in 100 µl $H_2O$, and transferred to a scintillation vial containing 10 ml Ready-Solv EP scintillation cocktail. The sample tube was washed twice with 100 µl $H_2O$, each wash was transferred to the scintillation vial, and the radioactivity was determined by scintillation counting for 1 min. The radioactivity in the control without added acetyl-CoA hydrolase was subtracted from the radioactivity determined at each time point. One unit of activity is defined as the amount of enzyme which hydrolyzes 1 nmol [1-$^{14}$C] acetyl-CoA in 1 minute.

(C) Colorimetric Assay

In the substrate specificity experiment, enzyme activity is measured by following an increase in $A_{412}$ ($\sigma=13,600$ $M^{-1}$) when free CoASH generated during deacylation of acetyl-CoA reacts with 5,5'-dithio-bis-(2-nitro-benzoic acid) (DNTB), as previously described (Robinson, J. B., et al., *Biochem. Biophys. Res. Commun.* 71:959–965 (1976); Bernson, V. S. M., *Eur. J. Biochem.* 67:403–410 (1976)). Each assay solution contained: Tris/HCl, pH 7.6, 100 mM; DNTB, 0.4 mM; acetyl-CoA, 0.25 mM, and an aliquot of an acetyl-CoA hydrolase solution was added in a final volume of 1 ml. The reaction was started by the addition of the aliquot of an acetyl-CoA hydrolase solution, the reaction mixture was incubated at 30° C., and the $\Delta A_{412}$ was measured at 0.30 s, 1 min, 2 min, 3 min, 4 min, and 5 min using a Hewlett-Packard 8450A diode array spectrophotometer.

Cell Growth and Storage

A bakers' yeast strain (TD 71.8) was grown aerobically at 30° C. in YPD medium (1% yeast extract, 2% Bacto-peptone, 2% glucose) in a Chemap AG fermentor (Chemap AG, Volketswil, Switzerland). Cells were harvested when the culture reached on $OD_{660\ nm}$ of 14, concentrated to 38 liters by Alfa-Laval separation system (Alfa-Laval Separation AB, Tumba, Sweden), and stored at −20° C. with 10% (v/v) glycerol for up to 4 months without loss of activity.

Cell Extraction

Concentrated yeast culture (6 liters) was thawed, and yeast cells were collected by centrifugation at 4,000 rpm for 10 min (JS-4.0 rotor, Beckman). The cells (800 g, wet weight) were resuspended in 1 liter of A buffer (50 mM Tris-HCl, pH 7.8, 10 mM $MgCl_2$, 3 mM DTT, 1 M sorbitol) containing 80 mg of lyticase, and the cell suspension was shaken gently at 30° C. for 45 min. All subsequent steps were carried out at 4° C. The spheroplasts were collected by centrifugation at 4,000 rpm for 10 min (JS-4.0 rotor, Beckman), washed by gentle resuspension in 500 ml of A buffer, collected by centrifugation and resuspended gently in 400 ml of B buffer (10 mM HEPES, pH 7.4, 1.4 mM $MgCl_2$, 10 mM KCl, and 0.5 mM DTT). The spheroplasts were lysed in this hypotonic buffer by 15 strokes with a tight-fitting pestle and 15 strokes with a loose-fitting pestle in a Dounce homogenizer, and then cold KCl (2.0 M) was added to give a final KCl concentration of 0.2 M. The homogenate was gently shaken for 30 min, and debris removed by centrifugation at 14,000 rpm for 34 min (JA-14 rotor, Beckman). The supernatant solution was concentrated to a volume of 60 ml, using a PM-30 ultrafiltration membrane and dialyzed overnight against 8 liters of HDG buffer (20 mM HEPES, pH 7.4, 0.5 mM DTT, 10% (v/v) glycerol, and 0.02% $NAN_3$) containing 0.2 M KCl.

DEAE-Sepharose CL-6B Chromatography

DEAE-Sepharose CL-6B was prepared, degassed, and packed into two different columns (2.5×55 cm), following the manufacturer's recommendations. The columns were washed with 4 column volumes of HDG buffer containing 0.2 M KCl (for 0.2 M KCl chromatography) or 0.05 M KCl (for linear KCl gradient chromatography). The dialyzed supernatant solution was applied to DEAE-Sepharose CL-6B equilibrated with HDG buffer containing 0.2 M KCl. Both $N^\alpha$-acetyltransferase and acetyl-CoA hydrolase activity co-eluted from this DEAE-Sepharose CL-6B column at a flow rate of 24 ml/h, as previously shown (Lee, F.-J.S., et al., *J. Biol. Chem.* 263:14948– 14955 (1988)). Fractions (4 ml) were collected, and the fractions containing $N^\alpha$-acetyltransferase and acetyl-CoA hydrolase activity were pooled and concentrated to a volume of 50 ml, using a PM-30 ultrafiltration membrane. This concentrated eluate was dialyzed overnight against 2×4 liters of HDG buffer containing 0.05 M KCl and then applied to a second DEAE-Sepharose CL-6B column (2.5×55 cm) equilibrated in HDG buffer containing 0.5 M KCl. This column was eluted with a linear gradient of 0.05 M (250 ml) to 0.5 M (250 ml) KCl in HDG buffer at 24 ml/h. Fractions (3.6 ml) were collected, and the fractions containing acetyl-CoA hydrolase activity were pooled (FIG. 1) and concentrated to a volume of 5 ml, using a PM-30 ultrafiltration membrane.

Sepharose CL-4B Chromatography

Figure 2:
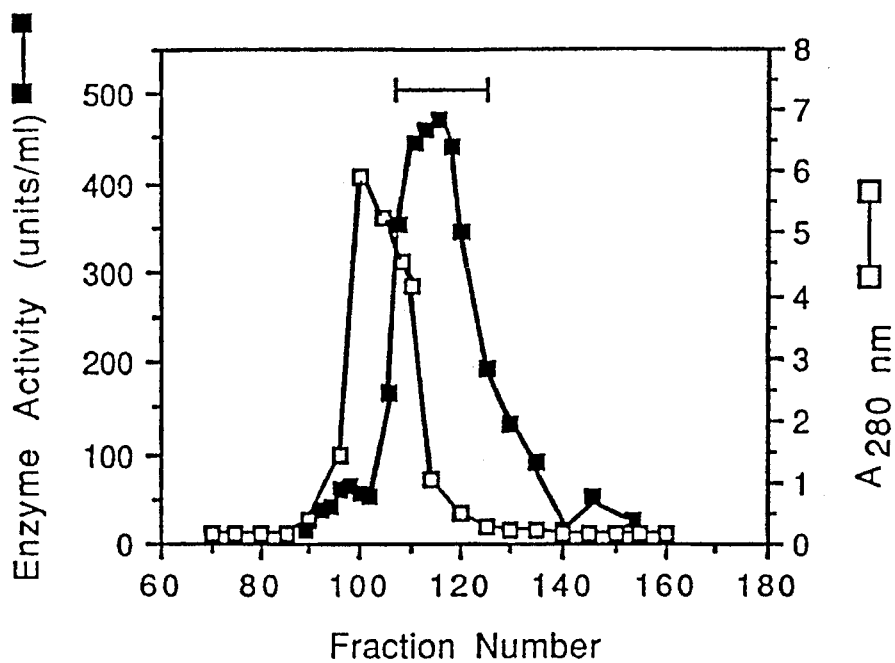
FIG. 2 shows the elution profile obtained from the chromatography of yeast acetyl-CoA hydrolase on Sepharose CL-4B. The acetyl-CoA hydrolase pool from DEAE-Sepharose was concentrated and applied to a Sepharose CL-4B gel column, eluted with 200 mM potassium phosphate buffer, pH 7.4, containing 0.5 mM DTT, 10% (v/v) glycerol, 0.02% $NaN_3$ at 20 ml/h, and analyzed for $A_{280}$ and enzyme activity (acetylation inhibition assay). Fractions containing acetyl-CoA hydrolase activity were pooled as indicated by the horizontal bar.

The concentrated eluate from the second DEAE-Sepharose chromatography was applied to a Sepharose CL-4B column (2.5×96 cm). The column was eluted with HDG buffer containing 0.2 M KCl at 20 ml/h. The elution volume of the enzyme was determined by A280 nm and enzyme activity. Fractions (3.0 ml) were collected, and the fractions containing acetyl-CoA hydrolase activity were pooled (FIG. 2) and concentrated to a volume of 1.5 ml, using a PM-30 ultrafiltration membrane.

Hydroxylapatite Chromatography

Figure 3:
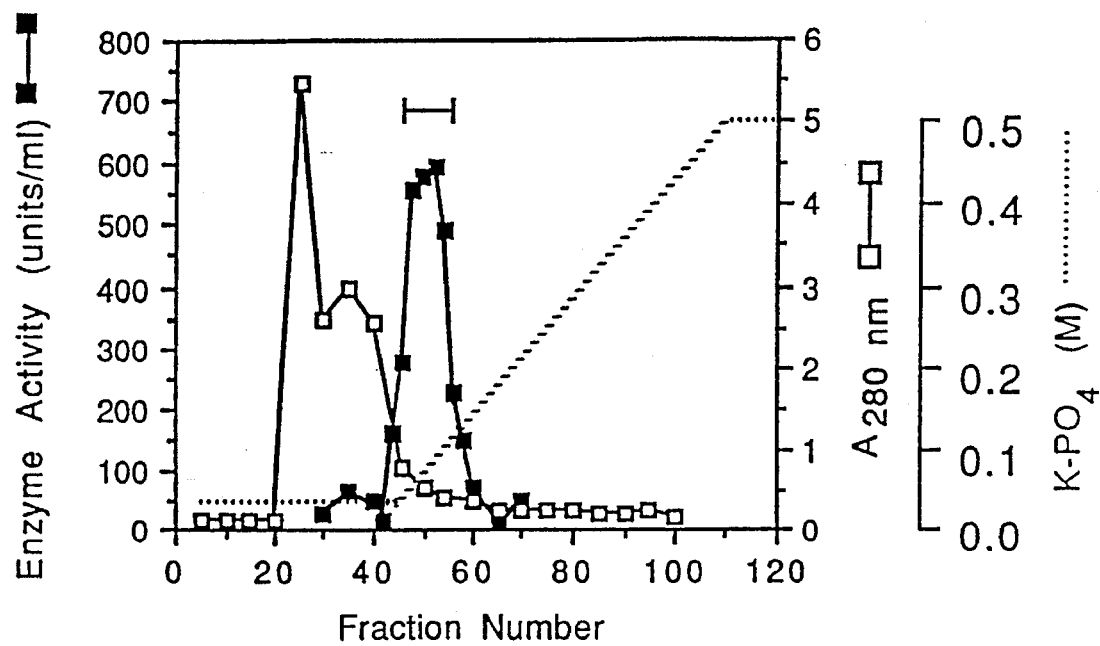
FIG. 3 shows the elution profile obtained from the chromatography of yeast acetyl-CoA hydrolase on a column of hydroxylapatite. The acetyl-CoA hydrolase pool from Sepharose CL-4B chromatography was concentrated, dialyzed, and applied to a hydroxylapatite column. The column was eluted with a linear gradient of 0.05 M (150 ml) to 0.5 M (150 ml) potassium phosphate buffer, pH 7.4, containing 0.5 mM DTT, 10% (v/v) glycerol, 0.02% $NaN_3$ at 12 ml/h. Fractions were collected and analyzed for absorbance at 280 nm and for enzyme activity in the acetylation inhibition assay. Fractions containing acetyl-CoA hydrolase activity were pooled as indicated by horizontal bar.

The concentrated eluate from Sepharose CL-4B chromatography was dialyzed overnight against 2×4 liters of 0.05 M potassium phosphate buffer, pH 74, 0.5 mM DTT, 10% (v/v) glycerol, 0.02% $NaN_3$ and applied to a hydroxylapatite column (2.0×25 cm) equilibrated with the same buffer used for dialysis. The column was eluted with a linear gradient of 0.05 M (150 ml) to 0.5 M (150 ml) potassium phosphate buffer, pH 7.4, containing 0.5 mM DTT, 10% (v/v) glycerol, 0.02% NaN$_3$ at 12 ml/h. Fractions (1.8 ml) were collected, and the fractions containing acetyl-CoA hydrolase activity were pooled (FIG. 3) and concentrated to a volume of 1.5 ml, using a PM-30 ultrafiltration membrane. Aliquots (25 μl) of various fractions from fractions 40–60 were analyzed on a SDS-PAGE gel (9%) under reducing conditions, as described by Laemmli (Laemmli, U. K., *Nature* 227:680–685 (1970)). Protein bands were stained with Coomassie Brilliant Blue R.

Sodium Dodecyl Sulfate-Polyacrylamide Gel Electrophoresis

A sample of each pool containing acetyl-CoA hydrolase isolated from each purification step was analyzed on an SDS-PAGE gel (9%) under reducing conditions, as described by kaemmli (Laemmli, U. K., *Nature* 227:680–685 (1970)). For determination of M$_r$ of purified enzyme subunits, myosin (205,000), *E. coli* β-galactosidase (116,000), rabbit muscle phosphorylase (97,000), bovine serum albumin (66,000), egg albumin (45,000), and carbonic anhydrase (29,000) were used as molecular weight standards. Protein bands were stained with Coomassie Brilliant Blue R. Higher M$_r$ bands were not observed in lanes containing either crude extract or the DEAE-Sepharose (0.2 M KCl) pool The absence of such bands is due to proteolytic degradation which occurred during prolonged storage.

Isoelectric Point Determination

Isoelectric focusing, using an aliquot from the hydroxylapatite pool (FIG. 3), was performed as previously described (Catsimpoolas, N., *Isoelectric Focusing*, Academic Press, New York (1976)) (pH range 3.5–9.5). For determination of pI of purified enzyme subunits, *A. oryzae* amyloglucosidase (pI=3.55), soybean trypsin inhibitor (pI= 4.55), milk β-lactoglobulin (pI=5.13), bovine erythrocytes carbonic anhydrase B (pI= 5.85), human erythrocytes carbonic anhydrase B (pI=6.57), horse heart myoglobin (pI= 6.76 and 7.16), rabbit muscle L-lactic dehydrogenase (pI= 8.3, 8.4, and 8.55), and bovine pancreas trypsinogen (pI= 9.3) were used as pI standards. Protein bands were stained with Coomassie Brilliant Blue R.

Molecular Size Determination

The M$_r$ of the native protein was estimated by comparison to molecular weight standards by gel filtration on Sepharose CL-4B column (2.5×96 cm). An aliquot of the purified enzyme from the hydroxylapatite chromatography pool was applied to the column. The column was eluted with HDG buffer containing 0.2 M KCl at 20 ml/h. The elution volume of the enzyme was determined by A$_{280}$ nm and enzyme activity (acetylation inhibition assay), and the apparent molecular weight of yeast acetyl-CoA hydrolase was calculated by comparison with the relative elution volumes of protein standards including thyroglobulin (669,000), apoferritin (443,000), β-amylase (200,000), alcohol dehydrogenase (150,000), bovine serum albumin (66,000) and carbonic anhydrase (29,000).

Amino Acid Analysis

The concentrated eluate from the hydroxylapatite chromatography was applied to a 7% SDS-PAGE gel of 1.5 mm thickness in a 12 cm well, electrophoresed, and electroeluted as previously described (Hunkapiller, M., et al., *Methods Enzymol.* 91:227–236 (1983)). The amino acid composition was determined using a Beckman 6300 Amino Acid Analyzer after 24 hr hydrolysis at 110° C. in 6 N HCl containing 0.1% phenol (Moore, S., *Chemistry and Biology of Peptides*, Meienhofer, J., ed., Ann Arbor Science, Ann Arbor, Mich., pp. 629–652).

Protein Sequence Analysis

Protein sequence analysis of electroeluted acetyl-CoA hydrolase was carried out twice (each ≈300 pmole) by using an Applied Biosystems 470A Protein Sequencer and an Applied Biosystems 120A Pth Analyzer (Hewick, R. M., et al., *J. Biol. Chem.* 256:7990–7997 (1981)).

Chemical Modifications

DEPC (liquid, approximately 6.8 M) was diluted to 1 M with cold 100% ethanol. Further dilutions of DEPC were made with 0.1 M sodium phosphate (pH 6.0) containing 1 mM EDTA and 5% ethanol. NBS and succinic anhydride were dissolved in acetone and diluted with distilled water prior to use. NEM, IAA, IAM, (HNBS(CH$_3$)2-Br), TNBS, and N-acetylimidazole solution were prepared in distilled water. pCMB was prepared in 10 mM NaOH as a concentrated solution and diluted with distilled water prior to use.

The individual inhibition experiments were done at 25° C. by incubating the enzyme in 100 mM potassium phosphate buffer (pH 7.4) containing the various modification reagents, except for (HNBS(CH$_3$)2-Br) and DEPC, which were done in 50 mM sodium phosphate buffer (pH 6.0). After 15 min, each sample aliquot was dialyzed using a microdialyzer against 100 mM potassium phosphate, pH 7.4, 1 mM DTT at 4° C. for 3 to 4 h. The enzyme activity was determined using the radioactive assay for acetyl-CoA hydrolase. As a control, the enzyme was incubated separately without added reagents.

Peptide Synthesis

Human ACTH (1–24) were synthesized on an Applied Biosystems Model 430A peptide synthesizer and characterized, as previously described (Finnegan, A., et al., *J. Exp. Med.* 164:897–910 (1986)).

Results

Homogeneity and Molecular Properties

Acetyl-CoA hydrolase from *S. cerevisiae* was purified 2,400-fold from 800 g of cells (Table 1) with an overall recovery of 31%. Purification was achieved by successive chromatographic steps utilizing DEAE-Sepharose, Sepharose CL-4B, and hydroxylapatite. The enzyme comprises approximately 0.2 % of the total cellular protein.

TABLE 1

Purification of Acetyl-CoA Hydrolase from *S. cerevisiae*

| Step | Activity (units) | Protein (mg) | Specific Activity (unit/mg) | Purification (fold) | Yield (%) |
|---|---|---|---|---|---|
| 1. Crude Extract | 31300[b] | 19500 | 1.6 | 1.0 | 100[b] |
| 2. DEAE-Sepharose (0.2 M KCl) | 31400[b] | 4250 | 7.4 | 4.6 | 100[b] |
| 3. DEAE-Sepharose (0.05–0.5 M KCl) | 26300 | 862 | 30.5 | 19.1 | 84 |
| 4. Sepharose CL-4B | 16800 | 304 | 55.3 | 34.6 | 54 |
| 5. Hydroxylapatite | 9600 | 2.5 | 3840 | 2400 | 31 |

[a]Activity was measured as described below.
[b]In the first two chromatographic steps, N$^\alpha$-acetyltransferase and acetyl-CoA hydrolase were present in the same fractions (Lee, F.J.S. et al., J. Biol. Chem. 263:14948-14955 (1988)), and the activity of acetyl CoA hydrolase could not be determined. After the third chromatographic step, the N$^\alpha$-acetyltransferase and acetyl CoA hydrolase were separated, and the total activity of N$^\alpha$-acetyltransferase was 63,300 units. However, the activity of N$^\alpha$-acetyltransferase determined in the first two steps was only 32,000 units. If one assumes that the true activity of N$^\alpha$-acetyltransferase in the first two chromatographic steps was actually 63,300 units, and that all the inhibition of acetyltransferase was caused by acetyl CoA hydrolase, then the activity of acetyl CoA hydrolase can be estimated to be 31,300 units in each of the first two chromatographic steps.

Figure 4:
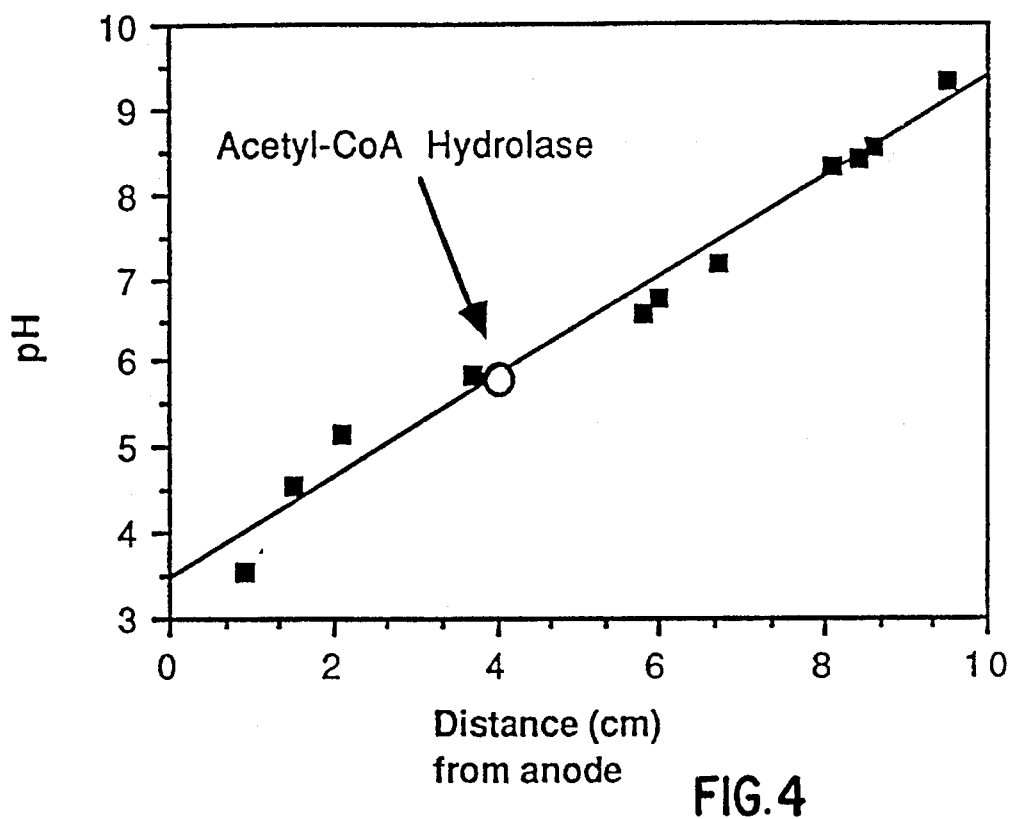
FIG. 4 shows a determination of the isoelectric point of yeast acetyl-CoA hydrolase by isoelectric focusing. Isoelectric focusing, using an aliquot from the hydroxylapatite pool (FIG. 3), was performed as previously described (Catsimpoolas, N., Isoelectric Focusing, Academic Press, New York (1976)) (pH range 3.5–9.5). For determination of the pI of purified enzyme subunits, A. oryzae amyloglucosidase (pI= 3.55), soybean trypsin inhibitor (pI=4.55), milk β-lactoglobulin (pI=5.13), bovine erythrocytes carbonic anhydrase B (pI=5.85), human erythrocytes carbonic anhydrase B (pI= 6.57), horse heart myoglobin (pI=6.76 and 7.16), rabbit muscle L-lactic dehydrogenase (pI=8.3, 8.4, and 8.55), and bovine pancreas trypsinogen (pI= 9.3) were used as pI standards. Protein bands were stained with Coomassie Blue.

The molecular weight of denatured and reduced yeast acetyl-CoA hydrolase was estimated to be 65,000±2,000 as determined by SDS gel electrophoresis. An aliquot of sample was analyzed using a 9% reduced gel according to the method of Laemmli (Laemmli, U. K., *Nature* 227:680–685 (1970)) and compared to molecular weight standards: myosin (205,000), *E. coli* β-galactosidase (116,000), rabbit muscle phosphorylase (97,000), bovine serum albumin (66,000), and egg albumin (45,000). The molecular weight of native yeast acetyl-CoA hydrolase was estimated by gel filtration. An aliquot of the purified enzyme from hydroxylapatite chromatography was applied to a Sepharose CL-4B column (2.5×96 cm). The elution buffer was HDG buffer containing 0.2 M KCl, and the flow rate was 20 ml/h as described below. The elution volume of acetyl-CoA hydrolase was determined by the acetylation inhibition assay, and the apparent molecular weight was calculated by comparison to the elution volumes of protein standards: (1) thyroglobulin (669,000), (2) apoferritin (443,000), (3) β-amylase (200,000), (4) alcohol dehydrogenase (150,000), (5) bovine serum albumin (66,000), and (6) carbonic anhydrase (29,000). Gel filtration chromatography on Sepharose CL-4B suggested a $M_r$ for the native acetyl-CoA hydrolase of 64,000±5,000. Taken together with the results from SDS PAGE, this data indicates that yeast acetyl-CoA hydrolase is monomeric. This conclusion is supported by isoelectric focusing results which revealed a single protein band with an apparent pI of 5.8 (FIG. 4).

Figure 5A:
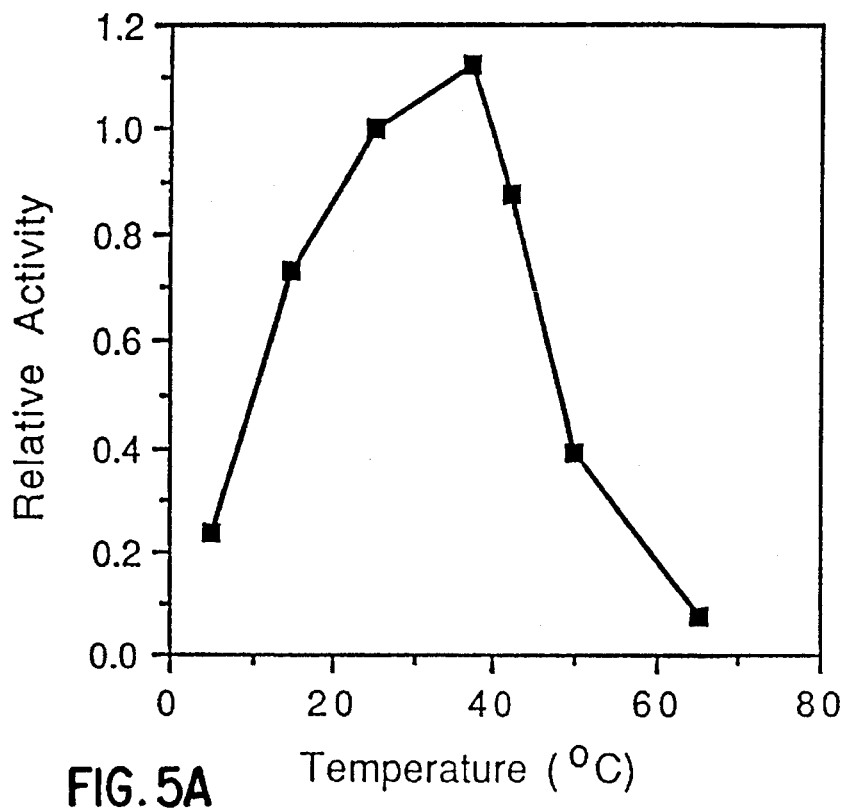
FIGS. 5A and 5B show the effect of temperature and pH on yeast acetyl-CoA hydrolase activity.
Figure 5B:
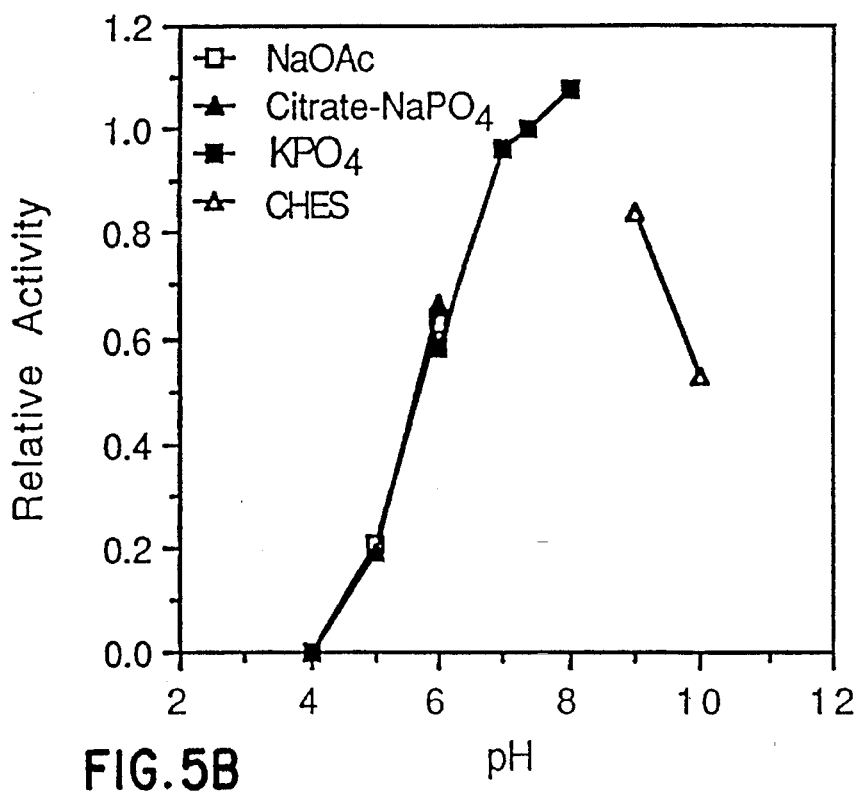

Yeast acetyl-CoA hydrolase activity was measured at pH values from 4 to 10 using 100 mM buffers of sodium acetate, citrate phosphate, potassium phosphate, and CHES (FIG. 5B). Maximum enzyme activity is observed at pH 8.0. Activity is reduced to <20% of maximum below pH 5.0 and to <10% of maximum above pH 10.

The enzymatic activity of yeast acetyl-CoA hydrolase was examined at temperatures ranging from 5° C. to 65° C. (FIG. 5A). The enzyme exhibited maximum activity at temperatures from 37° C. to 42° C. Irreversible denaturation occurred after 1 minute at 65° C. The enzyme was most stable when stored at 4° C. in 0.1 M potassium phosphate buffer, pH 7.4. Under these conditions, the purified enzyme had a half-life of approximately 2 weeks. The enzyme was less sensitive to freezing at all stages of purification and displayed only a <10% loss of activity per freeze-thaw cycle.

Figure 6A:
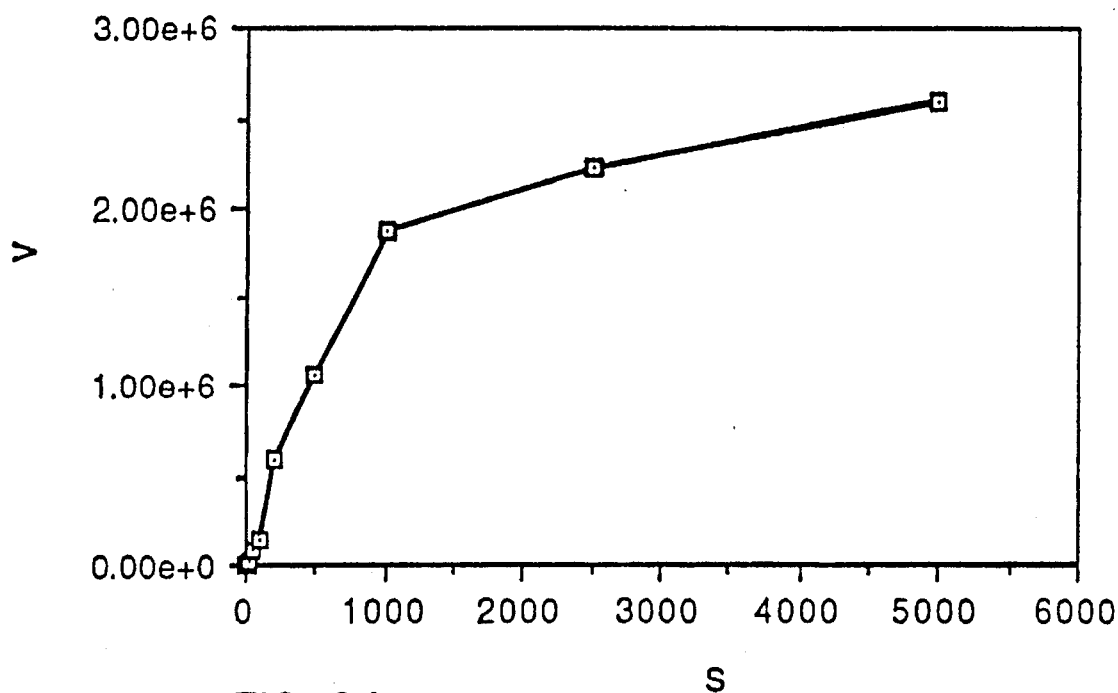
FIG. 6(A) shows a straight plot of Acetyl-CoA concentration versus rate of acetate release for acetyl-CoA hydrolase.
Figure 6B:
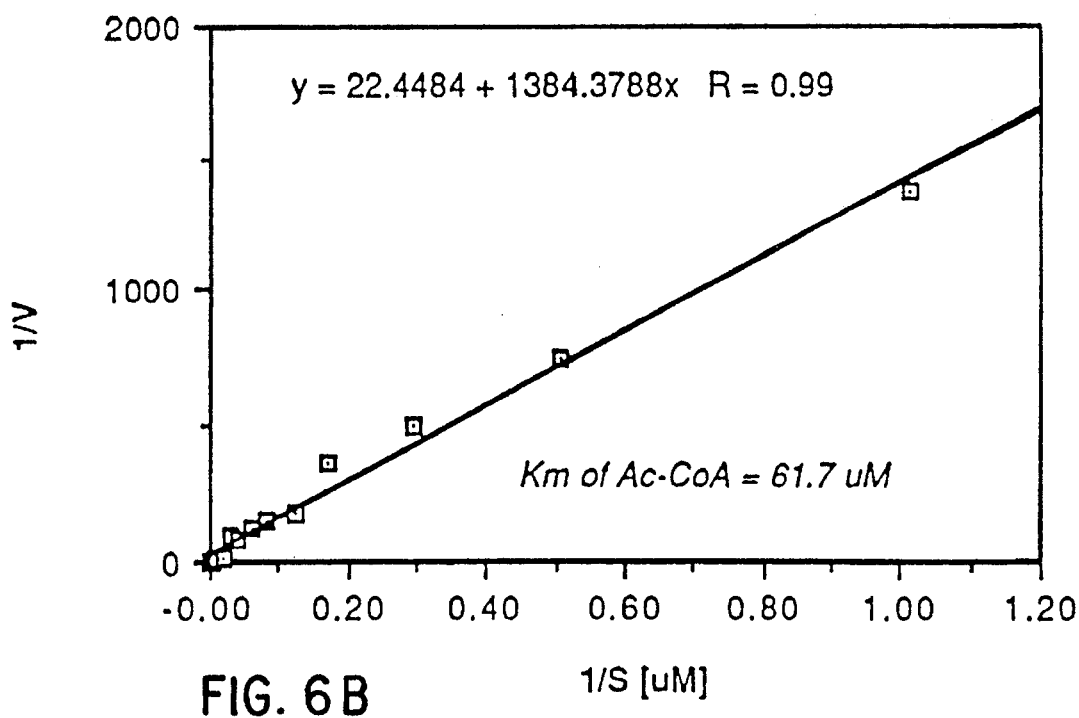
FIG. 6B shows a Lineweaver-Burk plot of Acetyl-CoA concentration versus rate of acetate release for acetyl CoA hydrolase.

FIG. 6A shows plot of substrate concentration versus reaction velocity for acetyl-CoA hydrolase assayed using the radioactive assay. The curve has the regular hyperbolic shape indicative of an enzyme obeying ordinary Michaelis-Menten kinetics. FIG. 6B is a Lineweaver-Burk plot which shows the apparent Km for acetyl-CoA hydrolase to be approximately 62 µM. The hydrolysis of [1-$^{14}$C] acetyl-CoA by acetyl-CoA hydrolase is inhibited by <30% at CoASH concentrations of >25 µM.

As used herein, the term "substantially pure" or "substantially purified" is meant to describe acetyl-CoA hydrolase which is substantially free of any compound normally associated with the enzyme in its natural state, i.e., free of extraneous proteins or carbohydrates. The term is further meant to describe acetyl-CoA hydrolase which appears to be homogeneous using criteria of those skilled in the art. For example, a substantially pure acetyl-CoA hydrolase will show constant and reproducible characteristics for parameters such as: molecular weight and chromatographic elution position. The term, however, is not meant to exclude artificial or synthetic mixtures of the enzyme with other compounds. The term is also not meant to exclude the presence of minor impurities which do not interfere with the biological activity of the enzyme and which may be present due to incomplete purification.

Amino Acid Analysis

Samples of yeast acetyl-CoA hydrolase were subjected to amino acid analysis and the amino acid composition of the enzyme is shown in Table 2. The composition is characteristic of a globular protein.

TABLE 2

| Amino Acid Composition of Acetyl-CoA Hydrolase from *S. cerevisiae*[a] | |
|---|---|
| Amino Acid | Observed Residues[b] |
| Asx | 75 |
| Thr | 24 |
| Ser | 33 |
| Glx | 53 |
| Pro | 51 |
| Gly | 34 |
| Ala | 49 |
| Val | 44 |
| Met | 4 |
| Ile | 35 |
| Leu | 51 |
| Tyr | 15 |
| Phe | 37 |
| Lys | 29 |
| His | 17 |
| Arg | 28 |

[a]Purified acetyltransferase was electroeluted from a preparative SDS-PAGE gel. The amino acid composition was determined from six different enzyme preparations using a Beckman 6300 Amino Acid Analyzer after 24 hr hydrolysis at 110° C. in 6 N HCl containing 0.1% phenol. Asx = Asp + Asn; Glx = Glu + Gln.
[b]Residue number per subunit of enzyme was calculated on the basis of a $M_r$ = 64,000. No correction was made for the amounts of Ser and Thr destroyed during the 24 hr hydrolysis. Cys and Trp were not determined.

Amino Acid Sequence Analysis

Two different preparations of protein (each ~300 pmole) were subjected to protein sequence analysis. Except for background levels of amino acids appearing during the first cycle of sequence analysis, no protein sequence was detected. These results demonstrate that the N-terminus of the protein is blocked.

The protein was cleaved with trypsin and the resulting cleavage fragments were separated by HPLC on a phenyl reversed phase column. Two of the fragments were sequenced. Sequence information for these two random fragments was as follows:

Fragment #689 (Peptide 19-1; SEQ. ID No. 1):
```
     2      4      6      8     10     12     14
Phe—Asn—Leu—Phe—Val—Gly—Ala—Ser—Ala—Gly—Pro—Glu—Glu—Asn—Arg
```

Fragment #690 (Peptide 10-2; SEQ. ID No. 3):
```
     2      4      6      8     10
Val—Val—Ala—Ile—Val—Glu—Ser—Thr—Met—Arg
```

As described below, sequence information obtained from the peptide fragments was used in constructing probes needed for the cloning of the enzyme.

Effect of Nucleotides and Divalent Cations on Enzyme Activity

The effect of various nucleotides and divalent cations on enzyme activity was determined (Table 3). At a nucleotide concentration of 0.1 mM only βNADH appreciably decreased enzyme activity in a concentration dependent manner. Divalent cations inhibited enzymatic activity to a variable degree:

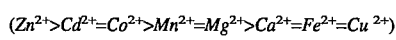

TABLE 3

Effect of Nucleotides and Ions on Enzyme Activity of Acetyl-CoA Hydrolase from S. cerevisiae[a]

| Additions | Enzyme Activity (%) Concentration (mM) | | |
|---|---|---|---|
| | 10 | 1 | 0.1 |
| None | 100 | 100 | 100 |
| βNADH | 46 | 69 | 83 |
| βNAD | 95 | 98 | 100 |
| βNADPH | 96 | 98 | 99 |
| AMP | 81 | 89 | 96 |
| ADP | 91 | 94 | 98 |
| ATP | 96 | 99 | 101 |
| ZnSO$_4$ | 25 | 88 | — |
| CdCl$_2$ | 48 | 91 | — |
| CoCl$_2$ | 51 | 86 | — |
| MnCl$_2$ | 64 | 84 | — |
| MgCl$_2$ | 72 | 95 | — |
| MgSO$_4$ | 75 | 98 | — |
| CaCl$_2$ | 84 | 97 | — |
| FeSO$_4$ | 88 | 98 | — |
| CuSO$_4$ | 89 | 94 | — |

[a]Yeast acetyl-CoA hydrolase was incubated in the presence of various nucleotides and divalent cations in 100 mM potassium phosphate, pH 7.4. The enzyme activity was determined under standard radioactive assay conditions using ACTH (1–24) (N = 3), as described in the Examples.

Effect of Chemical Modifications on Enzyme Activity

In order to determine a possible catalytic role for different types of amino acid residues in the enzyme, various chemical modifications were carried out (Table 4). The reaction of acetyl-CoA hydrolase with diethyl pyrocarbonate, a histidine-modifying reagent (Miles, E. W., Methods Enzymol. 47:431–442 (1977)), caused a nearly complete inactivation of the enzyme. After incubation for 8 h at room temperature with 0.25 M hydroxylamine, a reagent capable of reversing the ethoxyformylation of histidine residues, ≈55 % of the original enzyme activity could be recovered, although prolonged exposure to hydroxylamine slowly inactivated the enzyme. The presence of a catalytically important tryptophan residue was investigated by chemical modification with NBS (Spande, T. F. et al., Methods Enzymol. 11:506–522 (1967)) and HNBS(CH$_3$)$_2$-Br (Horton, H. R. et al., Methods Enzymol. 25:468–482 (1972)). NBS inactivated the enzyme by 70% at 0.5 mM and caused complete inactivation at a concentration of 5 mM. Although HNBS(CH$_3$)$_2$-Br partially inactivated the enzyme, the loss of activity was small in comparison to the amount of inactivation observed with NBS. Since NBS can also modify histidine and tyrosine residues (Witkop, B., Adv. Protein Chem. 16:221–321 (1963)), it is possible that the inactivation might be due to a chemical modification of the same histidine(s) modified by diethyl pyrocarbonate. Sulfhydryl-reducing agents (i.e. 2-mercaptoethanol and DTT) did not affect enzyme activity. Sulfhydryl-modifying reagents (i.e. NEM, iodoacetic acid, iodoacetamide, and pCMB) had no effect at 1 mM, but partially inactivated the enzyme at 10 mM. Succinic anhydride and TNBS, which modify lysine residues and α-NH$_2$ groups (Riordan, J. F. et al., Methods Enzymol. 25:500–506 (1972); Fields, R., Methods Enzymol. 25:464–468 (1972)), had no effect at 1 mM, but caused partial inactivation at 10 mM. N-acetylimidazole, a tyrosine-modifying reagent, also caused inactivation but only at a concentration of 10 mM (Riordan, J. F. et al., Methods Enzymol. 25:500–506 (1972)).

TABLE 4

Effect of Protein Modification Reagents on Enzyme Activity of Acetyl-CoA Hy&olase from S. ceresisiae[a]

| Reagent Added[b] | Concentration (mM) | Enzyme Activity (%) |
|---|---|---|
| None | | 100 |
| DEPC | 0.5 | 19 |
| | 5.0 | 3 |
| NBS | 0.5 | 30 |
| | 5.0 | 2 |
| HNBS(CH$_3$)$_2$—Br | 1.0 | 84 |
| | 10.0 | 71 |
| 2-mercaptoethanol | 10.0 | 101 |
| DTT | 10.0 | 104 |
| NEM | 1.0 | 94 |
| | 10.0 | 52 |
| IAA | 1.0 | 99 |
| | 10.0 | 89 |
| IAM | 1.0 | 97 |
| | 10.0 | 85 |
| pCMB | 1.0 | 102 |
| | 10.0 | 88 |
| TNBS | 1.0 | 94 |
| | 10.0 | 77 |
| Succinic anhydride | 1.0 | 95 |
| | 10.0 | 79 |
| N-acetylimidazole | 1.0 | 101 |
| | 10.0 | 67 |

[a]Yeast acetyl-CoA hydrolase was incubated with each reagent at 25° C. for 15 min, dialyzed against 100 mM potassium phosphate buffer, pH 7.4, at 4° C. for 3 to 4 hr. The enzyme activity was determined under standard radioactive assay conditions using acetyl-CoA (1–24) (N = 3), assayed as described in the Examples.
[b]Abbreviations: DEPC, diethyl pyrocarbonate; NBS, N-bromo-succinimide; HNBS(CH$_3$)$_2$—Br, dimethyl-(2-hydroxy-5-nitrobenzyl)-sulfonium bromide; NEM, N-ethylmaleimide; IAA, iodoacetic acid; IAM, iodoacetamide; PCMB, p-chloromercuribenzoate; TNBS, 2,4,6-trinitrobenzenesulfonic acid.

Substrate Specificity

Several acetyl-CoA derivatives of varying chain length were tested as substrates for yeast acetyl-CoA hydrolase. Each of the acetyl-CoA derivatives in Table 5 were compared to underivatized acetyl-CoA. Enzyme activities were determined at substrate concentrations of 0.25 mM. The results indicate that the enzyme is relatively specific for underivatized acetyl-CoA although the derivatives do show some activity. Each acyl-CoA was found to inhibit acetyl-CoA hydrolase in the radioactive assay, although acetyl-CoA inhibited most effectively (Table 6).

TABLE 5

Inhibition of Acyl-CoA on Enzyme Activity of Acetyl-CoA Hydrolase from S. cerevisiae[a]

| Substrates | Relative Activity (%) |
|---|---|
| Acetyl-CoA | 100 |
| Malonyl-CoA | 1 |
| Propionyl-CoA | 9 |
| Butyryl-CoA | 4 |
| Acetoacetyl-CoA | 5 |
| Succinyl-CoA | 8 |
| Myristoyl-CoA | 3 |

[a]The enzyme activity was determined using the colorimetric assay (N = 3) described in the Examples.

TABLE 6

Inhibition of Acyl-CoA on Enzyme Activity of
Acetyl-CoA Hydrolase from *S. cerevisiae*[a]

| Additions | Enzyme Activity (%) Concentration (mM) | | |
|---|---|---|---|
| | 5 | 1 | 0.1 |
| None | 100 | 100 | 100 |
| Acetyl-CoA | 5 | 28 | 66 |
| Myristoyl-CoA | 52 | 83 | 93 |
| Succinyl-CoA | 56 | 79 | 92 |
| Butyryl-CoA | 62 | 86 | 95 |
| Propionyl-CoA | 72 | 89 | 92 |
| Acetoacetyl-CoA | 90 | 92 | 98 |
| Malonyl-CoA | 52 | 83 | 93 |

[a]Yeast acetyl-CoA hydrolase was incubated in the presence of various acyl-CoA in 100 mM phosphate buffer, pH 7.4. The enzyme activity was determined under radioactivity assay conditions using acetyl-CoA (N = 3), as described in the Examples.

EXAMPLE 2

Cloning of the Acetyl—CoA Hydrolase Gene Sequence

Growth of cells

Yeast cells were grown at 30° C. on complete medium (1% yeast extract, 2% peptone) containing 2% glucose, 3% glycerol, 2% galactose, or 3% potassium acetate, as indicated. Crude yeast lysates were prepared, and acetyl-CoA hydrolase activity was determined by radioactive assay, as previously described (Lee, F.-J.S., et al., *Eur. J. Biochem.* 184:21–28 (1989)). Briefly, aliquots of enzyme solution (1–10 µl) were added to 0.5 ml Eppendorf tubes containing a reaction mixture, of 100 mM potassium phosphate buffer, pH 7.4 and 0.25 mM [1-$^{14}$C]acetyl-CoA (0.5 Ci/mol) in a final volume of 100 µl. The assay mixture was incubated at 30° C. for 0, 30 s, 1 min, 2 min, 3 min, 4 min, and 5 min. The reaction was stopped by adding 20 µl of 10 M acetic acid. The sample was evaporated by $N_2$ stream at 30° C. to dryness in a fume hood, dissolved in 100 µl $H_2O$, and transferred to a scintillation vial containing 10 ml Ready-Solv EP scintillation cocktail. The sample tube was washed twice with 100 µl $H_2O$, both washes were also transtarred to the scintillation vial, and the radioactivity was determined by scintillation counting for 1 min. The radioactivity in the control without added acetyl-CoA hydrolase was subtracted from the radioactivity determined at each time point. One unit of activity is defined as the amount of enzyme which hydrolyses 1 nmol [1-$^{14}$C]acetyl-CoA in 1 min.

Purification of enzyme

Acetyl-CoA hydrolase was purified from yeast as previously described (Lee, F.-J.S., et al., *Eur. J. Biochem.* 184:21–28 (1989)). Acetyl-CoA hydrolase (4 nmoles) was reduced and alkylated, precipitated with cold chloroform/methanol, redissolved in 0.1 M $NH_4HCO_3$, incubated with TPCK-treated trypsin (EC 3.4.21.4; Cooper Biomedical, Malvern, Pa.) (160 pmol) for 24 hr at 37° C., recovered by lyophilization, and dissolved in 6 M guanidine hydrochloride in 0.1% $CF_3COOH$ prior to HPLC.

Tryptic peptides were separated on a Vydac phenyl (0.46× 25 cm) HPLC column, and selected fractions were rechromatographed isocratically (Wong, W. W., et al., *Proc. Natl. Acad. Sci. USA* 82:7711–7715 (1985)). Chromatographic peaks were detected at 214 and 280 nm, collected manually, and lyophilized. The tryptic peptides were sequenced by automated Edman degradation performed with an Applied Biosystems 470A Protein Sequencer and an Applied Biosystems 120 Pth Analyzer (Hewick, R. M., et al., *J. Biol. Chem.* 256:7990–7997 (1981)).

Analyses of Tryptic Peptides of Acetyl-CoA Hydrolase

Tryptic peptides from yeast acetyl-CoA hydrolase were separated by reversed-phase HPLC and collected as 45 pools representing distinct peaks or shoulders. In brief, 4 nanomoles of purified acetyl-CoA hydrolase was reduced, alkylated, digested with trypsin, and chromatographed on a 0.46× 25 cm Vydac phenyl HPLC column with 0.1% $CF_3COOH$ in a linear gradient of 0–60% $CH_3CN$ over 2 hr. After additional isocratic HPLC separation to resolve further individual sequenceable tryptic peptides (Wong, W. W., et al., *Proc. Natl. Acad. Sci. USA* 82:7711–7715 (1985)), the sequences of 16 peptides, comprising approximately 41% of the complete acetyl-CoA hydrolase sequence, were determined.

Synthesis of Oligonucleotide Probes

Figures 7A, 7B:
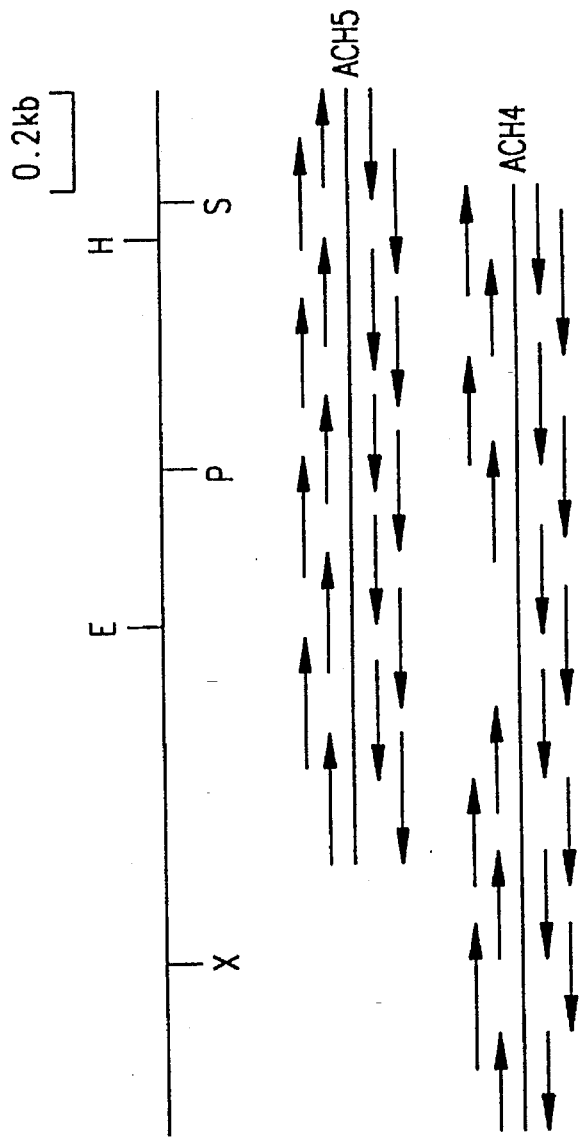

The method adopted for the identification and cloning of cDNA sequences derived from acetyl-CoA hydrolase mRNA utilized oligonucleotide probes that were constructed based on amino acid sequences of purified acetyl-CoA hydrolase tryptic peptides and on codon-usage frequency data (Lathe, R., *J. Mol. Biol.* 183:1–12 (1985)). Two synthetic, codon-usage based oligonucleotides of 45 bases (A1; SEQ. ID No. 2) and 30 bases (A2; SEQ. ID No. 4) were prepared based on the sequences of a 15-residue (peptide 19-1) and a 10-residue (peptide 10-2) peptide (FIG. 7A). In addition, two degenerate oligonucleotide probes of 17 (5' ATCATYTCXGGRTTRTT 3'; SEQ. ID No. 9) and 14 (3' GGXGCRTGCATXAT 5'; SEQ. ID No. 10)) bases both with 32-fold redundancy, designated A3 and A4, were synthesized based on sequence data for peptides 8-1 and 9-1, respectively.

In detail, the yeast cDNA library was prepared as described by Lee, F.-J.S., et al. (*J. Biol. Chem.* 264:12339–12343 (1989)). The two oligonucleotide probes (A1 and A2) were synthesized with an Applied Biosystems 380A DNA synthesizer by using the silica-based solid-phase method (Matteucci, M. D., et al., *J. Am Chem. Soc.* 103:3185–3191 (1981)) and β-cyanoethyl phosphoramidite method (Sinha, N. D., et al., *Nucleic Acids Res.* 12:4539–4544 (1984)). The purified oligonucleotides were isolated from the crude synthetic mixtures by PAGE and labelled to a specific activity of 2–8× $10^8$ cpm/µg using [γ-$^{32}$P]-ATP (New England Nuclear) and T4 polynucleotide kinase (New England Biolabs) (Zoller, M., et al., *DNA (N.Y.)* 3:479–488 (1985)).

Cloning of the Yeast Acetyl-CoA Hydrolase cDNA

In the initial screen, 500,000 recombinant clones in λgt11 yeast cDNA library were plated on *E. coli* Y 1088. Duplicate transfers of the clones were made onto nitrocellulose, and the membranes were prepared for hybridization (Zoller, M., et al., *DNA (N.Y.)* 3:479–488 (1985)). Afterward, the membranes were washed twice at room temperature in 6xSSC (0.15 M NaCl/15 mM sodium citrate) containing 0.1% SDS and 0.05% sodium pyrophosphate), washed once at 5° C. below the minimum $t_d$ (temperature of probe dissociation based on G/C content), and exposed on x-ray film for 1 to 2d. Maximum and minimum $t_d$ were determined for two pools of redundant oligonucleotide probes (A3 and A4) (Suggs, S. V., et al., in *Developmental Biology Using Purified Genes* (Brown, D., ed.), Academic Press, Orlando, Fla., pp. 683–693 (1981)).

After this initial screening in the yeast λgt11 eDNA library, 17 clones were detected which hybridized to both oligonucleotides A1 and A2. These clones, designated λA1 to λA17, also hybridized with two other oligonucleotides A3 and A4, and their eDNA inserts were analyzed by restriction enzyme digestions and DNA blot analyses. The use of four oligonucleotide probes derived from four discrete amino acid sequences allowed the unequivocal identification of the cDNA clones encoding acetyl-CoA hydrolase. XbaI digestion revealed inserts that lacked internal XbaI sites and ranged from 1.8 to 2.3 kb. The five longest cDNA inserts were subcloned as XbaI fragments into the Bluescript plasmid, and additional restriction enzyme mapping, DNA blot analyses, and nucleotide sequence analyses were carried out. Four eDNA clones (pBA2, pBA3, pBA5, pBA17), represented as ACH5 in FIG. 7B, displayed identical restriction maps, and ACH4 (derived from pBA4) overlapped them.

Sequence Analysis of the cDNA Clones cDNA fragments were cleaved from recombinant λgt11 phage DNA by XbaI digestion. The eDNA fragments were separated by gel electrophoresis in low melting point agarose. The correct DNA band was excised, the gel was melted at 65° C., and the DNA was extracted with phenol. The purified eDNA fragments were cloned into the Bluescript plasmid (Stratagene (TM)). The complete sequence of the yeast acetyl-CoA hydrolase cDNA was determined by exonuclease III deletion (Henikoff, S., *Gene (Amst.)* 28:35 1–359 (1984)), the dideoxy chain termination method of Sanger (Sanger, F., et al., *J. Mol. Biol.* 94:441–448 (1975)) modified for double-stranded DNA sequencing by Guo et al. (Guo, L.-H., et al., *Nucleic Acids Res.* 11:5521–5539 (1983)), and specific priming with synthetic oligonucleotides. All restriction enzymes were purchased from New England Biolabs. RNA and DNA markers were obtained from Bethesda Research Laboratories. GeneScreen Plus membrane was from NEN. Poly(A)$^+$RNA was analyzed by RNA blot hybridization (Lehrach, H. et al., *Biochemistry* 16:4743–4751 (1977); Thomas, P. S., *Proc. Natl. Acad. Sci. USA* 77:5201–5202 (1980)). Genomic DNA was isolated from yeast (Sherman, F., et al., *Methods in Yeast Genetics*, Cold Spring Harbor Laboratory, Cold Spring Harbor, N.Y. (1986)), digested with restriction enzymes, and analyzed by DNA blot hybridization (Southern, E. M., *J. Mol. Biol.* 98:503–517 (1975)). The chromosome bearing the ACH1 gene was identified by hybridization of labelled cDNA with a Saccharomyces chromo-di-hybridizer (Clonetech) (i.e., a yeast chromosomal agarose gel).

In this manner, the complete nucleotide sequence, both orientations, of pBA4 and pBA5 were determined using exonuclease III deletions and the double-stranded dideoxy chain termination method. The nucleotide sequence of the yeast acetyl-CoA hydrolase cDNA is shown in FIG. 7C (SEQ. ID No. 5). Compared with pBA5, pBA4 lacks 266 bp from the 3' end and extends 537 bp further toward the 5' end. Together both cDNAs contain a long open reading frame extending from nucleotide 1 to 1578 which encodes all 16 tryptic peptides (FIG. 7; SEQ. ID No. 6). The location of the initiator methionine was assigned based on the fact that there are no intervening methionine residues between this residue and the first identified tryptic peptide and that there is an in-frame termination codon (nucleotides -93 to -91) preceding this proposed site of initiation.

RNA, DNA, and Chromosomal Blot Analyses

Total RNA (10 μg) was electrophoresed on a 1.2 % agarose/formaldehyde gel (Lehrach, H. et al., *Biochemistry* 16:4743–4751 (1977); Thomas, P. S., *Proc. Natl. Acad. Sci. USA* 77:5201–5202 (1980)). The RNA was transferred onto a GeneScreen Plus membrane and hybridized with random-primed, [$^{32}$P]-labeled cDNA (derived from pBA4) and yeast β-tubulin probes for 24 hr, washed, and autoradiographed. RNA blot analysis of yeast poly(A)$^+$ mRNA using a random-primed, [$^{32}$P]-labelled cDNA probe, either pBA4 or pBA5, revealed a 2.5 kb RNA band. DNA blot analysis of restriction enzyme digested yeast genomic DNA with the same probes was performed. The restriction fragments were electrophoresed on a 0.8% agarose gel in Tris-borate buffer. The DNA was transferred onto a GeneScreen Plus membrane and hybridized with random primed, [$^{32}$P]-cDNA (derived from pBA4) for 24 hr and washed (Southern, E. M., *J. Mol. Biol.* 98:503–517 (1975)). The experiment revealed a fragment pattern consistent with a single copy gene encoding the sequences present in the cDNA. Chromosomal analysis was conducted. An agarose gel of yeast chromosomal DNA was hybridized with random primed, [$^{32}$P]-cDNA (derived from pBA4) for 24 hr and washed according to the manufacturer's recommendations. This analysis indicated that the yeast acetyl-CoA hydrolase gene (ACH1) is located on chromosome II.

Hydrophobicity Profile for Acetyl-CoA Hydrolase

Figure 8:
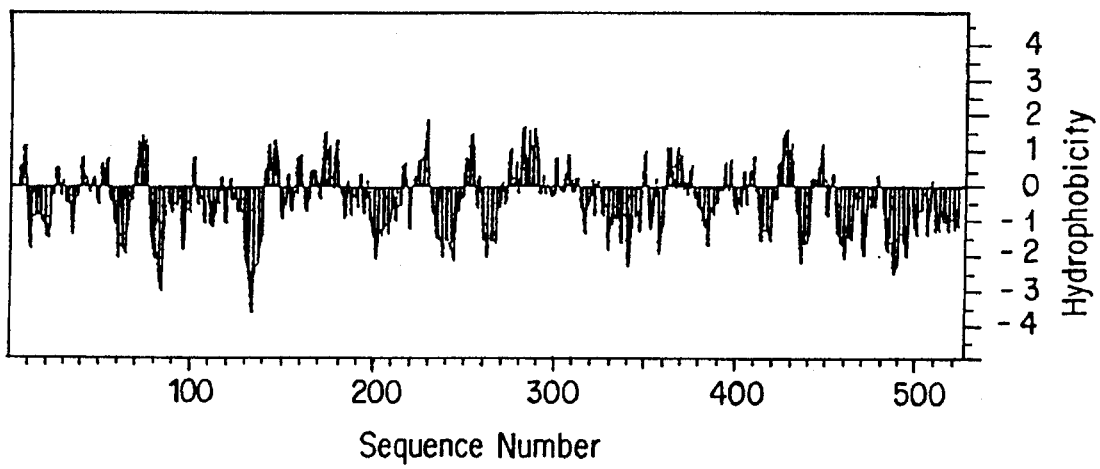
FIG. 8 shows the hydrophobicity profile of the acetyl-CoA hydrolase as determined using the algorithm of Kyte and Doolittle (Kyte, J., et al., J. Mol. Biol. 157:105–132 (1982)) with a window size of 9.

The hydrophobicity profile was determined using the algorithm of Kyte and Doolittle (Kyte, J., et at., *J. Mol. Biol.* 157:105–132 (1982)) with a window size of 9 (FIG. 8). The profile shows the presence of three extended hydrophilic regions at positions 77–140, 312–362, and 455–526.

Comparison of cDNA and Protein Sequence Data for Yeast Acetyl-CoA Hydrolase with DNA and Protein Sequence Databases A computer search of the GenBank database was conducted using the FASTA programs, described by Pearson and Lipman (Pearson, W. R., et al., *Proc. Natl. Acad. Sci. USA* 85:2444–2448 (1988)). Comparisons between the protein sequence of yeast acetyl-CoA hydrolase and other protein sequences in the Swiss Protein database were also conducted. There were no significant similarities ($\leq 30\%$) revealed by either comparison.

Yeast AcetVl-CoA Hydrolase is a Mannose-containing Glycoprotein

The calculated molecular weight for acetyl-CoA hydrolase derived from cDNA sequence (58,369 daltons) is smaller than the $M_r$-determined from SDS-PAGE (65,000±2,000) (Lee, F.-J.S., et al., *Eur. J. Biochem.* 184:21–28 (1989)). In order to determine whether this disparity could be attributed to acetyl-CoA hydrolase being a glycoprotein, the presence of a carbohydrate moiety on acetyl-CoA hydrolase was assessed using a lectin-binding method. Biotinylated lectins, Conconavalin A (ConA) (binds to α-mannose), *Sophora japonica* agglutinin (SJA, binds to galactose and N-acetylgalactosamine), and *Pisum sativum* agglutinin (PSA, binds to α-mannose and N-acetylchitobiose linked to α-fucose) were purchased from Vector Laboratories (Burlington, Calif.), and the lectin binding assay was carried out as recommended by the manufacturer. Briefly, protein was adsorbed onto nitrocellulose membrane by dot-blotting and incubated initially with 10 μg/ml biotinylated lectin and avidin-biotinylated horseradish peroxidase complex. The calorimetric detection was with 4-chloro-1-naphthol and $H_2O_2$. Bovine serum albumin (type V, Sigma) (50 μg) was used as a negative control.

ConA, but not SJA and PSA, bound to yeast acetyl-CoA hydrolase indicating that the enzyme contains α-mannose and is an intracellular glycoprotein.

In summary, yeast acetyl-CoA hydrolase is encoded by an open reading frame of 1578 bases and consists of 526 amino acids. The molecular weight calculated from the amino acid composition is 58,369 daltons, which is smaller than the previously determined $M_r$ of 65,000±2,000 (Lee, F.-J.S., et al., *Eur. J. Biochem.* 184:21–28 (1989)). We have demonstrated that yeast acetyl-CoA is a mannose-containing glycoprotein, and our results indicate that the presence of such a carbohydrate moiety accounts for the difference between the theoretical and observed molecular masses. Acetyl-CoA hydrolase contains 3 putative N-glycosylation sites (i.e., Ans-X-Ser (or Thr) sequences) at residues 314–316, 381–383, 386–388. Previous protein sequence analysis of the native protein revealed it to be N-terminally blocked (Lee, F.-J.S., et al., *Eur. J. Biochem.* 184:21–28 (1989)), and it appears that the N-terminal residue of acetyl-CoA hydrolase is an $N^\alpha$-acetylated threonyl residue. A comparison of the protein sequences of acetyl-CoA hydrolase to other protein sequences in the data bank failed to reveal any appreciable percent similarity with any protein in the Swiss Protein database.

The RNA, DNA and chromosomal blot hybridizations indicate that there is a single 2.5 kb mRNA and a single gene (ACH1) encoding acetyl-CoA hydrolase located on chromosome II.

EXAMPLE 3

Alternative Methods of Cloning and Expressing Acetyl-CoA Hydrolase

The DNA sequence coding for acetyl-CoA hydrolase may be obtained in a variety of ways. For example, mRNA coding for acetyl-CoA hydrolase may be isolated from yeast, or from other sources and identified using Northern blots (Alwine et al., *Method Enzymol.* 68:220–242 (1979)). Probes for Northern analyses may be synthesized based upon the amino acid sequence of peptides from acetyl-CoA hydrolase described above. The mRNA may then be converted to cDNA by techniques well-known to those skilled in the art (Sambrook et al., *Molecular Cloning, A Laboratory Manual*, chapter 8 (1989)). Alternatively, degenerate DNA probes may be used to screen genomic or cDNA libraries of a species that produces acetyl-CoA hydrolase (Id., chapters 8 and 9).

DNA probes may be labeled with any group having a detectable physical or chemical property. Particularly useful are enzymatically active groups, such as enzymes (see *Clin. Chem.* 22:1243 (1976)), enzyme substrates (see British Pat. Spec. 1,548,741), coenzymes (see U.S. Pat. Nos. 4,230,797 and 4,238,565) and enzyme inhibitors (see U.S. Pat. No. 4,134,792); florescent compounds (see *Clin. Chem.* 25:353 (1979)); chromophores; luminescent compounds (see *Clin. Chem.* 25:512 (1979)); ligands; proximal interacting pairs; and radioisotopes such as $^3H$, $^{35}S$, $^{32}P$, $^{125}I$ and $^{14}C$. Such labels and labeling pairs may be detected based upon their own physical properties (e.g., chromophores and radioisotopes) or based upon their reactive or binding properties (e.g., enzymes, substrates, coenzymes and inhibitors).

DNA sequences encoding acetyl-CoA hydrolase may be recombined with vector DNA in accordance with conventional techniques (Sambrook et al., *Molecular Cloning, A Laboratory Manual*, chapters 1–4 (1989)). Vectors with transcriptional and translational signals recognized by an appropriate host may be used to express the enzyme.

Hosts may be mammalian cells capable of culture in vitro or in vivo, bacteria or fungi. Mammalian cells which may be useful as hosts include cells of fibroblast origin such as VERO or CHO-K1, or cells of lymphoid origin, such as the hybridoma SP2/O-AG14 or the myeloma P3×63Sgh, and their derivatives.

Procaryotic cells may also serve as hosts. Bacterial hosts of particular interest include *E. coli* K12 strain 294 (ATCC 31446), *E. coli* X1776 (ATCC 31537), *E. coli* W3110 (F⁻, lambda⁻, phototropic (ATCC 27325)), and other enterobacteria such as *Salmonella typhimurium* or *Serratia marcescens*, and various Pseudomonas species. In these hosts, the acetyl-CoA hydrolase acetyltransferase will not be glycosylated.

In general, vectors will contain replication and control sequences which are recognized by the host cell. Vectors will also ordinarily carry specific genes which are capable of providing a means for the phenotypic selection of transformed cells. The expression of the acetyl-CoA hydrolase DNA can be placed under control of regulatory sequences which are homologous to the organisdn in its untransformed state. For example, the *E. coli* lac operon mediates lactose utilization by expressing the enzyme β-galactosidase. The lac control elements may be obtained from bacteriophage lambda plac5, which is infective for *E. coli*. The lac promoter-operator system can be induced by IPTG. Other promoter/operator systems or portions thereof can be employed as well. For example, colicin E1, galaclose, alkaline phosphatase, tryptophan, xylose, tax, and the like can be used.

For mammalian hosts, several possible vector systems are available for expression. One class of vectors utilizes DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or markers which allow selection of host cells containing the expression vector. The marker may provide for prototropy in an auxotrophic host, biocide resistance or the like. The selectable marker gene can either be directly linked to the DNA sequences to be expressed or introduced into the same host cell by co-transformation.

Additional elements may also be included in expression vectors. These elements may include splice signals, as well as transcription promoters, enhancers, and termination signals. Expression vectors incorporating such elements include those described by Okayarea (*Mol. Cel. Biol.* 3:280 (1983)) and others. A wide variety of transcriptional and translational regulatory sequences may be employed, depending on the nature of the host. The transcriptional and translational signals may be derived from viral sources, such as adenovirus, bovine papilloma virus, simian virus, or the like, where the regulatory signals are associated with a particular gene that has a high level of expression. Alternatively, promoters from mammalian expression products, such as actin, collagen, myosin, etc., may be employed. Inducible or repressible promoters may also be used in order to allow the expression of genes to be modulated. Such promoters may be temperature-sensitive (i.e. by varying the temperature, expression can be repressed or initiated), or subject to chemical regulation, e.g. by metabolites.

Once appropriate gene/vector constructs have been prepared, the constructs may be introduced into an appropriate host. Various techniques may be employed, such as protoplast fusion, calcium phosphate precipitation, electroporation or other conventional techniques. After transformation, cells are grown and screened for appropriate activities.

The host cells for acetyl-CoA hydrolase production may be immortalized cells, e.g. myeloma or lymphoma cells. These cells may be grown in an appropriate nutrient medium in culture flasks or injected into a synergistic host, e.g., mouse or rat, or an immunodeficient host or host site, e.g. the nude mouse or hamster pouch.

The acetyl-CoA hydrolase of the invention may be isolated and purified in accordance with conventional techniques such as extraction, precipitation, chromatography, electrophoresis, and the like.

EXAMPLE 4

Uses of Acetyl-CoA Hydrolase

Pharmaceutical Uses

Acetyl-CoA hydrolase, once produced and purified, may be used in pharmaceuticals. For example, the enzyme may be used to inhibit acetylation of platelets, thus increasing clotting time.

Expression of Acetyl-CoA Hydrolase in Plants

Acetyl-CoA hydrolase can be introduced into plants by genetic engineering techniques. Expression in plants may be used as a means for blocking the acetylation of herbicides. In this way, plants with increased herbicide tolerance may be produced.

The coding region for an acetyl-CoA hydrolase gene that may be used in this invention may be homologous or heterologous to the plant cell being transformed. It is necessary, however, that the genetic sequence coding for acetyl-CoA hydrolase be expressed as a functional protein or polypeptide in the resulting plant cell.

DNA from either genomic DNA or cDNA encoding acetyl-CoA hydrolase may be used in this invention. The acetyl-CoA hydrolase gene may also be constructed partially of a cDNA clone and partially of a genomic clone. In addition, the DNA coding for the acetyl-CoA hydrolase gene may comprise portions from various species.

In a preferred embodiment, the promoter of the acetyl-CoA hydrolase gene is used to express the gene for the enzyme. Other promoters that may be used include nos, ocs, and CaMV promoters. Overproducing plant promoters may also be used. Such promoters, operably linked to the acetyl-CoA hydrolase gene, should increase the expression of acetyl-CoA hydrolase and produce transformed plants with an increased tolerance for herbicides. Overproducing plant promoters that may be used in this invention include the promoter of the small subunit (ss) of ribulose-1,5-biphosphate carboxylase from soybean (Berry-Lowe et al., *J. Molecular and App. Gert.* 1:483–498 (1982), and the promoter of the chlorophyll a/b binding protein. These two promoters are known to be light-induced in eukaryotic plant cells (see, for example, *Genetic Engineering of Plants, an Agricultural Perspective*, A. Cashmore, Plenum, New York 1983, pages 29–38; Corruzi, G. et al., *J. of Biol. Chem.* 258:1399 (1983); and Dunsmuir, P. et al., *J. of Mol. and Applied Genet.* 2:285 (1983)).

Genetic sequences comprising an acetyl-CoA hydrolase gene operably linked to a plant promoter may be joined to secretion signal sequences and the construct ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells, typically antibiotic resistance genes.

The genetic construct for expressing acetyl-CoA hydrolase can be microinjected directly into plant cells by use of micropipettes to mechanically transfer the recombinant DNA. The genetic material may also be transferred into plant cells using polyethylene glycol to form a precipitation complex with the genetic material that is taken up by cells. (Paszkowski et al., *EMBO J.* 3:2717–22 (1984)). The acetyl-CoA hydrolase gene may also be introduced into plant cells by electroporation. (Fromm et al., "Expression of Genes Transferred into Monocot and Dicot Plant Cells by Electroporation," *Proc. Nat'l. Acad. Sci. U.S.A.* 82:5824 (1985)). In this technique, plant protoplasts are electroporated in the presence of plasmids containing the acetyl-CoA hydrolase genetic construct. Electrical impulses of high field strength reversibly permeabilize biomembranes allowing the introduction of plasmids. Electroporated plant protoplasts reform cell walls, divide, and form plant calli. Selection of the transformed plant cells expressing acetyl-CoA hydrolase can be accomplished using phenotypic markers as described above.

Another method of introducing the acetyl-CoA hydrolase gene into plant cells is to infect cells with *Agrobacterium tumefaciens* transformed with the acetyl-CoA hydrolase gene. Under appropriate conditions well-known in the art, transformed plant cells are grown to form shoots, roots, and develop further into plants. The acetyl-CoA hydrolase genetic sequences can be joined to the Ti plasmid of *Agrobacterium tumefaciens*. The Ti plasmid is transmitted to plant cells on infection by *Agrobacterium tumefaciens* and is stably integrated into the plant genome. Horsch et al., "Inheritance of Functional Foreign Genes in Plants," *Science* 233:496–498 (1984); Fraley et al., *Proc. Nat'l Acad. Sci. U.S.A.* 80:4803 (1983)).

There are presently two different ways to transform plant cells with Agrobacterium:

(1) co-cultivation of Agrobacterium with cultured, isolated protoplasts, or (2) transformation of cells or tissues with Agrobacterium. Method (1) requires an established culture system that allows culturing protoplasts and plant regeneration from cultured protoplasts. Method (2) requires that the plant cells or tissues can be transformed by Agrobacterium and that the transformed cells or tissues can be induced to regenerate into whole plants. In the binary system, to have infection, two plasmids are needed: a T-DNA containing plasmid and a vir plasmid.

All plants from which protoplasts can be isolated and cultured to give whole regenerated plants can be used for the expression of acetyl-CoA hydrolase. Suitable plants include, for example, species from the genera Pragaria, Lotus, Medicago, Onobrychis, Trifolium, Trigonella, Vigna, Citrus, Linum, Geranium, Manicot, Daucus, ArabidOpsis, Brassica, Raphanus, Sinapis, Atropa, Capsicum, Datura, Hyoscyamus, Lycopersion, Nicotiana, Solanum, Petunia, Digitalis, Majoraria, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lollum, Zea, Triacum, Sorghum, and Datura. Additional plant genera that may be transformed by Agrobacterium include lpomoea, Passifiora, Cyclamen, Malus, Prunus, Rosa, Rubus, Populus, Santalum, Allium, Lilium, Narcissus, Ananas, Arachis, Phaseolus, and Pisum.

Plant regeneration from cultured protoplasts is described in Evans et al., "Protoplast Isolation and Culture," in *Handbook of Plant Cell Culture* 1:124–176 (MacMillan Publishing Co., New York, 1983); M. R. Davey, "Recent Developments in the Culture and Regeneration of Plant Protoplasts," *Protoplasts, 1983—Lecture Proceedings*, pp. 19–29 (Birkhauser, Basel, 1983); P. J. Dale, "Protoplast Culture and Plant Regeneration of Cereals and Other Recalcitrant Crops," in *Protoplasts 1983—Lecture Proceedings*, pp. 31–41 (Birkhauser, Basel, 1983): and H. Binding, "Regeneration of Plants," in *Plant Protoplasts*, pp. 21–37 (CRC Press, Boca Raton, 1985).

Techniques for the regeneration of plants varies from species to species but generally, a suspension of transformed protoplasts containing multiple copies of the acetyl-CoA hydrolase gene is first provided. Embryo formation can then be induced from the protoplast suspensions, to the stage of ripening and germination as natural embryos. The culture media will generally contain various amino acids and hormones, such as auxins and cytokines. It is also advantageous to add glutamic acid and proline to the medium, especially for such species as corn and alfalfa.

Mature plants, grown from transformed plant cells, are selfed to produce an inbred plant. The inbred plant produces seed containing the recombinant DNA sequences promoting increased expression of acetyl-CoA hydrolase. These seeds can be grown to produce plants that have an enhanced ability to block the acetylation of herbicides.

Inbred plants can be used to develop herbicide tolerant hybrids. In this method, a herbicide tolerant inbred line is crossed with another inbred line to produce the hybrid. In diploid plants, typically one parent is transformed by the acetyl-CoA hydrolase genetic sequence and the other parent is of wild type. After crossing the parents, the first generation hybrids (F1) will show a distribution of ½ acetyl-CoA hydrolase/wild type: ½ acetyl-CoA hydrolase/wild type. These first generation hybrids (F1) are selfed to produce second generation hybrids (F2). The genetic distribution of the F2 hybrids are ¼ acetyl-CoA hydrolase/acetyl-CoA hydrolase: ½ acetyl-CoA hydrolase/wild type: ¼ wild type/wild type. The F2 hybrids with the genetic makeup of acetyl-CoA hydrolase/acetyl-CoA hydrolase are chosen as the herbicidal tolerant plants.

Parts obtained from regenerated plants, such as flowers, seeds, leaves, branches, fruit, and the like are covered by the invention provided that these pans comprise the herbicidal tolerant cells. Progeny and variants, and mutants of the regenerated plants are also included within the scope of this invention. As used herein, variant describes phenotypic changes that are stable and heritable, including heritable variation that is sexually transmitted to progeny of plants, provided that the variant still comprises a herbicidal tolerant plant through enhanced rate of acetylation. Also, as used herein, mutant describes variation as a result of environmental conditions, such as radiation, or as a result of genetic variation in which a trait is transmitted meiotically according to well-established laws of inheritance.

EXAMPLE 5

Glucose-Repression of A CHI Expression

In an attempt to understand the regulation of ACH1 gene expression, the levels of ACH1 mRNA and acetyl-CoA hydrolase activity were measured in different growth phases and the effects of various carbon sources on the levels of ACH1 mRNA expression was examined.

Cells from 500 ml yeast cultures were harvested at different stages of growth in complete medium containing glucose and at mid-log phase in complete medium containing glucose, glycerol, galactose, or potassium acetate. Total RNA was extracted from each sample (Sherman, F., et al., *Methods in Yeast Genetics,* Cold Spring Harbor Laboratory, Cold Spring Harbor, N.Y. (1986)). Yeast RNA (10 μg) was electrophoresed on a 1.2% agarose/formaldehyde gel (Lehrach, H. et al., Biochemistry 16:4743–4751 (1977); Thomas, P. S., *Proc. Natl. Acad. Sci. USA* 77:5201–5202 (1980)). The mRNA was transferred onto a GeneScreen Plus membrane and hybridized separately with random-primed, [$^{32}$P]-labelled cDNA (derived from pBA4) and β-tubulin (Neff, N. F., et al., *Cell* 33:211–219 (1983)) DNA for 24 hr, washed, and autoradiographed. The relative levels of mRNA expression of ACH1 and β-tubulin were determined.

Total RNA, isolated from the early log, late log, and stationary phase yeast cultures, was run on a formaldehyde/agarose gel, transferred onto a GeneScreen Plus (TM) membrane, and hybridized with a [$^{32}$P]-labeled pBA4 cDNA insert. The blot membrane was also hybridized with yeast tubulin as an internal control. The ACH1 mRNA and enzyme activity were increased in stationary phase but were decreased in early and late log phases.

Additional RNA blot analyses of total RNA prepared from mid-log yeast cultures grown in either glucose, glycerol, galactose, or acetate-containing medium were also performed. The ACH1 mRNA level of yeast grown in glucose was barely detectable and was much less than the mRNA levels of yeasts grown in medium containing glycerol, galactose, or acetate. In addition, acetyl-CoA hydrolase activity is much higher when yeast are grown in medium containing glycerol, galactose or acetate as compared with glucose. Moreover, the addition of glucose to galactose to glycerol medium caused a rapid reduction in ACH1 mRNA level, and within two hours after addition of glucose, the ACH1 mRNA level was reduced to that of yeast grown in glucose medium. In contrast, the addition of glycerol of galactose into glucose medium did not increase the level of ACH1 mRNA.

Thus, the mRNA level and enzyme activity of acetyl-CoA hydrolase are markedly reduced in glucose-containing medium and increased in glucose-free medium indicating that the expression of ACH1 gene is repressed by glucose. Since acetyl-CoA hydrolase is highly expressed in the stationary phase and in medium containing non-fermentable carbon sources (glycerol, galactose, and acetate), it appears that under conditions of limited nutrition a large amount of acetyl-CoA is likely generated form fatty acids or amino acids and that it is not effectively incorporated into the TCA cycle. Such an excess of acetyl-CoA could lead to autoacetylation of proteins, as well as to the generation of toxic ketone bodies and other noxious metabolites. It is thus possible that the intracellular level of acetyl-CoA could be regulated at a "safe" level by hydrolysis of excessive acetyl-CoA by acetyl-CoA hydrolase.

The concentration of acetyl-CoA in cells is primarily regulated by its rate of synthesis and its utilization in various metabolic pathways. The role of such enzymes catalyzing the scission of acetyl-CoA's high energy thioester bond with no apparent metabolic advantage represents a biochemical conundrum. Several functions for acetyl-CoA hydrolases from higher eukaryotes have been proposed. First, the cytoplasmic form of the enzyme may be involved in the maintenance of the cytosolic acetyl-CoA concentration and CoASH pool for both fatty acid and cholesterol synthesis and fatty acid oxidation (Prass, R. L., et al., *J. Biol. Chem.* 255:5215–5223 (1980); Ebisuno, S., et al., *Am. J. Physiol.* 255:R724–R730 (1988)). Second, the mitochondrial form of the enzyme may be involved in the regulation of acetylation during melatonin synthesis in the pineal gland (Namboodiri, M. A. A., et al., *J. Biol. Chem.* 255:6032–6035 (1980)). However, in neither of these cases has a specific biological function for acetyl-CoA hydrolase been firmly established.

Furthermore, although it is known that $N^{\alpha}$-acetylation reduces that rate of protein turnover, it is unclear how the intracellular concentration of acetyl-CoA relates to the rate of $N^{\alpha}$-acetylation. Appropriate manipulation of the ACH1 gene may shed light on this important question.

EXAMPLE 6

Identification of the Glucose Repressible Regulatory Element

Cloning of Genomic DNA

A yeast genomic library was screened with random-primed, $^{32}$P-labeled Acetyl-CoA hydrolase cDNA fragments. Positive phage were purified and their DNA isolated. Isolated phage DNA was digested with restriction enzymes and the resulting fragments were separated by agarose gel electrophoresis. Separated fragments were transferred onto a GeneScreen membrane and allowed to hybridize to a $^{32}$P-labeled probe that had been isolated form the 5' end of the acetyl-CoA hydrolase cDNA clone pAB4. The probe DNA was obtained by cleaving pAB4 with XhoI and XbaI. A three kb fragment which contains the acetyl-CoA hydrolase promoter was subcloned into Bluescript and named pG1E2. The insert of the Bluescript plasmid was completely sequenced by double strand sequencing using the ExoIII deletion strategy (Henikoff, S., *Gene* 28:351–359 (1984)).

Figure 9:
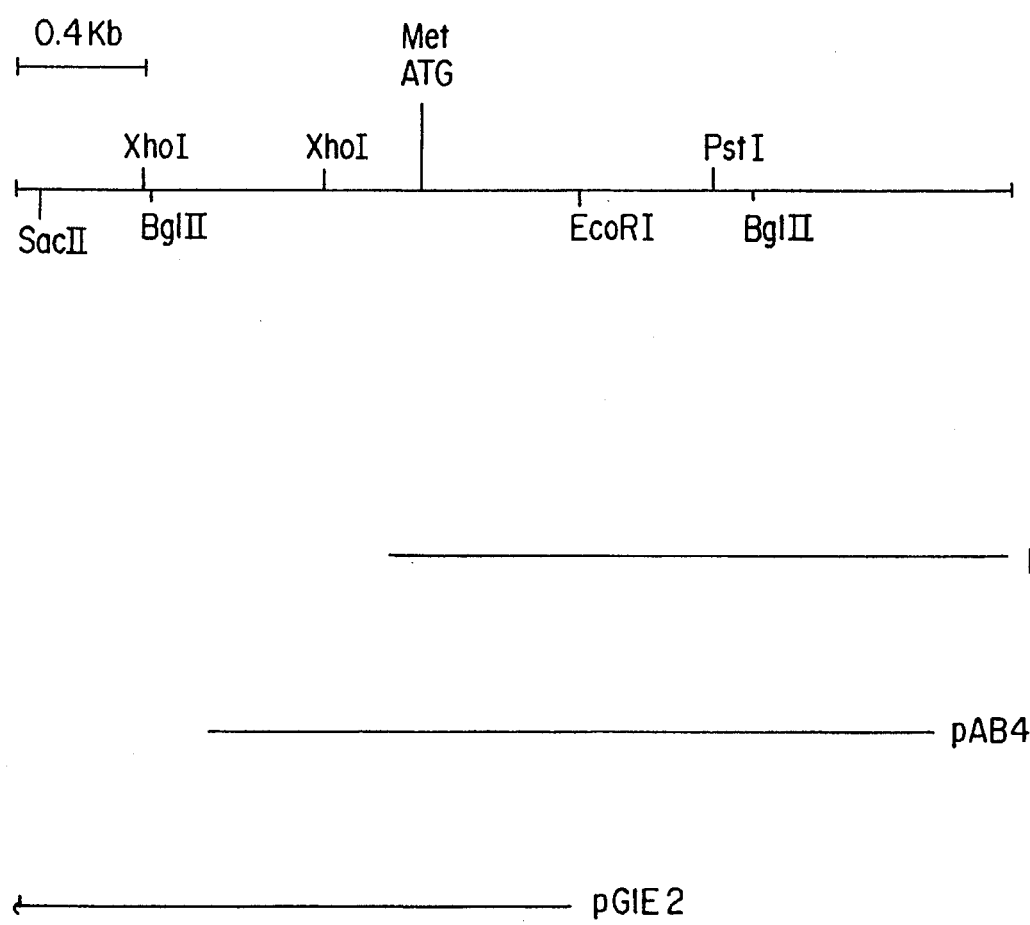
FIG. 9 shows the restriction sites in phage DNA containing the genomic clone of the acetyl-CoA hydrolase gene. Also shown, is the relative location of the cDNA clones pAB4 and pAB5, as well as the location of the genomic clone pG1E2.

FIG. 9 shows the restriction sites in the isolated phage DNA and the relative locations of pAB5, pAB4 and pG1E2. FIG. 10A–10E shows the nucleotide sequence of the ADH1 genomic DNA (SEQ. ID No. 7). This gene contains no introns. Therefore, the coding portions of the genomic clones and cDNA clones are the same (compare FIG. 7, SEQ. ID No. 6 and FIG. 10, SEQ. ID No. 8).

Figure 11:
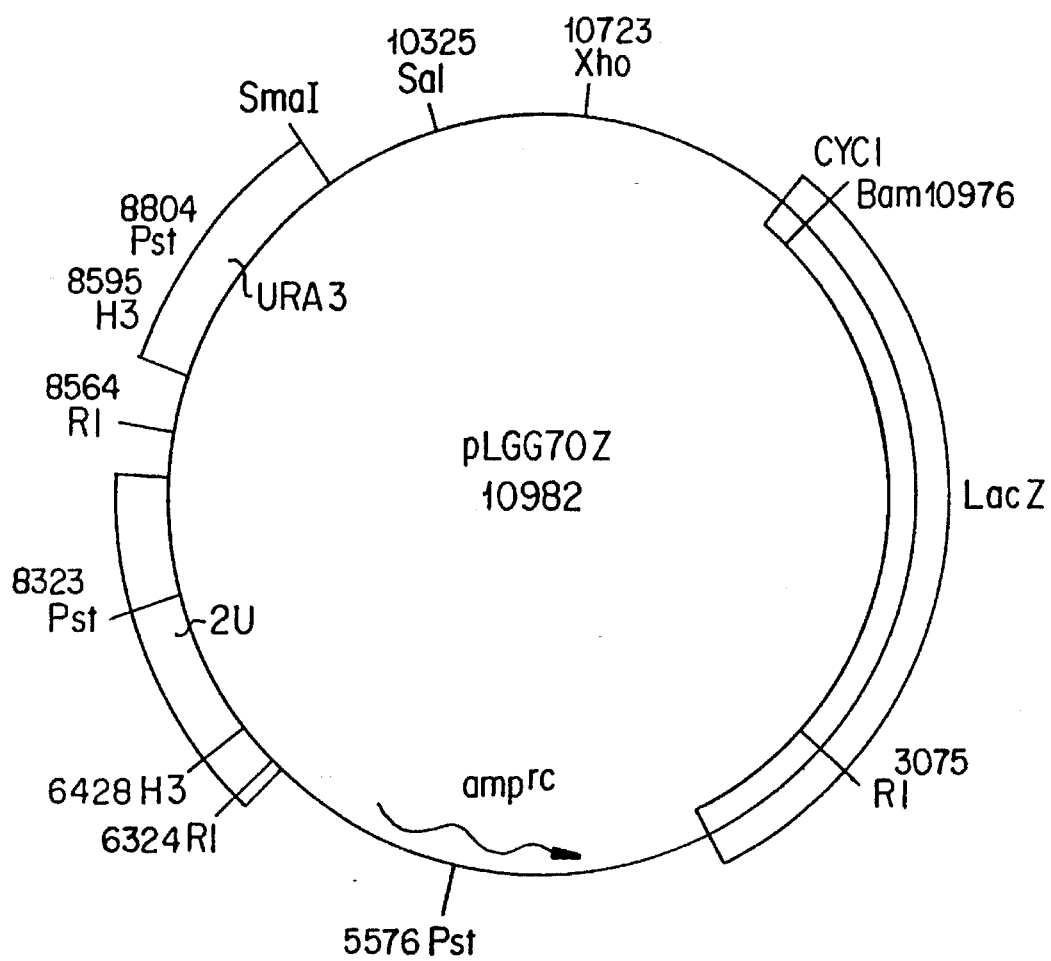
FIG. 11 is a schematic drawing showing the restriction sites of the plasmid pGL670Z. This plasmid was used in examining deletion mutants for the presence of the glucose repressible promoter. Cyc1 upstream region with unique Sal and Xho sites upstream of cyc1/lacZ fusion. *Guarante and Mason*, Cell 32:1279, April 1983. Number 52, ME-pL6670Z; size—~11 Kb; made by—L. Guarante; Markers—$amp^R$, URA3.

Construction of Deletion Mutants pLG670Z (Guarente et al., *Proc. Natl. Acad. Sci. USA* 78:2199–2203 (1981); Guarente, L., *Meth. Enzymol.* 101:181–191 (1983)) was obtained from Dr. Guarente at the Massachusetts Institute of Technology and is shown schematically in FIG. 11. An XhoI-BglII fragment of acetyl-CoA hydrolase cDNA was cloned into XhoI/BamHI double digested pLG670Z to create pLG670Z-I, the source for deletion mutants. Plasmid pLG670Z-I bears an inframe fusion of lacZ and the portion of the acetyl-CoA hydrolase gene coding for the amino terminus of the protein.

Deletion mutants were generated using either ExoIII or Bal31 as described in Sambrook et al., *Molecular Cloning, A Laboratory Manual,* vol. 2, chapter 15 (1989). The deleted products were sequenced in the Bluescript plasmid as described above. A PvuII-XhoI fragment was isolated from the Bluescript plasmid and cloned into pLG670-I that had been digested with SmaI and XhoI. The resulting plasmid was first transformed into the *E. coli* strain DK1 in order to produce a large quantity of plasmid and then transformed into *Saccharomyces cerevisiae* strain 502 or 4C.

β-Galactosidase Assay

Yeast cultures were grown to mid-log phase in either 2 % glucose, 2% galactose or 3% glycerol medium and the absorbance of cultures at 600 nm was determined. Cells were pelleted by centrifugation, washed with H$_2$O, resuspended in 5 ml. of Z buffer (0.06 M Na$_2$HPO$_4$, 0.04 M NaH$_2$PO$_4$, 0.01 M KCl, 0.001 M MgSO$_4$, 0.05 M β-mercaptoethanol) and vortexed in the presence of glass beads. Extracts were then assayed for O-nitrophenol-β-D-galactoside hydrolyzing activity in Z buffer (Miller, J. H., *Experiments in Molecular Genetics,* Cold Spring Harbor Laboratory, pp. 352–355; Guarente, *Meth. Enzymol.* 101:181–191 (1983)). The results obtained for various deletion routants are shown in FIG. 12. Protein concentrations were determined by the method of Bradford (*Anal. Biochem.* 72:248–254 (1976)). A unit of specific activity is defined in term of μmoles O-nitrophenol/min/mg protein.

Identification of DNA Sequences Regulating Gene Expression

Yeast transformed with DNA fragments containing the glucose-repressible promoter should show less β-galactosidase activity when grown in 2% glucose-containing medium than in medium containing 2% galactose or 3 % glycerol. When a deletion results in the elimination of the promoter, β-galactosidase activity should be lost in all yeast, regardless of the growth medium.

The inventors have numbered nucleotides such that the "A" of the "ATG" start site of translation is nucleotide number 1. Reading 3 prime from this point, nucleotides are given positive numbers and reading 5 prime, they are given negative numbers. Using this system, it was found that deleting DNA beyond nucleotide -296 caused a complete loss of enzymatic activity in all cells. Therefore, the glucose-repressible promoter lies 5 prime of nucleotide -296.

In contrast, yeast containing genomic fragments in which DNA 5 prime of nucleotide -468 was deleted showed 0.11 units of activity when grown in medium containing glucose, 60.0 units when grown in medium containing glycerol and 28.4 units when grown in medium containing galactose. Elevated enzymatic activity in galactose or glycerol grown cells relative to glucose grown cells was also seen with deletions of DNA 5 prime of nucleotides -790, -477 and -475. It may be concluded that the glucose repressible promoter is between nucleotide -296 and nucleotide -468. This sequence is shown in FIG. 13 as SEQ. Id No. 11.

Results for the deletion of DNA 5 prime of nucleotide -435 are more difficult to interpret. Although the amount of enzymatic activity in the glucose grown cells is still much lower than the activity evidenced by their glycerol or galactose grown counterparts, the amount has doubled compared to the activity given by cells containing deletions 5 prime of nucleotide -468 and grown in glucose. This may indicate a partial loss of the promoter. Alternatively, the result may simply reflect assay variability.

The glucose-repressible promoter of the invention may be operably linked to any coding sequence. For example, the coding sequence of a hormone, structural protein, or growth factor may be used, such as that for fibronectin, insulin, insulinlike growth factor, alveolar marcophage-derived growth factor, laminin, basic fibroblast growth factor, acidic fibroblast growth tactor, PDGF, EGF, collagen, thrombospondin, heparin, Transformation growth factor-α, Transformation growth factor-β,int-2, endothelial cell growth factor, heparin-binding growth factor-1, Kaposi sarcoma FDF, Fibroblast growth factor-5, Fibroblast growth factor-6, Hst-1 related gene, keratinocyte growth factor, integrin, anchorin, lipocortin, calpactin, calmodulin. The promoter of the invention may also be operably linked to transcription factors so as to indirectly control the transcription of a different gene that is the target of such transcription factor. Such transcription factors include those transcription factors classified as eukaryotic Helix-turn-helix proteins, the homeodomains (such as MATα2, MATα1, oct-2, unc-86, ubx, eve, ftz, ANtp, and en), zinc finger proteins (such as TFIIIa-1, TFIIIa-2, TFIIIa-3, SPI-1, SP1-2, SP1-3, zif268-1, zif268-2 and zif268-3), the steriod receptor proteins (including receptors for steroid hormones, retinoids, vitamin D, estrogen, androgen, glucocorticoid, progesterone, knirps, nur77 and thyroid hormones), leucine zipper promins (such as c/EBP, Ig/EBP-1, CREB, c-FOS, c-JUN, GGN4, Opaque2, sis-A, Cys-3), and the helix-loop-helix proteins (such as n-myc, c-myc, myoD, daughterless, e12, e47, T4 achaete-scute and T5 achaete-scute).

Although the foregoing refers to particular preferred embodiments, it will be understood that the present invention is not so limited. It will occur to those of ordinary skill in the art that various modifications may be made in the disclosed embodiments and such modifications are intended to be within the scope of the present invention.

---

What is claimed is:

1. An isolated DNA Sequence having DNA SEQ ID NO: 11.

2. A recombinant construct comprised of DNA SEQ ID NO: 11 flanked on at least one side by a DNA sequence that is not naturally associated with SEQ ID NO: 11.

3. A DNA vector comprised of the recombinant construct of claim 2.

4. The vector of claim 3, wherein said vector further comprises a coding sequence whose expression is under the control of SEQ ID NO: 11.

5. A yeast host cell transformed with the vector of claim 3 or 4.

6. The vector of claim 3, wherein said vector further comprises an antisense fragment whose expression is regulated by SEQ ID NO: 11.

7. The host cell as claimed in claim 5, wherein said host is *S. cerevisiae*.

8. The DNA vector as claimed in claim 3, wherein said vector is a yeast vector.

9. The DNA vector as claimed in claim 3, wherein said vector is selected from the group consisting of a plasmid and a phage.

10. The DNA vector as claimed in claim 9, wherein said vector is a plasmid.

11. The host cell of claim 5, wherein SEQ ID NO: 11 is integrated into said host cell's genome.

12. A method of regulating the expression of a protein in a controlled manner, said method comprising:

making a recombinant DNA construct comprised of a glucose-repressible promoter operably joined in a 5' to 3' direction of transcription to a DNA encoding said protein, wherein said glucose-repressible promoter comprises SEQ ID NO: 11 flanked on at least one side by DNA that is not naturally associated with SEQ ID NO: 11;

transforming said recombinant DNA construct into a yeast host cell;

(c) growing said yeast host cell in glucose-containing media sufficient to depress activity of SEQ ID NO: 11;

(d) transferring said yeast host cells to a glucose-free medium; and (e) expressing said protein under the control of said glucose-repressible promoter.

13. The method as claimed in claim 12, wherein the medium of step (d) contains glycerol or galactose.

14. The method of regulating the expression of an antisense sequence in a controlled manner, said method comprising:

making a recombinant DNA construct comprised of a glucose-repressible promoter operably joined in a 5' to 3' direction of transcription to an antisense sequence, wherein said glucose-repressible promoter comprises SEQ ID NO: 11 flanked on at least one side by DNA that is not naturally associated with SEQ ID NO: 11;

(b) transferring said recombinant DNA construct into a yeast host cell;

growing said host cell in glucose-containing medium sufficient to depress activity of SEQ ID NO: 11;

(d) transferring said host cells to a glucose-free medium; and (e) expressing said antisense sequence under the control of said glucose-repressible promoter.

15. The method of regulating the expression of an antisense sequence in a controlled manner as claimed in claim 14, wherein the medium of step (d) contains glycerol of galactose.

16. The vector as claimed in claim 3 wherein said vector is a linear vector.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

Phe Asn Leu Phe Val Gly Ala Ser Ala Gly Pro Glu Glu Asn Arg
   1               5                   10                  15

( 2 ) INFORMATION FOR SEQ ID NO:2:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2:

AAGTTGAACA AGCAACCACG AAGACGACCA GGTCTTCTTT TGTCT       45

( 2 ) INFORMATION FOR SEQ ID NO:3:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

Val Val Ala Ile Val Glu Ser Thr Met Arg
   1               5                   10

( 2 ) INFORMATION FOR SEQ ID NO:4:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:4:

CAACAACGAT AACAACTTAG GTGGTACTCT       30

( 2 ) INFORMATION FOR SEQ ID NO:5:

( i ) SEQUENCE CHARACTERISTICS:
      ( A ) LENGTH: 2466 base pairs
      ( B ) TYPE: nucleic acid
      ( C ) STRANDEDNESS: single
      ( D ) TOPOLOGY: linear ( i x ) FEATURE:
      ( A ) NAME/KEY: CDS
      ( B ) LOCATION: 614..2191

( x i ) SEQUENCE DESCRIPTION: SEQ ID NO:5:

```
GTTAGCCATC ATTATCATTA AAATATCAAC CCGAAGAACA ATGTATACAT ATACATATAC        60

GTACACATAT ACATATGTAC ATATGACATA CGTATTAGCC GCTGAGGACG CGGACGTATA       120

AAAGGACAAT ACTTATATGG AGCTAAGGGG AGCAGTTACG CAACTCCGTG ATCGCGCGCC       180

ACGGGCCGTC GGCGGCTGTT AATTGAAGAA AAAAAAATG AAGAACCACA AGGGGTGATC        240

CATATAGGTG ACTAGCATCA TCCCCTGCGA CGCGCGGCCC GCCGGGCAAA GGCGGGCAAT       300

GCGCGCTGCT GATTGGCCTC GAGGACAACG CCCTCAACCA CATCCGCAAC AGCCAATCCC       360

ATCGGAGCGT CAAACTACCA AAGTAGTGAT TGTATGGATC ACCACTGTAT TGTGGACGGT       420

AAGCGCTTGC TGGAGCAAAT GTGTAATCAA GTTGCTGTGT ATATATAGAC GTTAGATGTG       480

TTCTACCCCT TCTTTTGTCT TGTGCCCACC GGGCTTACAT TAGCACACAA AGCAGCAAGA       540

GACCGTCTTA CTAGACAATA GCGGCAAAAC AAACAACACA TTTCTTTTTT TCTTTTTCAC       600
```

| | | | | | | | | | | | | | | | | |
|---|---|---|---|---|---|---|---|---|---|---|---|---|---|---|---|---|
| ATATTGCACT AAA | ATG | ACA | ATT | TCT | AAT | TTG | TTA | AAG | CAG | AGA | GTT | AGG | | | | 649 |
| | Met | Thr | Ile | Ser | Asn | Leu | Leu | Lys | Gln | Arg | Val | Arg | | | | |
| | 1 | | | 5 | | | | | 10 | | | | | | | |
| TAT | GCT | CCC | TAT | CTG | AAA | AAA | GTT | AAG | GAA | GCT | CAC | GAG | CTT | ATT | CCA | 697 |
| Tyr | Ala | Pro | Tyr | Leu | Lys | Lys | Val | Lys | Glu | Ala | His | Glu | Leu | Ile | Pro | |
| | | 15 | | | | | 20 | | | | | 25 | | | | |
| TTG | TTC | AAG | AAT | GGT | CAG | TAC | CTT | GGG | TGG | TCC | GGT | TTT | ACA | GGA | GTG | 745 |
| Leu | Phe | Lys | Asn | Gly | Gln | Tyr | Leu | Gly | Trp | Ser | Gly | Phe | Thr | Gly | Val | |
| | 30 | | | | | 35 | | | | | 40 | | | | | |
| GGT | ACT | CCC | AAG | GCA | GTG | CCG | GAG | GCA | CTG | ATA | GAT | CAC | GTG | GAG | AAG | 793 |
| Gly | Thr | Pro | Lys | Ala | Val | Pro | Glu | Ala | Leu | Ile | Asp | His | Val | Glu | Lys | |
| 45 | | | | | 50 | | | | | 55 | | | | | 60 | |
| AAC | AAT | TTA | CAA | GGG | AAG | TTG | AGA | TTC | AAC | CTT | TTT | GTT | GGA | GCT | TCT | 841 |
| Asn | Asn | Leu | Gln | Gly | Lys | Leu | Arg | Phe | Asn | Leu | Phe | Val | Gly | Ala | Ser | |
| | | | | 65 | | | | | 70 | | | | | 75 | | |
| GCT | GGT | CCA | GAG | GAA | AAC | CGT | TGG | GCT | GAA | CAC | GAC | ATG | ATC | ATT | AAG | 889 |
| Ala | Gly | Pro | Glu | Glu | Asn | Arg | Trp | Ala | Glu | His | Asp | Met | Ile | Ile | Lys | |
| | | | 80 | | | | | 85 | | | | | 90 | | | |
| AGA | GCC | CCT | CAT | CAA | GTA | GGG | AAA | CCC | ATT | GCA | AAG | GCA | ATT | AAC | CAG | 937 |
| Arg | Ala | Pro | His | Gln | Val | Gly | Lys | Pro | Ile | Ala | Lys | Ala | Ile | Asn | Gln | |
| | | 95 | | | | | 100 | | | | | 105 | | | | |
| GGT | AGA | ATT | GAG | TTC | TTT | GAT | AAA | CAT | CTG | TCC | ATG | TTC | CCT | CAG | GAT | 985 |
| Gly | Arg | Ile | Glu | Phe | Phe | Asp | Lys | His | Leu | Ser | Met | Phe | Pro | Gln | Asp | |
| | 110 | | | | | 115 | | | | | 120 | | | | | |
| CTG | ACA | TAC | GGG | TTC | TAC | ACC | AGG | GAA | AGA | AAA | GAC | AAC | AAA | ATC | CTT | 1033 |
| Leu | Thr | Tyr | Gly | Phe | Tyr | Thr | Arg | Glu | Arg | Lys | Asp | Asn | Lys | Ile | Leu | |
| 125 | | | | | 130 | | | | | 135 | | | | | 140 | |
| GAT | TAT | ACT | ATA | ATC | GAG | GCA | ACG | GCC | ATT | AAA | GAG | GAC | GGG | TCT | ATC | 1081 |
| Asp | Tyr | Thr | Ile | Ile | Glu | Ala | Thr | Ala | Ile | Lys | Glu | Asp | Gly | Ser | Ile | |
| | | | | 145 | | | | | 150 | | | | | 155 | | |
| GTC | CCA | GGT | CCC | TCT | GTC | GGT | GGT | TCT | CCA | GAA | TTC | ATT | ACA | GTC | AGT | 1129 |
| Val | Pro | Gly | Pro | Ser | Val | Gly | Gly | Ser | Pro | Glu | Phe | Ile | Thr | Val | Ser | |
| | | | 160 | | | | | 165 | | | | | 170 | | | |
| GAT | AAA | GTG | ATT | ATT | GAG | GTT | AAC | ACG | GCT | ACG | CCT | TCG | TTC | GAG | GGT | 1177 |
| Asp | Lys | Val | Ile | Ile | Glu | Val | Asn | Thr | Ala | Thr | Pro | Ser | Phe | Glu | Gly | |
| | | 175 | | | | | 180 | | | | | 185 | | | | |
| ATT | CAC | GAT | ATA | GAC | ATG | CCC | GTG | AAC | CCA | CCT | TTC | AGG | AAA | CCA | TAC | 1225 |
| Ile | His | Asp | Ile | Asp | Met | Pro | Val | Asn | Pro | Pro | Phe | Arg | Lys | Pro | Tyr | |
| | 190 | | | | | 195 | | | | | 200 | | | | | |
| CCA | TAT | CTG | AAA | GTG | GAC | GAC | AAG | TGT | GGT | GTT | GAC | TCC | ATC | CCG | GTT | 1273 |
| Pro | Tyr | Leu | Lys | Val | Asp | Asp | Lys | Cys | Gly | Val | Asp | Ser | Ile | Pro | Val | |
| 205 | | | | | 210 | | | | | 215 | | | | | 220 | |
| GAT | CCT | GAA | AAG | GTT | GTT | GCG | ATT | GTG | GAG | TCC | ACC | ATG | AGG | GAC | CAG | 1321 |
| Asp | Pro | Glu | Lys | Val | Val | Ala | Ile | Val | Glu | Ser | Thr | Met | Arg | Asp | Gln | |
| | | | | 225 | | | | | 230 | | | | | 235 | | |

| | | | | | | | | | | | | | | | | |
|---|---|---|---|---|---|---|---|---|---|---|---|---|---|---|---|---|
| GTC | CCA | CCA | AAT | ACG | CCC | TCT | GAC | GAC | ATG | TCC | AGG | GCT | ATT | GCA | GGT | 1369 |
| Val | Pro | Pro | Asn<br>240 | Thr | Pro | Ser | Asp | Asp<br>245 | Met | Ser | Arg | Ala | Ile<br>250 | Ala | Gly | |
| CAT | TTG | GTC | GAG | TTT | TTC | AGA | AAC | GAG | GTA | AAA | CAT | GGT | AGG | CTA | CCT | 1417 |
| His | Leu | Val<br>255 | Glu | Phe | Phe | Arg | Asn | Glu<br>260 | Val | Lys | His | Gly | Arg<br>265 | Leu | Pro | |
| GAA | AAC | CTG | CTG | CCT | TTA | CAA | AGT | GGT | ATA | GGT | AAC | ATT | GCT | AAC | GCT | 1465 |
| Glu | Asn<br>270 | Leu | Leu | Pro | Leu | Gln<br>275 | Ser | Gly | Ile | Gly | Asn<br>280 | Ile | Ala | Asn | Ala | |
| GTC | ATT | GAA | GGG | CTT | GCT | GGC | GCC | CAA | TTC | AAG | CAC | TTG | ACT | GTA | TGG | 1513 |
| Val<br>285 | Ile | Glu | Gly | Leu<br>290 | Ala | Gly | Ala | Gln | Phe<br>295 | Lys | His | Leu | Thr | Val<br>300 | Trp | |
| ACG | GAA | GTG | CTG | CAG | GAC | TCG | TTA | TTG | GAT | CTT | TTC | GAG | AAC | GGA | TCT | 1561 |
| Thr | Glu | Val | Leu | Gln<br>305 | Asp | Ser | Leu | Leu | Asp<br>310 | Leu | Phe | Glu | Asn | Gly<br>315 | Ser | |
| TTG | GAC | TAC | TCC | ACT | GCT | ACT | TCC | GTG | AGA | TTG | ACT | GAA | AAG | GGT | TTC | 1609 |
| Leu | Asp | Tyr | Ser<br>320 | Thr | Ala | Thr | Ser | Val<br>325 | Arg | Leu | Thr | Glu | Lys<br>330 | Gly | Phe | |
| GAC | AGA | GCC | TTT | GCA | AAC | TGG | GAA | AAT | TTC | AAA | CAC | AGA | TTG | TGT | TTG | 1657 |
| Asp | Arg | Ala<br>335 | Phe | Ala | Asn | Trp | Glu<br>340 | Asn | Phe | Lys | His | Arg<br>345 | Leu | Cys | Leu | |
| AGA | TCT | CAA | GTT | GTC | TCG | AAC | AAT | CCG | GAA | ATG | ATC | CGT | AGA | TTC | CCT | 1705 |
| Arg | Ser | Gln<br>350 | Val | Val | Ser | Asn<br>355 | Asn | Pro | Glu | Met | Ile<br>360 | Arg | Arg | Phe | Pro | |
| GTC | ATC | GCC | ATG | AAT | ACC | CCA | GTA | GAA | GTT | GAC | ATT | TAC | GCG | CAC | GCC | 1753 |
| Val<br>365 | Ile | Ala | Met | Asn | Thr<br>370 | Pro | Val | Glu | Val | Asp<br>375 | Ile | Tyr | Ala | His | Ala<br>380 | |
| AAT | TCT | ACA | AAT | GTG | AAT | GGT | TCC | CGT | ATG | TTG | AAC | GGG | TTG | GGT | GGA | 1801 |
| Asn | Ser | Thr | Asn | Val<br>385 | Asn | Gly | Ser | Arg | Met<br>390 | Leu | Asn | Gly | Leu | Gly<br>395 | Gly | |
| TCT | GCT | GAT | TTC | TTG | AGA | AAT | GCA | AAG | TTG | TCC | ATC | ATG | CAT | GCC | CCC | 1849 |
| Ser | Ala | Asp | Phe<br>400 | Leu | Arg | Asn | Ala | Lys<br>405 | Leu | Ser | Ile | Met | His<br>410 | Ala | Pro | |
| TCT | GCA | AGA | CCA | ACT | AAA | GTA | GAC | CCT | ACC | GGT | ATC | TCT | ACC | ATT | GTT | 1897 |
| Ser | Ala | Arg<br>415 | Pro | Thr | Lys | Val | Asp<br>420 | Pro | Thr | Gly | Ile | Ser<br>425 | Thr | Ile | Val | |
| CCT | ATG | GCC | TCT | CAT | GTA | GAT | CAA | ACT | GAG | CAT | GAC | CTG | GAC | ATC | TTG | 1945 |
| Pro | Met<br>430 | Ala | Ser | His | Val | Asp<br>435 | Gln | Thr | Glu | His | Asp<br>440 | Leu | Asp | Ile | Leu | |
| GTC | ACT | GAC | CAA | GGT | TTG | GCG | GAT | CTA | AGA | GGT | CTA | TCG | CCT | AAG | GAA | 1993 |
| Val | Thr | Asp | Gln<br>445 | Gly | Leu | Ala | Asp<br>450 | Leu | Arg | Gly | Leu<br>455 | Ser | Pro | Lys | Glu<br>460 | |
| AGA | GCC | CGT | GAA | ATC | ATC | AAC | AAG | TGT | GCT | CAT | CCC | GAT | TAT | CAA | GCT | 2041 |
| Arg | Ala | Arg | Glu | Ile<br>465 | Ile | Asn | Lys | Cys | Ala<br>470 | His | Pro | Asp | Tyr | Gln<br>475 | Ala | |
| TTG | TTG | ACC | GAT | TAC | TTG | GAC | AGA | GCA | GAG | CAT | TAC | GCT | AAA | AAG | CAC | 2089 |
| Leu | Leu | Thr | Asp<br>480 | Tyr | Leu | Asp | Arg | Ala<br>485 | Glu | His | Tyr | Ala | Lys<br>490 | Lys | His | |
| AAT | TGC | TTG | CAT | GAA | CCA | CAC | ATG | CTA | AAG | AAT | GCT | TTC | AAG | TTC | CAC | 2137 |
| Asn | Cys | Leu | His<br>495 | Glu | Pro | His | Met | Leu<br>500 | Lys | Asn | Ala | Phe | Lys<br>505 | Phe | His | |
| ACC | AAC | TTA | GCT | GAA | AAG | GGT | ACA | ATG | AAG | GTC | GAC | AGC | TGG | GAA | CCA | 2185 |
| Thr | Asn | Leu<br>510 | Ala | Glu | Lys | Gly | Thr<br>515 | Met | Lys | Val | Asp | Ser<br>520 | Trp | Glu | Pro | |
| GTT | GAC | TAGTGTTTGT | GCGCAAACCG | AGAGATGAGT | ATTTAACAAA | AAAAGAAAG | | | | | | | | | | 2241 |
| Val | Asp<br>525 | | | | | | | | | | | | | | | |

```
GAAATGATAT GATTATGATT TTATGTTTAT AAAGCTTTTA TCCAATGCGT TGTTTTTTCT    2301

TGCATATTTA TACCTTTTGC GCTCATGGAG GGAGTTAATC AATACGCATG ACGTCTAGTT    2361
```

```
AATTCACAGG TAGTACTGTA TATTTATATG TTTACACAAT AATTATGTAT TAAGTAGTGA      2421

TTAGTAAAAA AAACTAAGAG GTTGAAAGTC ATCAACCCTT ATATT                      2466
```

( 2 ) INFORMATION FOR SEQ ID NO:6:

( i ) SEQUENCE CHARACTERISTICS:
        ( A ) LENGTH: 526 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Thr Ile Ser Asn Leu Leu Lys Gln Arg Val Arg Tyr Ala Pro Tyr
 1           5                  10                 15

Leu Lys Lys Val Lys Glu Ala His Glu Leu Ile Pro Leu Phe Lys Asn
            20                 25                 30

Gly Gln Tyr Leu Gly Trp Ser Gly Phe Thr Gly Val Gly Thr Pro Lys
             35                 40                 45

Ala Val Pro Glu Ala Leu Ile Asp His Val Glu Lys Asn Asn Leu Gln
         50                 55                 60

Gly Lys Leu Arg Phe Asn Leu Phe Val Gly Ala Ser Ala Gly Pro Glu
 65              70                 75                     80

Glu Asn Arg Trp Ala Glu His Asp Met Ile Ile Lys Arg Ala Pro His
                 85                 90                     95

Gln Val Gly Lys Pro Ile Ala Lys Ala Ile Asn Gln Gly Arg Ile Glu
            100                105                110

Phe Phe Asp Lys His Leu Ser Met Phe Pro Gln Asp Leu Thr Tyr Gly
            115                120                125

Phe Tyr Thr Arg Glu Arg Lys Asp Asn Lys Ile Leu Asp Tyr Thr Ile
    130                135                140

Ile Glu Ala Thr Ala Ile Lys Glu Asp Gly Ser Ile Val Pro Gly Pro
145                150                155                    160

Ser Val Gly Gly Ser Pro Glu Phe Ile Thr Val Ser Asp Lys Val Ile
                165                170                175

Ile Glu Val Asn Thr Ala Thr Pro Ser Phe Glu Gly Ile His Asp Ile
                180                185                190

Asp Met Pro Val Asn Pro Pro Phe Arg Lys Pro Tyr Pro Tyr Leu Lys
        195                200                205

Val Asp Asp Lys Cys Gly Val Asp Ser Ile Pro Val Asp Pro Glu Lys
210                215                220

Val Val Ala Ile Val Glu Ser Thr Met Arg Asp Gln Val Pro Pro Asn
225                230                235                    240

Thr Pro Ser Asp Asp Met Ser Arg Ala Ile Ala Gly His Leu Val Glu
                245                250                255

Phe Phe Arg Asn Glu Val Lys His Gly Arg Leu Pro Glu Asn Leu Leu
            260                265                270

Pro Leu Gln Ser Gly Ile Gly Asn Ile Ala Asn Ala Val Ile Glu Gly
            275                280                285

Leu Ala Gly Ala Gln Phe Lys His Leu Thr Val Trp Thr Glu Val Leu
    290                295                300

Gln Asp Ser Leu Leu Asp Leu Phe Glu Asn Gly Ser Leu Asp Tyr Ser
305                310                315                    320

Thr Ala Thr Ser Val Arg Leu Thr Glu Lys Gly Phe Asp Arg Ala Phe
                325                330                335
```

| Ala | Asn | Trp | Glu | Asn | Phe | Lys | His | Arg | Leu | Cys | Leu | Arg | Ser | Gln | Val |
| | | | 340 | | | | 345 | | | | | | 350 | | |

| Val | Ser | Asn | Asn | Pro | Glu | Met | Ile | Arg | Arg | Phe | Pro | Val | Ile | Ala | Met |
| | | | 355 | | | | 360 | | | | | 365 | | | |

| Asn | Thr | Pro | Val | Glu | Val | Asp | Ile | Tyr | Ala | His | Ala | Asn | Ser | Thr | Asn |
| | 370 | | | | | 375 | | | | | 380 | | | | |

| Val | Asn | Gly | Ser | Arg | Met | Leu | Asn | Gly | Leu | Gly | Gly | Ser | Ala | Asp | Phe |
| 385 | | | | | 390 | | | | | 395 | | | | | 400 |

| Leu | Arg | Asn | Ala | Lys | Leu | Ser | Ile | Met | His | Ala | Pro | Ser | Ala | Arg | Pro |
| | | | | 405 | | | | | 410 | | | | | 415 | |

| Thr | Lys | Val | Asp | Pro | Thr | Gly | Ile | Ser | Thr | Ile | Val | Pro | Met | Ala | Ser |
| | | | 420 | | | | | 425 | | | | | 430 | | |

| His | Val | Asp | Gln | Thr | Glu | His | Asp | Leu | Asp | Ile | Leu | Val | Thr | Asp | Gln |
| | | | 435 | | | | | 440 | | | | | 445 | | |

| Gly | Leu | Ala | Asp | Leu | Arg | Gly | Leu | Ser | Pro | Lys | Glu | Arg | Ala | Arg | Glu |
| | 450 | | | | | 455 | | | | | 460 | | | | |

| Ile | Ile | Asn | Lys | Cys | Ala | His | Pro | Asp | Tyr | Gln | Ala | Leu | Leu | Thr | Asp |
| 465 | | | | | 470 | | | | | 475 | | | | | 480 |

| Tyr | Leu | Asp | Arg | Ala | Glu | His | Tyr | Ala | Lys | Lys | His | Asn | Cys | Leu | His |
| | | | | 485 | | | | | 490 | | | | | 495 | |

| Glu | Pro | His | Met | Leu | Lys | Asn | Ala | Phe | Lys | Phe | His | Thr | Asn | Leu | Ala |
| | | | 500 | | | | | 505 | | | | | 510 | | |

| Glu | Lys | Gly | Thr | Met | Lys | Val | Asp | Ser | Trp | Glu | Pro | Val | Asp |
| | | | 515 | | | | | 520 | | | | | 525 |

( 2 ) INFORMATION FOR SEQ ID NO:7:

( i ) SEQUENCE CHARACTERISTICS:
        ( A ) LENGTH: 3089 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1237..2814

( x i ) SEQUENCE DESCRIPTION: SEQ ID NO:7:

```
ATAACTCCAA CTGTGACTTG AAATATGTGA TTCGGTTAGC AAGAATCATT GACGAGTCAG      60
CCGCGGACAA TTCAGAGCCC ACAGGTCAGC AAAGCGGCAT GACCGAGTAT GTGGCCACAC     120
GTTGGTACAG GGCGCCAGAG GTGATGTTAA CCTCTGCCAA ATACTCAAGG GCCATGGACG     180
TGTGGCTGCG GATGTATTCT CGCTGAACTT TTCTTAAGAC GGCCAATCTT CCCTGGCAGA     240
GATTATCGCC ATCAACTACT ACTGATATTC GGTATCATCG GTACACCTCA CTCAGATAAT     300
GATTTGCGGT GTATAGAGTC ACCCAGGGCT AGAGAGTACA TAAAGTCGCT TCCCATGTAC     360
CCTGCCGCGC CACTGGAGAA GATGTTCCTC GAGTCAACCC GAAAGGCCAA TAGATCTTTT     420
ACAGCGTATG CTTGTTTTTG ACCCTGCGAA GAGGATTACT GCTAAGGAGG CACTGGAGCA     480
TCCGTATTTG CAGACATACC ACGATCCAAA TGACGAACCT GAAGGCGAAC CCATCCCACC     540
CAGCTTCTTC GAGTTTGATC ACCACAAGGA GGCACTAACG ACGAAAGACC TCAAGAAACT     600
CATTTGGAAC GAAATATTTA GTTAGCCATC ATTATCATTA AAATATCAAC CGAAGAACA     660
ATAATGTATA CATATACATA TACGTACACA TATACATATG TACATATGAC ATACGTATTA     720
GCCGCTGAGG ACGCGGACGT ATAAAAGGAC AATACTTATA TGGAGCTAAG GGGAGCAGTC     780
ACGCAACTCC GTGATCGCGC GCCACGGGCC GTCGGCGGCT GTTAATTGAA GAAAAAAAA     840
ATGAAGAACC ACAAGGGGTG ATCCATATAG GTGACTAGCA TCATCCCCTG CGACGCGCGG     900
```

```
CCCGCCGGGC AAAGGCGGGC AATGCGCGCT GCTGATTGGC CTCGAGGACA ACGCCCTCAA        960
CCACATCCGC AACAGCCAAT CCCATCGGAG CGTCAAACTA CCAAAGTAGT GATTGTATGG       1020
ATCACCACTG TATTGTGGAC GGTAAGCGCT TGCTGGAGCA AATGTGTAAT CAAGTTGCTG       1080
TGTATATATA GACGTTAGAT GTGTTCTACC CCTTCTTTTG TCTTGTGCCC ACCGGGCTTA       1140
CATTAGCACA CAAAGCAGCA AGAGACCGTC TTACTAGACA ATAGCGGCAA AACAAACAAC       1200
ACATTTCTTT TTTTCTTTTT CACATATTGC ACTAAA ATG ACA ATT TCT AAT TTG         1254
                                        Met Thr Ile Ser Asn Leu
                                         1               5
```

| TTA | AAG | CAG | AGA | GTT | AGG | TAT | GCT | CCC | TAT | CTG | AAA | AAA | GTT | AAG | GAA | 1302 |
|-----|-----|-----|-----|-----|-----|-----|-----|-----|-----|-----|-----|-----|-----|-----|-----|------|
| Leu | Lys | Gln | Arg | Val | Arg | Tyr | Ala | Pro | Tyr | Leu | Lys | Lys | Val | Lys | Glu |      |
|     |     |     | 10  |     |     |     |     | 15  |     |     |     |     |     | 20  |     |      |

| GCT | CAC | GAG | CTT | ATT | CCA | TTG | TTC | AAG | AAT | GGT | CAG | TAC | CTT | GGG | TGG | 1350 |
|-----|-----|-----|-----|-----|-----|-----|-----|-----|-----|-----|-----|-----|-----|-----|-----|------|
| Ala | His | Glu | Leu | Ile | Pro | Leu | Phe | Lys | Asn | Gly | Gln | Tyr | Leu | Gly | Trp |      |
|     |     | 25  |     |     |     |     | 30  |     |     |     |     | 35  |     |     |     |      |

| TCC | GGT | TTT | ACA | GGA | GTG | GGT | ACT | CCC | AAG | GCA | GTG | CCG | GAG | GCA | CTG | 1398 |
|-----|-----|-----|-----|-----|-----|-----|-----|-----|-----|-----|-----|-----|-----|-----|-----|------|
| Ser | Gly | Phe | Thr | Gly | Val | Gly | Thr | Pro | Lys | Ala | Val | Pro | Glu | Ala | Leu |      |
|     |     | 40  |     |     |     | 45  |     |     |     |     | 50  |     |     |     |     |      |

| ATA | GAT | CAC | GTG | GAG | AAG | AAC | AAT | TTA | CAA | GGG | AAG | TTG | AGA | TTC | AAC | 1446 |
|-----|-----|-----|-----|-----|-----|-----|-----|-----|-----|-----|-----|-----|-----|-----|-----|------|
| Ile | Asp | His | Val | Glu | Lys | Asn | Asn | Leu | Gln | Gly | Lys | Leu | Arg | Phe | Asn |      |
| 55  |     |     |     |     | 60  |     |     |     |     | 65  |     |     |     |     | 70  |      |

| CTT | TTT | GTT | GGA | GCT | TCT | GCT | GGT | CCA | GAG | GAA | AAC | CGT | TGG | GCT | GAA | 1494 |
|-----|-----|-----|-----|-----|-----|-----|-----|-----|-----|-----|-----|-----|-----|-----|-----|------|
| Leu | Phe | Val | Gly | Ala | Ser | Ala | Gly | Pro | Glu | Glu | Asn | Arg | Trp | Ala | Glu |      |
|     |     |     |     | 75  |     |     |     |     | 80  |     |     |     |     | 85  |     |      |

| CAC | GAC | ATG | ATC | ATT | AAG | AGA | GCC | CCT | CAT | CAA | GTA | GGG | AAA | CCC | ATT | 1542 |
|-----|-----|-----|-----|-----|-----|-----|-----|-----|-----|-----|-----|-----|-----|-----|-----|------|
| His | Asp | Met | Ile | Ile | Lys | Arg | Ala | Pro | His | Gln | Val | Gly | Lys | Pro | Ile |      |
|     |     |     |     | 90  |     |     |     |     | 95  |     |     |     |     | 100 |     |      |

| GCA | AAG | GCA | ATT | AAC | CAG | GGT | AGA | ATT | GAG | TTC | TTT | GAT | AAA | CAT | CTG | 1590 |
|-----|-----|-----|-----|-----|-----|-----|-----|-----|-----|-----|-----|-----|-----|-----|-----|------|
| Ala | Lys | Ala | Ile | Asn | Gln | Gly | Arg | Ile | Glu | Phe | Phe | Asp | Lys | His | Leu |      |
|     |     | 105 |     |     |     |     | 110 |     |     |     |     |     | 115 |     |     |      |

| TCC | ATG | TTC | CCT | CAG | GAT | CTG | ACA | TAC | GGG | TTC | TAC | ACC | AGG | GAA | AGA | 1638 |
|-----|-----|-----|-----|-----|-----|-----|-----|-----|-----|-----|-----|-----|-----|-----|-----|------|
| Ser | Met | Phe | Pro | Gln | Asp | Leu | Thr | Tyr | Gly | Phe | Tyr | Thr | Arg | Glu | Arg |      |
|     | 120 |     |     |     |     | 125 |     |     |     |     | 130 |     |     |     |     |      |

| AAA | GAC | AAC | AAA | ATC | CTT | GAT | TAT | ACT | ATA | ATC | GAG | GCA | ACG | GCC | ATT | 1686 |
|-----|-----|-----|-----|-----|-----|-----|-----|-----|-----|-----|-----|-----|-----|-----|-----|------|
| Lys | Asp | Asn | Lys | Ile | Leu | Asp | Tyr | Thr | Ile | Ile | Glu | Ala | Thr | Ala | Ile |      |
| 135 |     |     |     |     | 140 |     |     |     |     | 145 |     |     |     |     | 150 |      |

| AAA | GAG | GAC | GGG | TCT | ATC | GTC | CCA | GGT | CCC | TCT | GTC | GGT | GGT | TCT | CCA | 1734 |
|-----|-----|-----|-----|-----|-----|-----|-----|-----|-----|-----|-----|-----|-----|-----|-----|------|
| Lys | Glu | Asp | Gly | Ser | Ile | Val | Pro | Gly | Pro | Ser | Val | Gly | Gly | Ser | Pro |      |
|     |     |     |     | 155 |     |     |     |     | 160 |     |     |     |     | 165 |     |      |

| GAA | TTC | ATT | ACA | GTC | AGT | GAT | AAA | GTG | ATT | ATT | GAG | GTT | AAC | ACG | GCT | 1782 |
|-----|-----|-----|-----|-----|-----|-----|-----|-----|-----|-----|-----|-----|-----|-----|-----|------|
| Glu | Phe | Ile | Thr | Val | Ser | Asp | Lys | Val | Ile | Ile | Glu | Val | Asn | Thr | Ala |      |
|     |     |     | 170 |     |     |     |     | 175 |     |     |     |     | 180 |     |     |      |

| ACG | CCT | TCG | TTC | GAG | GGT | ATT | CAC | GAT | ATA | GAC | ATG | CCC | GTG | AAC | CCA | 1830 |
|-----|-----|-----|-----|-----|-----|-----|-----|-----|-----|-----|-----|-----|-----|-----|-----|------|
| Thr | Pro | Ser | Phe | Glu | Gly | Ile | His | Asp | Ile | Asp | Met | Pro | Val | Asn | Pro |      |
|     |     | 185 |     |     |     |     | 190 |     |     |     |     | 195 |     |     |     |      |

| CCT | TTC | AGG | AAA | CCA | TAC | CCA | TAT | CTG | AAA | GTG | GAC | GAC | AAG | TGT | GGT | 1878 |
|-----|-----|-----|-----|-----|-----|-----|-----|-----|-----|-----|-----|-----|-----|-----|-----|------|
| Pro | Phe | Arg | Lys | Pro | Tyr | Pro | Tyr | Leu | Lys | Val | Asp | Asp | Lys | Cys | Gly |      |
|     | 200 |     |     |     |     | 205 |     |     |     |     | 210 |     |     |     |     |      |

| GTT | GAC | TCC | ATC | CCG | GTT | GAT | CCT | GAA | AAG | GTT | GTT | GCG | ATT | GTG | GAG | 1926 |
|-----|-----|-----|-----|-----|-----|-----|-----|-----|-----|-----|-----|-----|-----|-----|-----|------|
| Val | Asp | Ser | Ile | Pro | Val | Asp | Pro | Glu | Lys | Val | Val | Ala | Ile | Val | Glu |      |
| 215 |     |     |     |     | 220 |     |     |     |     | 225 |     |     |     |     | 230 |      |

| TCC | ACC | ATG | AGG | GAC | CAG | GTC | CCA | CCA | AAT | ACG | CCC | TCT | GAC | GAC | ATG | 1974 |
|-----|-----|-----|-----|-----|-----|-----|-----|-----|-----|-----|-----|-----|-----|-----|-----|------|
| Ser | Thr | Met | Arg | Asp | Gln | Val | Pro | Pro | Asn | Thr | Pro | Ser | Asp | Asp | Met |      |
|     |     |     |     | 235 |     |     |     |     | 240 |     |     |     |     | 245 |     |      |

| TCC | AGG | GCT | ATT | GCA | GGT | CAT | TTG | GTC | GAG | TTT | TTC | AGA | AAC | GAG | GTA | 2022 |
|-----|-----|-----|-----|-----|-----|-----|-----|-----|-----|-----|-----|-----|-----|-----|-----|------|
| Ser | Arg | Ala | Ile | Ala | Gly | His | Leu | Val | Glu | Phe | Phe | Arg | Asn | Glu | Val |      |
|     |     |     |     | 250 |     |     |     |     | 255 |     |     |     |     | 260 |     |      |

| AAA | CAT | GGT | AGG | CTA | CCT | GAA | AAC | CTG | CTG | CCT | TTA | CAA | AGT | GGT | ATA | 2070 |
|-----|-----|-----|-----|-----|-----|-----|-----|-----|-----|-----|-----|-----|-----|-----|-----|------|

|     |     |     |     |     |     |     |     |     |     |     |     |     |     |     |     |
|---|---|---|---|---|---|---|---|---|---|---|---|---|---|---|---|
| Lys | His | Gly | Arg | Leu | Pro | Glu | Asn | Leu | Leu | Pro | Leu | Gln | Ser | Gly | Ile |
|     |     | 265 |     |     |     | 270 |     |     |     |     | 275 |     |     |     |     |

```
GGT AAC ATT GCT AAC GCT GTC ATT GAA GGG CTT GCT GGC GCC CAA TTC      2118
Gly Asn Ile Ala Asn Ala Val Ile Glu Gly Leu Ala Gly Ala Gln Phe
    280             285                 290

AAG CAC TTG ACT GTA TGG ACG GAA GTG CTG CAG GAC TCG TTA TTG GAT      2166
Lys His Leu Thr Val Trp Thr Glu Val Leu Gln Asp Ser Leu Leu Asp
295                 300                 305                 310

CTT TTC GAG AAC GGA TCT TTG GAC TAC TCC ACT GCT ACT TCC GTG AGA      2214
Leu Phe Glu Asn Gly Ser Leu Asp Tyr Ser Thr Ala Thr Ser Val Arg
                315                 320                 325

TTG ACT GAA AAG GGT TTC GAC AGA GCC TTT GCA AAC TGG GAA AAT TTC      2262
Leu Thr Glu Lys Gly Phe Asp Arg Ala Phe Ala Asn Trp Glu Asn Phe
            330                 335                 340

AAA CAC AGA TTG TGT TTG AGA TCT CAA GTT GTC TCG AAC AAT CCG GAA      2310
Lys His Arg Leu Cys Leu Arg Ser Gln Val Val Ser Asn Asn Pro Glu
        345                 350                 355

ATG ATC CGT AGA TTC CCT GTC ATC GCC ATG AAT ACC CCA GTA GAA GTT      2358
Met Ile Arg Arg Phe Pro Val Ile Ala Met Asn Thr Pro Val Glu Val
    360                 365                 370

GAC ATT TAC GCG CAC GCC AAT TCT ACA AAT GTG AAT GGT TCC CGT ATG      2406
Asp Ile Tyr Ala His Ala Asn Ser Thr Asn Val Asn Gly Ser Arg Met
375                 380                 385                 390

TTG AAC GGG TTG GGT GGA TCT GCT GAT TTC TTG AGA AAT GCA AAG TTG      2454
Leu Asn Gly Leu Gly Gly Ser Ala Asp Phe Leu Arg Asn Ala Lys Leu
                395                 400                 405

TCC ATC ATG CAT GCC CCC TCT GCA AGA CCA ACT AAA GTA GAC CCT ACC      2502
Ser Ile Met His Ala Pro Ser Ala Arg Pro Thr Lys Val Asp Pro Thr
            410                 415                 420

GGT ATC TCT ACC ATT GTT CCT ATG GCC TCT CAT GTA GAT CAA ACT GAG      2550
Gly Ile Ser Thr Ile Val Pro Met Ala Ser His Val Asp Gln Thr Glu
        425                 430                 435

CAT GAC CTG GAC ATC TTG GTC ACT GAC CAA GGT TTG GCG GAT CTA AGA      2598
His Asp Leu Asp Ile Leu Val Thr Asp Gln Gly Leu Ala Asp Leu Arg
    440                 445                 450

GGT CTA TCG CCT AAG GAA AGA GCC CGT GAA ATC ATC AAC AAG TGT GCT      2646
Gly Leu Ser Pro Lys Glu Arg Ala Arg Glu Ile Ile Asn Lys Cys Ala
455                 460                 465                 470

CAT CCC GAT TAT CAA GCT TTG TTG ACC GAT TAC TTG GAC AGA GCA GAG      2694
His Pro Asp Tyr Gln Ala Leu Leu Thr Asp Tyr Leu Asp Arg Ala Glu
                475                 480                 485

CAT TAC GCT AAA AAG CAC AAT TGC TTG CAT GAA CCA CAC ATG CTA AAG      2742
His Tyr Ala Lys Lys His Asn Cys Leu His Glu Pro His Met Leu Lys
            490                 495                 500

AAT GCT TTC AAG TTC CAC ACC AAC TTA GCT GAA AAG GGT ACA ATG AAG      2790
Asn Ala Phe Lys Phe His Thr Asn Leu Ala Glu Lys Gly Thr Met Lys
        505                 510                 515

GTC GAC AGC TGG GAA CCA GTT GAC TAGTGTTTGT GCGCAAACCG AGAGATGAGT     2844
Val Asp Ser Trp Glu Pro Val Asp
    520                 525

ATTTAACAAA AAAAAGAAAG GAAATGATAT GATTATGATT TTATGTTTAT AAAGCTTTTA   2904

TCCAATGCGT TGTTTTTTCT TGCATATTTA TACCTTTTGC GCTCATGGAG GGAGTTAATC   2964

AATACGCATG ACGTCTAGTT AATTCACAGG TAGTACTGTA TATTTATATG TTTACACAAT   3024

AATTATGTAT TAAGTAGTGA TTAGTAAAAA AAACTAAGAG GTTGAAAGTC ATCAACCCTT   3084

ATATT                                                              3089
```

( 2 ) INFORMATION FOR SEQ ID NO:8:

5,487,990

47

48

-continued ( i ) SEQUENCE CHARACTERISTICS:
  ( A ) LENGTH: 526 amino acids
  ( B ) TYPE: amino acid
  ( D ) TOPOLOGY: linear ( i i ) MOLECULE TYPE: protein ( x i ) SEQUENCE DESCRIPTION: SEQ ID NO:8:

| Met | Thr | Ile | Ser | Asn | Leu | Leu | Lys | Gln | Arg | Val | Arg | Tyr | Ala | Pro | Tyr |
|---|---|---|---|---|---|---|---|---|---|---|---|---|---|---|---|
| 1 | | | | 5 | | | | | 10 | | | | | 15 | |
| Leu | Lys | Lys | Val | Lys | Glu | Ala | His | Glu | Leu | Ile | Pro | Leu | Phe | Lys | Asn |
| | | | 20 | | | | | 25 | | | | | 30 | | |
| Gly | Gln | Tyr | Leu | Gly | Trp | Ser | Gly | Phe | Thr | Gly | Val | Gly | Thr | Pro | Lys |
| | | 35 | | | | | 40 | | | | | 45 | | | |
| Ala | Val | Pro | Glu | Ala | Leu | Ile | Asp | His | Val | Glu | Lys | Asn | Asn | Leu | Gln |
| | 50 | | | | | 55 | | | | | 60 | | | | |
| Gly | Lys | Leu | Arg | Phe | Asn | Leu | Phe | Val | Gly | Ala | Ser | Ala | Gly | Pro | Glu |
| 65 | | | | | 70 | | | | | 75 | | | | | 80 |
| Glu | Asn | Arg | Trp | Ala | Glu | His | Asp | Met | Ile | Ile | Lys | Arg | Ala | Pro | His |
| | | | | 85 | | | | | 90 | | | | | 95 | |
| Gln | Val | Gly | Lys | Pro | Ile | Ala | Lys | Ala | Ile | Asn | Gln | Gly | Arg | Ile | Glu |
| | | | | 100 | | | | | 105 | | | | | 110 | |
| Phe | Phe | Asp | Lys | His | Leu | Ser | Met | Phe | Pro | Gln | Asp | Leu | Thr | Tyr | Gly |
| | | | 115 | | | | | 120 | | | | | 125 | | |
| Phe | Tyr | Thr | Arg | Glu | Arg | Lys | Asp | Asn | Lys | Ile | Leu | Asp | Tyr | Thr | Ile |
| | | 130 | | | | | 135 | | | | | 140 | | | |
| Ile | Glu | Ala | Thr | Ala | Ile | Lys | Glu | Asp | Gly | Ser | Ile | Val | Pro | Gly | Pro |
| 145 | | | | | 150 | | | | | 155 | | | | | 160 |
| Ser | Val | Gly | Gly | Ser | Pro | Glu | Phe | Ile | Thr | Val | Ser | Asp | Lys | Val | Ile |
| | | | | 165 | | | | | 170 | | | | | 175 | |
| Ile | Glu | Val | Asn | Thr | Ala | Thr | Pro | Ser | Phe | Glu | Gly | Ile | His | Asp | Ile |
| | | | 180 | | | | | 185 | | | | | 190 | | |
| Asp | Met | Pro | Val | Asn | Pro | Pro | Phe | Arg | Lys | Pro | Tyr | Pro | Tyr | Leu | Lys |
| | | 195 | | | | | 200 | | | | | 205 | | | |
| Val | Asp | Asp | Lys | Cys | Gly | Val | Asp | Ser | Ile | Pro | Val | Asp | Pro | Glu | Lys |
| | 210 | | | | | 215 | | | | | 220 | | | | |
| Val | Val | Ala | Ile | Val | Glu | Ser | Thr | Met | Arg | Asp | Gln | Val | Pro | Pro | Asn |
| 225 | | | | | 230 | | | | | 235 | | | | | 240 |
| Thr | Pro | Ser | Asp | Asp | Met | Ser | Arg | Ala | Ile | Ala | Gly | His | Leu | Val | Glu |
| | | | | 245 | | | | | 250 | | | | | 255 | |
| Phe | Phe | Arg | Asn | Glu | Val | Lys | His | Gly | Arg | Leu | Pro | Glu | Asn | Leu | Leu |
| | | | 260 | | | | | 265 | | | | | 270 | | |
| Pro | Leu | Gln | Ser | Gly | Ile | Gly | Asn | Ile | Ala | Asn | Ala | Val | Ile | Glu | Gly |
| | | 275 | | | | | 280 | | | | | 285 | | | |
| Leu | Ala | Gly | Ala | Gln | Phe | Lys | His | Leu | Thr | Val | Trp | Thr | Glu | Val | Leu |
| | 290 | | | | | 295 | | | | | 300 | | | | |
| Gln | Asp | Ser | Leu | Leu | Asp | Leu | Phe | Glu | Asn | Gly | Ser | Leu | Asp | Tyr | Ser |
| 305 | | | | | 310 | | | | | 315 | | | | | 320 |
| Thr | Ala | Thr | Ser | Val | Arg | Leu | Thr | Glu | Lys | Gly | Phe | Asp | Arg | Ala | Phe |
| | | | | 325 | | | | | 330 | | | | | 335 | |
| Ala | Asn | Trp | Glu | Asn | Phe | Lys | His | Arg | Leu | Cys | Leu | Arg | Ser | Gln | Val |
| | | | 340 | | | | | 345 | | | | | 350 | | |
| Val | Ser | Asn | Asn | Pro | Glu | Met | Ile | Arg | Arg | Phe | Pro | Val | Ile | Ala | Met |
| | | 355 | | | | | 360 | | | | | 365 | | | |
| Asn | Thr | Pro | Val | Glu | Val | Asp | Ile | Tyr | Ala | His | Ala | Asn | Ser | Thr | Asn |
| | 370 | | | | | 375 | | | | | 380 | | | | |

| Val | Asn | Gly | Ser | Arg | Met | Leu | Asn | Gly | Leu | Gly | Gly | Ser | Ala | Asp | Phe |
| 385 | | | | | 390 | | | | | 395 | | | | | 400 |

| Leu | Arg | Asn | Ala | Lys | Leu | Ser | Ile | Met | His | Ala | Pro | Ser | Ala | Arg | Pro |
| | | | | 405 | | | | | 410 | | | | | 415 | |

| Thr | Lys | Val | Asp | Pro | Thr | Gly | Ile | Ser | Thr | Ile | Val | Pro | Met | Ala | Ser |
| | | | 420 | | | | | 425 | | | | | 430 | | |

| His | Val | Asp | Gln | Thr | Glu | His | Asp | Leu | Asp | Ile | Leu | Val | Thr | Asp | Gln |
| | | | 435 | | | | 440 | | | | | 445 | | | |

| Gly | Leu | Ala | Asp | Leu | Arg | Gly | Leu | Ser | Pro | Lys | Glu | Arg | Ala | Arg | Glu |
| | 450 | | | | | 455 | | | | | 460 | | | | |

| Ile | Ile | Asn | Lys | Cys | Ala | His | Pro | Asp | Tyr | Gln | Ala | Leu | Leu | Thr | Asp |
| 465 | | | | | 470 | | | | | 475 | | | | | 480 |

| Tyr | Leu | Asp | Arg | Ala | Glu | His | Tyr | Ala | Lys | Lys | His | Asn | Cys | Leu | His |
| | | | | 485 | | | | | 490 | | | | | 495 | |

| Glu | Pro | His | Met | Leu | Lys | Asn | Ala | Phe | Lys | Phe | His | Thr | Asn | Leu | Ala |
| | | | 500 | | | | | 505 | | | | | 510 | | |

| Glu | Lys | Gly | Thr | Met | Lys | Val | Asp | Ser | Trp | Glu | Pro | Val | Asp |
| | | | 515 | | | | 520 | | | | | 525 | |

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

ATCATYTCNG GRTTRTT           17

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GGNGCRTGCA TNAT           14

( 2 ) INFORMATION FOR SEQ ID NO:11:

( i ) SEQUENCE CHARACTERISTICS:
        ( A ) LENGTH: 173 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

AGGGGAGCAG TCACGCAACT CCGTGATCGC GCGCCACGGG CCGTCGGCGG CTGTTAATTG    60

AAGAAAAAAA AAATGAAGAA CCACAAGGGG TGATCCATAT AGGTGACTAG CATCATCCCC   120

TGCGACGCGC GGCCCGCCGG GCAAAGGCGG GCAATGCGCG CTGCTGATTG GCC   173